(12) United States Patent
Shieh et al.

(10) Patent No.: US 7,706,870 B2
(45) Date of Patent: Apr. 27, 2010

(54) METHOD FOR ANALYZING IRREVERSIBLE APNEIC COMA (IAC)

(75) Inventors: Jiann-Shing Shieh, Taipei (TW); Bo-Kai Hu, Taipei (TW); Sheng-Jean Huang, Taipei (TW); Ming-Chien Kao, Taipei (TW)

(73) Assignee: Yuan Ze University, Taoyuan County (TW)

( * ) Notice: Subject to any disclaimer, the term of this patent is extended or adjusted under 35 U.S.C. 154(b) by 321 days.

(21) Appl. No.: 11/775,781

(22) Filed: Jul. 10, 2007

(65) Prior Publication Data

US 2009/0018460 A1    Jan. 15, 2009

(51) Int. Cl.
    *A61B 5/04* (2006.01)
(52) U.S. Cl. ..................................... 600/521
(58) Field of Classification Search ................... 600/521
    See application file for complete search history.

(56) References Cited

U.S. PATENT DOCUMENTS 5,622,178 A * 4/1997 Gilham ....................... 600/523
2007/0276275 A1 * 11/2007 Proctor et al. ............... 600/513

OTHER PUBLICATIONS

Mourot et al. Quantitative Poincare Plot analysis of Heart Rate Variability: Effect of Endurance Training. European Journal of Applied Physiology. 91:1 (2004) 79-87.*

Nereo Zamperetti et al.,; Irreversible apnoeic coma 35 years later; Journal; Jan. 14, 2004; pp. 1715-1722; Intensive Care Med, Springer-Verlag.

Eelco F.M. Wijdicks; Brain death worldwide Accepted fact but no global consensus in diagnostic criteria; Journal; 2002; Neurology; AAN Enterprises, Inc.

D. John Doyle, The Diagnosis of Brain; Journal; Mar. 3, 1995; vol. 2 No. 3; p. 1-7; Educational Synopses in Anesthesiology and Critical Care Medicine, The Online Journal of Anesthesiology.

B Shivalkar et al.,; Variable effects of explosive or gradual increase of intracranial pressure on myocardial structure and function; 1993; pp. 230-239; Circulation; American Heart Association; Texas.

David J Powner et al.,; Changes in Serum Catecholamine Levels in Patients Who Are Brain Dead; Journal; Nov./Dec. 1992; vol. 11 No. 6; pp. 1046-1053; The Journal of Heart and Lung Transplantation.

(Continued)

*Primary Examiner*—Carl H Layno
*Assistant Examiner*—Jeremiah T Kimball
(74) *Attorney, Agent, or Firm*—WPAT, P.C.; Anthony King

(57) ABSTRACT

An method for analyzing irreversible apneic coma (IAC) for determining the presence of irreversible apneic coma (IAC) by analyzing the heart rate variability of a brain traumatic patient, thereby providing a physician a reference index to determine whether brain death has occurred. This method includes, at first, recording an electrocardiogram (ECG) from a subject. Then, analyzing R-R interval in said electrocardiogram (ECG), and plotting said R-R interval into Poincaré plot, wherein the X coordinate in said Poincaré plot represents R-R interval(n), and n is a 1~data number. Y coordinate in said Poincaré plot represents RR(n+1). And, finally, quantifying said Poincaré plot, and obtaining semi-major axis (SD1), semi-minor axis (SD2), and SD1/SD2 of said Poincaré plot, as well as Poincaré plot area.

1 Claim, 32 Drawing Sheets

OTHER PUBLICATIONS

Martin Smith; Physiologic Changes During Brain Stem Death; Journal, Sep. 2004; vol. 23 No. 9S; pp. 2217-2222; The Journal of Heart and Lung Transplantation.

Thierry Rapenne et al.,; Could Heart Rate Variability Analysis Become an Early Predictor of Imminent Brain Death; Journal; 2000; pp. 329-336; Anesth Analg; International Anesthesia Research Society.

Mardi L. Sait et al.,; A study of heart rate and heart rate variability in human subjects exposed to occupational levels of Hz circularly polarised magnetic fields; Journal; 1999; pp. 361-369; Medical Engineering & Physics; Elsevier.

Solange Akselrod et al.,; Power Spectrum Analysis of Heart Rate Fluctuation; Jul. 10, 1981; pp. 222; vol. 213; AAAS.

Bruce Pomeranz et al.,; Assessment of autonomic function in humans by heart rate spectral analysis; Journal; 1985, The American Physiological Society.

J. Philip Saul et al.,; Assessment of Autonomic Regulation in Chronic congestive Heart Failure by Heart Rate Spectral Analysis; Journal; Jun. 1, 1988; vol. 61; pp. 1292-1299; Congestive Heart Failure; The American Journal of Cardiology.

KE Sands et al.,; Power spectrum analysis of heart rate variability in human cardiac transplant recipients; Journal; Jan. 1989; vol. 79 No. 1; pp. 75-82; Circulation; The American Heart Association; Texas.

Anna M. Bianchi et al.,; Time-Variant Power Spectrum Analysis for the Detection of Transient Episodes in HRV Signal; Journal; Feb. 1993; vol. 40 No. 2; pp. 136-144; IEEE Transactions on Biomedical Engineering.

Franco S; Design with operational amplifiers and analog integrated circuits; Text Book; 1988; Chapter 2, pp. 80-86; McGraw-Hill.

G D'Addio et al.,; Correlation between Power-law Behavior and Poincare Plots of Heart Rate Variability in Congestive heart Failure Patients; Journal; 1999; pp. 611-614; Computers in Cardiology; IEEE.

Mary A. Woo et al., Patterns of beat-to-beat heart rate variability in advanced heart failure; Journal; Mar. 1992; vol. 123 No. 3; American Heart Journal.

Junichiro Hayano et al.,; Prognostic value of heart rate variability during long-term follow-up in chronic haemodialysis patients with end-stage renal disease; Journal; 1999; pp. 1480-1488; Nephrology Dialysis Transplantation.

Mikko P. Tulppo et al.,; Quantitative beat-to-beat analysis of heart rate dynamics during exercise; Journal; 1996; pp. 244-252; The American Physiological Society.

Menrad A, et al.; Dual microprocessor system for cardiovascular data acquisition, processing and recording; Journal; 1981; pp. 64-69; IEEE Inr.Conf Industrial Elect. Contr. Instrument.

Fraden, J et al.,; QRS wave detection, Journal; Mar. 1980; vol. 18 No. 2; pp. 125-132; Medical and Biological Engineering and Computing; Springer Berlin/Heidelberg.

A John Camm et al.,; Heart rate variability Standards of measurement, physiological interpretation, and clinical use; Journal; 1996; vol. 17; pp. 354-381; European Society of Cardiology; American Heart Association Inc.

Stanton A. Glantz; Primer of Biostatistics, Text Book; 2006; Sixth Edition; pp. 367-373; McGraw-Hill; Norther America.

* cited by examiner

METHOD FOR ANALYZING IRREVERSIBLE APNEIC COMA (IAC)

BACKGROUND OF THE INVENTION

1. Field of the Invention

The invention relates to a method for analyzing irreversible apneic coma (IAC), and in particular, a method for analyzing irreversible apneic coma (IAC) based on the analysis of heart rate variability (HRV) by means of Poincaré plot.

2. Description of the Prior Art

In an intensive care unit, a patient with irreversible apneic coma (IAC) has a great risk of developing brainstem failure. Brainstem sites governing functions of the heart and of other physiological functions tend to undergo a secondary pathological change, and, causing "brain death" after a certain period time where functions of breathing and heart beating are lost. The patient's life would be irremediable when his condition passes the "irreversible point" of dying.

This condition happens generally to a patient of severe head trauma and bleeding beneath arachnoid membrane [1-2]. Clinically, IAC patient would be considered legally brain dead based on legally established standards and procedures. Inconsistencies do exists in different countries in their established standards and procedures to determine brain death, but they are based commonly on two tests, namely, the disappearance of brainstem reflexes and the apnea test [3]. The result of brainstem determination can confirm that the "irreversible point" has been reached. Nevertheless, there has been no sufficient amount of data in relative studies to accurately determine the exact point where the "irreversible point" occurs.

In Taiwan, the established standard and process for determining brain death on an IAC patient is very lengthy. When an attending physician makes a brain death determination on an IAC patient, there has to be an observation period of 12-72 hours prior to the brainstem functional test. Thereafter, the first brainstem reflexes test and an apnea test is performed to ascertain whether the patient exhibits the absence of brainstem reflexes and absolute apneal. The same two tests are repeated four hours later. The patient can be considered brain dead if the results of the repeated second set of tests confirm the absence of brainstem reflexes and absolute apnea. Due to such lengthy procedure, the patient may die halfway through the test, or before tests can be performed to determine legal brain death.

The current legal brain death determination process can not completely differentiate whether a patient has clinically reached the state of brain death. For example, because the determination of brain death needs to test whether the function of brainstem has the ability of spontaneous breathing, the precondition for an apnea test would be the normal operation of the lungs in the patient. Unfortunately, because of the absence of brainstem reflexes and already failing lung functions in many IAC patients, no apnea test can be performed on these patients. Consequently, many physicians believe this kind of IAC patients may have already achieved the state of clinical brain death.

A sympathetic storm is a hyperactive phenomenon occurring in the cardiovascular system in the event of cerebral stem infarction. In the event of cerebral stem infarction, there will be a local ischemia in cerebrospinal nerve, and in turn the sympathetic nerve can not respond to reflective stimulation, which result in tachycardia and the raise of mean arterial blood pressure, and hence into hyper-excitability [4]. In studies of organ donation patients, sympathetic storm is a common phenomenon [4-6]. Based on clinical observations, it has been found that tachycardia and hypertension can cause dramatic blood vessel constriction in IAC patients [5]. Additional studies also pointed out that studies on the heart beat variation in sympathetic storm show may have potential for facilitating the diagnosis of IAC patients [7]. So far, unfortunately, studies on sympathetic storm had been carried out merely in organ transplantation and in the laboratory. No study has yet been done applying heart beat variation in sympathetic storm on the diagnosis of clinical IAC patients.

Thus, it can be seen that the above-described brain death determination process and standard exhibits many disadvantages. It will be conducive to the established standard and procedure of determining brain death if there exists an effective analytical method specifically for IAC patients. Not only will such analytical method facilitate a physician in determining brain death of an IAC patient, it will also help in making timely arrangement of subsequent hospice care or organ donation.

Electrocardiography (ECG) had been introduced by Willem Einthoven, a Holland physiologist, to measure electric current changes during systolic phase by means of a string galvanometer, and record its changing profile on a chart. This technique was later developed into the electrocardiography (ECG) extensively used in modern medical diagnosis. The constriction of cardiac muscles is caused by a string of processes comprising polarizing, depolarizing and re-polarizing of cardiac muscles. The electric current generated during this process can distribute throughout the body such that it can be sensed by electrode patches adhered to the patient's skin. The electric current is plotted mechanically and displayed as a wave, called an electrocardiogram (ECG). Electrocardiography (ECG) depicts the initiation, order, direction, magnitude and the length of the duration of the cardiac muscle systolic current, as well as the condition of the cardiac physiological activities.

Because the frequencies of human heart beat is not very rhythmic, even at very calm and steady state, the observed interval between heart beats exhibits a variation of tens of milliseconds, which is called heart rate variability (HRV). HRV is a fluctuation that is produced from the action of cardiovascular contrition and dilation nerve center in the brain. Heart rate is influenced primarily by two factors, of which one is the constant discharge frequency of the sinoatrial pacemaker cell; the other is the control of autonomic nervous system (ANS) including sympathetic nerve system that increases heart beat and parasympathetic nerve system that suppresses heart beat [8].

Since characteristics of HRV can be changed instantly due to external environmental stimulations (e.g., postural changes, drug action, nursing activities, etc.) and intrinsic physiological mechanism (e.g., angry, happy, tension, etc.), and its length of duration of each heart beat can be affected by factors such as blood pressure change (blood pressure reflective regulation), breath (response to parasympathetic nerve from the chest pressure sensor), body temperature regulation (body temperature regulation mechanism response to the sympathetic nerve and influencing blood flow) and the circadian rhythm, long-term observation on heart beat signals can be used to monitor abnormal physiological phenomena of the heart (arrhythmia, ventricular tachycardia, ventricular fibrillation, etc.). And, therefore, HRV can be developed into a physiological monitoring index. In the electrocardiogram, the easiest measured parameter is the most significant peak-to-peak interval of R wave. Accordingly, the heart beat duration is determined generally based on the peak-to-peak interval of R wave, which is referred also as heart beat interval or R-R interval. In present researches, R-R interval is analyzed commonly with frequency domain and time domain.

The frequency domain analysis of HRV [9] is based on the fast Fourier transform (FFT) performed on R-R intervals, in which signals that are varied with time are converted into spectra of heart beat interval. A spectrum is a function of frequency; its intensity is the square of the sinusoidal amplitude of this frequency. A relative intensity can be quantified into a power spectral density (PSD). In a characteristic spectrum of a heart beat variation, two kinds of spectral peaks can be observed generally—a low frequency band and a high frequency band. There are different definitions on a low frequency band and a high frequency band in research literatures, and the most widely used definitions are low frequency in the range of 0.04~0.15 Hz and high frequency in the range of 0.15~0.40 Hz [9]. In the study of Akselrod et al. [9], it is pointed out that the extremely low frequency part of a spectrum governs the temperature regulation in a human body, which is within the control of sympathetic nerve, while the high frequency part manages breathing, which is within the regulation of parasympathetic nerve. The ratio between the extremely low frequency and the high frequency can be used to describe the equilibrium condition of the automatic nerve system. Further, a frequency domain marker can be utilized to measure one's psychological stress, since a psychological stress is generated from the activation of high-level cardiovascular never center and is displayed in the low frequency domain of a heart beat spectrum. The spectral analysis of a heart beat variation facilitates further identification on body temperature regulation mechanism, peripheral vessel contrition nerve, adrenaline angiotensin, and the like [9, 10].

Since the 1981 disclosure by Akselrod et al. that heart beat spectral characteristics can be used to differentiate actions between sympathetic nerve and parasympathetic nerve [9, 10], a number of different signal procession methods have been applied to resolve the interrelation between HRV and the action of automatic nerve system, as well as for assessing the action of automatic nerve system on the change of heart beat regulation under various pathological conditions [11, 12]. Instant characteristics can be utilized to monitor meanings represented by the characteristic change of heart beat induced through stimulations on the automatic nerve system under various conditions, including detecting the occurrence of local ischemia in a patient with myocardial infarction [13], evaluating the physiological condition of patients under dizziness or narcosis [14].

D'Addio et al. had analyzed the HRV of a patient with cardiac failure by means of a nonlinear analytical method, Poincaré plot, and had divided roughly the geometrical shape of a Poincaré plot into four types: comet, torpedo, fan, and complex [15, 16]. In addition, D'Addio et al. had postulated that the comet type stands for a lower heart beat and the increase of HRV; the torpedo type is narrower than the comet type and approaches a diagonal line, and represents a small difference between contiguous heart beats. In the fan type, not only is the difference between contiguous heart beats small, but contiguous heart beats as a whole is also restricted within a small range, while the complex type represents a combination of several heart beat intervals. Later, D'Addio et al. further proposed concept of 3D Poincaré plot which considered the Z axis as frequency at the same point, and presented a concept of density as well as relative parameters for 3D quantification [17]. Furthermore, Tulppo et al. [18] had proposed a way to quantify a 2D Poincaré plot, comprising an ellipsoid approach to Poincaré plot, and calculating by standard deviation the SD1 and SD2 as the major axis and minor axis, respectively, and involving parameters of SD1, SD2, SD1/SD2, and area.

Viewing that brainstem failure of a IAC patient can induce the uncontrollability of an automatic nerve, and might cause further cardiac pathological changes, the inventor believes that heart rate variability should change dramatically before and after the occurrence of a sympathetic storm in such patient, and had analyzed the heart rate variation of patients and normal peoples in order to develop an efficient IAC analytical method.

SUMMARY OF THE INVENTION

The invention provides a method for analyzing irreversible apneic coma (IAC). Said method analyzes the heart rate variability of a subject by a Poincaré plot. In the method according to the invention, R-R intervals are used to analyze the heart rate variability of a subject. There are two ways to detect R-R intervals. The first is based on the process proposed by Meard [19] that uses only a first derivative (FD1) to detect R-R intervals. It proceeds by dividing 30-minute ECG information into units each of 2 seconds. The method can be described as the following:

X(n): ECG raw data $$Y(n)=-2X(n-2)-X(n-1)+X(n+1)+2X(n+2)$$

$$2<n<1000 \qquad (1)$$

Next, for detecting the position of R wave in Y(n), a slope threshold is defined as the following:

$$\text{Slope threshold}=0.7\max[Y(n)] \ 2<n<1000 \qquad (2)$$

If Y(i)>slope threshold, Y(i) becomes the region for comparison. Positions of each peak can be selected out of Y(i), where the distance between adjacent peaks is the R-R intervals.

The second way is based on the process proposed by Fraden and Nueman [20], which detects R-R intervals using both amplitude threshold and first derivative (hereinafter as AF2). This process can be described as the following:

$$\text{Amplitude threshold}=0.4\max[X(n)] \ 0<n<1000$$

The original data are converted into Y0(n):

$$Y0(n)=X(n) \text{ if } X(n)\geq 0 \ 0<n<1000$$

$$Y0(n)=-X(n) \text{ if } X(n)<0 \ 0<n<1000 \qquad (3)$$

From amplitude threshold, an Y1(n) can be obtained:

$$Y1(n)=Y0(n) \text{ if } Y0(n)\geq \text{Amplitude threshold}$$

$$Y1(n)=\text{Amplitude threshold if } Y0(n)<\text{Amplitude threshold} \qquad (4)$$

Then, an Y2(n) is obtained by means of first derivative:

$$Y2(n)=Y1(n+1)-Y1(n-1) \ 1<n<2 \qquad (5)$$

Thus, in order to detect the position of R wave in Y2(n), a slope threshold=0.7 is defined and as FD1, define Y(i)>0.7, a comparison can be performed and peak values can be found out.

Each 30-minute ECG data is analyzed by FD1 and AF2, respectively. Those data with 100% detection success is subject to analyze further.

The method proposed according to the invention resides on analyzing HRV of a subject, and uses frequency domain analysis (Power Spectral) and time domain analysis (statistical method) as references for analysis results obtained. A Poincaré plot analysis involves, under time domain, disarranging geometrically original R-R intervals and plotting on the same 2D diagram. On said 2D diagram, X coordinate is R-R interval(n), where n is 1~data number, abbreviated as RR(n), while Y coordinate represents RR(n+1). The X and Y coordinates of each point represent the relationship between each R-R interval and next R-R interval. Then, the quantification of Poincaré plot is performed. There are 3 ways to quantify Poincaré plot:

The first one is the measurement of geometrical profile (e.g., radius, length, width, etc.) through defining new axes as X1 and X2 based on the method proposed by Tulppo [16]:

$$\begin{bmatrix} x1 \\ x2 \end{bmatrix} = \begin{bmatrix} \cos\theta & -\sin\theta \\ \sin\theta & \cos\theta \end{bmatrix} \begin{bmatrix} RR_n \\ RR_{n+1} \end{bmatrix} \quad (8)$$

where SD1 and SD2 represent the semi-major axis and semi-minor axis of a ellipse, respectively defined as followed:

$$SD1^2 = \text{Var}(x_1) = \text{Var}\left(\frac{1}{\sqrt{2}}RR_n - \frac{1}{\sqrt{2}}RR_{n+1}\right) \quad (9)$$
$$= \frac{1}{2}\text{Var}(RR_n - RR_{n+1}) = \frac{1}{2}SDSD^2$$

$$SD2^2 = 2SDRR^2 - \frac{1}{2}SDSD^2 \quad (10)$$

wherein, SDRR is the standard deviation of R-R interval, and SDSD is the standard deviation of $\Delta RR_n$. By using the above-described method, the area of the ellipse can be obtained as $\Pi \times SD1 \times SD2$.

The second way consists of approaching mathematically, such as, for example, approaching the derivative profile of a distribution with a triangular or exponential curve.

The third way comprises dividing the diagram into ellipsoid, complex, fan and torpedo types and counts statistically the number of each type present. However, there are some types not easily defined.

These features and advantages of the present invention will be fully understood and appreciated from the following detailed description of the accompanying drawings.

BRIEF DESCRIPTION OF THE DRAWINGS

FIG. 1-2 shows the result obtained by converting ECG signals utilizing FD1 process.
FIG. 1-3 shows R-R intervals.
FIG. 2-1 is a Re-sampled R-R interval ($X_k$).
FIG. 2-2 is a spectrum.
FIG. 3-1 to FIG. 3-58 shows Poincaré plots of every subject tested.

DETAILED DESCRIPTION OF THE PREFERRED EMBODIMENT

Example 1

Collection of Clinical Data

1. Subjects Studied

Figure 1:
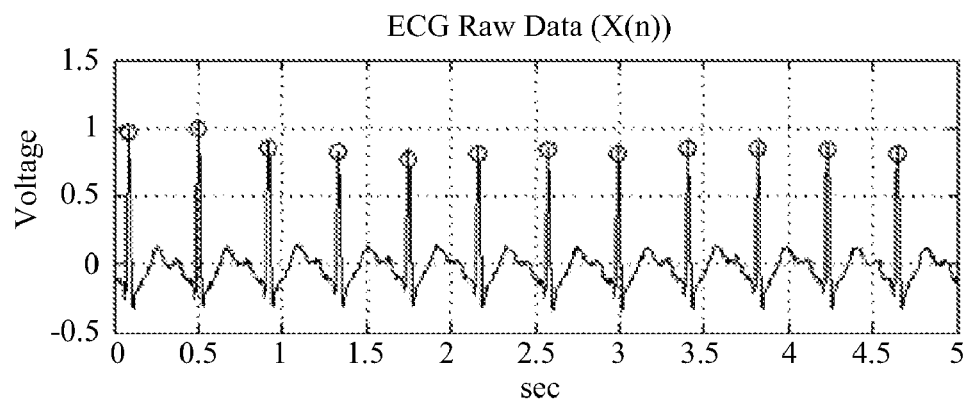
FIG. 1-1 is ECG original signals.

Based on the presence or absence of IAC (irreversible apneic coma) as well as on GCS (Glasgow coma scale), subjects studied in this example were divided into 3 groups. As shown in Table 1, the first group consisted of healthy subjects (normal) of 22-25 years old as control. The second group consisted of ordinary patients without IAC in neurosurgical intensive care unit of National Taiwan University Hospital (Taipei, Taiwan) and they were divided into two sub-groups of light coma (9-15) and deep coma (4-8). The third group consisted of patients with IAC in neurosurgical intensive care unit of National Taiwan University Hospital. They were adults with severe brain traumatic IAC caused by head injury. Since sympathetic storm is a mechanism caused by local ischemia in brain spinal, patients with automatic nerve disorder caused by other factors, such as, for example, brain ischemia due to trauma, spinal nerve injury, cardiac arrhythmia, diabetes, or patients with known cardiac diseases were excluded automatically out of the third group. Among subjects in the third group, there were two more sub-groups, namely, sub-group without brain death determination and sub-group with brain death determination (because of signed consent of organ donation). The absence of spontaneous breathing ability and brainstem reflexes were confirmed through currently established standard and procedure, in patients with determined brain death.

TABLE 1

Basic information of experimental groups

| Main group | Sub-group | GCS | No. | Case No. | Sex (male/female) | Ages |
|---|---|---|---|---|---|---|
| (1) Normal | — | 15 | 16 | 1~16 | 16/0 | 22.7 ± 1.08 |
| (2) Ordinary patients | (2b) Light coma | 9~15 | 19 | 17~35 | 10/9 | 56.74 ± 19.73 |
|  | (2a) Deep coma | 4~8 | 7 | 36~42 | 4/3 | 52.43 ± 23.27 |
| (3) IAC patients | (3a) With brain death determination | 3 | 5 | 43~47 | 4/1 | 41.8 ± 13.81 |
|  | (3b) Without brain death determination | 3 | 11 | 48~58 | 7/4 | 48.0 ± 19.73 |
| Total | — | — | 58 | — | 42/16 | 43.95 ± 20.90 |

2. Instruments for Measurement and Data Collection

In this example, the heart beat of subjects tested were monitored with a Patient Monitoring Philips MP60. By virtue of the function of outputting an analog original signal voltage of Patient Monitoring Philips MP60, the electrocardiogram signal (ECG) of a subject can be outputted to a signal retrieving system that consists of a multifunction Data Acquisition Card (DAQ Card-6024E) and a computer. The multifunction Data Acquisition Card (DAQ Card-6024E) can transform the received electrocardiogram signal (ECG) into a digital signal and stored it in that computer.

Healthy subjects (normal) in the first group were monitored for their physiological signals while sitting over 1-2 hours with one half hour as one unit. Subjects (non-IAC patients) in the second group stay in decubitus position and had artificial intubations during monitoring physiological signals for 1-2 hours, with one half hour as one unit.

Subjects (IAC patients) in the third group were subjected to monitor their physiological signals for 24-72 hours. The monitoring conditions for subjects in the third group were based on the regulation established by the Brain Trauma foundation (BTF): when the intracranial pressure (ICP) increased, the sickbed had to be tilted such that the head of the patient is inclined 30 degrees so as to lower the ICP. For maintaining at a cerebral perfusion pressure above 60 mmHg, drugs such as nor-epinephrine and dopamine were administered for constricting blood vessel and raising blood pressure. For lowering intracranial pressure, drugs such as Neurosedative therapy, mannitol and the like were administered. In addition, the end tidal carbon dioxide was kept in a range of 30 to 33 mmHg by means of mechanical venting. The thus-gathered data were divided into one segment per one half hour, and data interfered by nursing factors (e.g., patting back or pulling out phlegm) were excluded. Furthermore, brain stem reflexes of patients were recorded, namely, pupil reflex, cornea light reflex, oculovestibular reflex, eye semicircular canal reflex, and Gag reflexes.

Example 2

Experimental Analytical Method

1. Heart Rate Variability (HRV)

Heart rate variability (HRV) of subjects was analyzed using R-R intervals. In this example, two methods for detecting R-R intervals were used: the first one was based on the method proposed by Meard [19] in which First Derivative (FD1) was used to detect R-R intervals. In this example, 30-minute ECG information (as shown in FIG. 1-1) was treated by dividing the information into 2 seconds per one unit. The method comprised is as follows:

X(n): ECG raw data $$Y(n)=-2X(n-2)-X(n-1)+X(n+1)+2X(n+2)$$

$$2<n<1000 \quad (1)$$

Figures 1, 2:
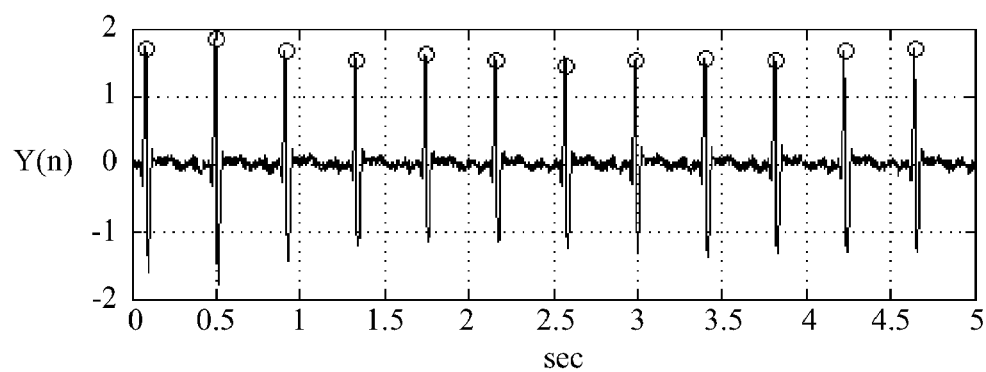

FIG. 1-2 shows the result after transforming the information into Y(n). As shown in FIG. 1-2, among ECG signals, Q wave and S wave with original positive and negative values, respectively, were transformed into values near 0, while R wave remained no significant change. Next, for detecting the position of R wave in Y(n), a slope threshold was defined as follow:

$$\text{Slope threshold}=0.7\max[Y(n)] \quad 2<n<1000 \quad (2)$$

Figures 1, 2, 3:
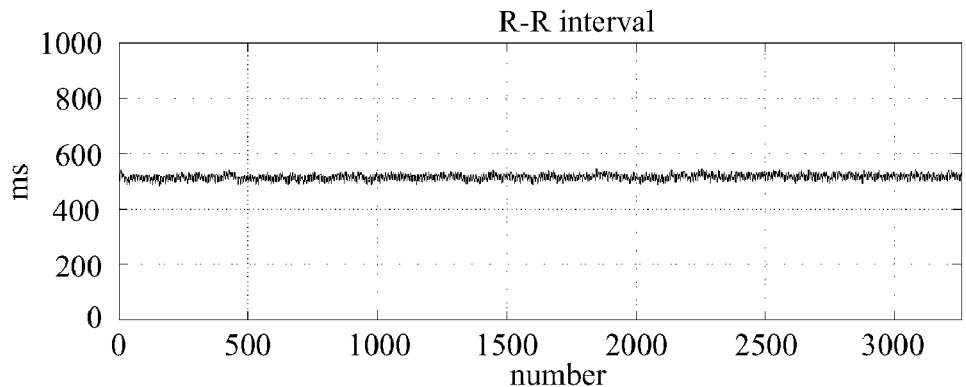
Figures 1, 2:
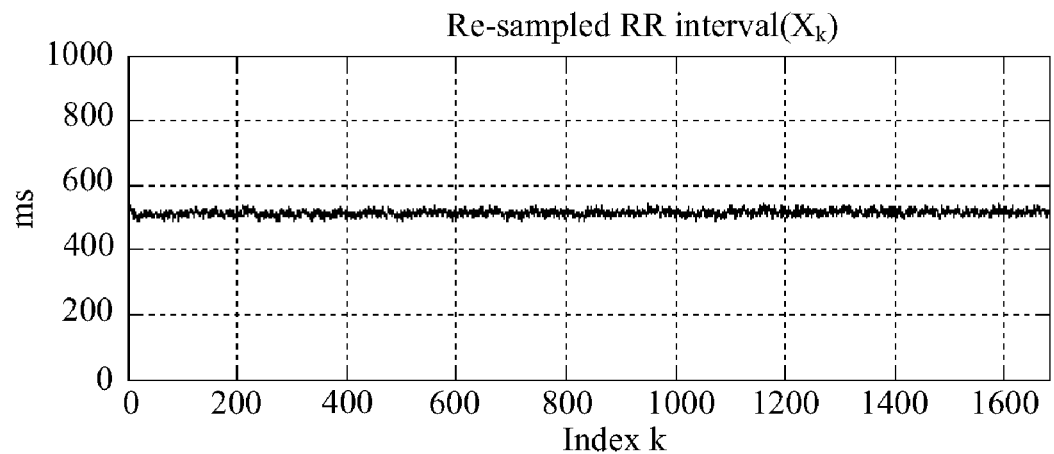
Figure 2:
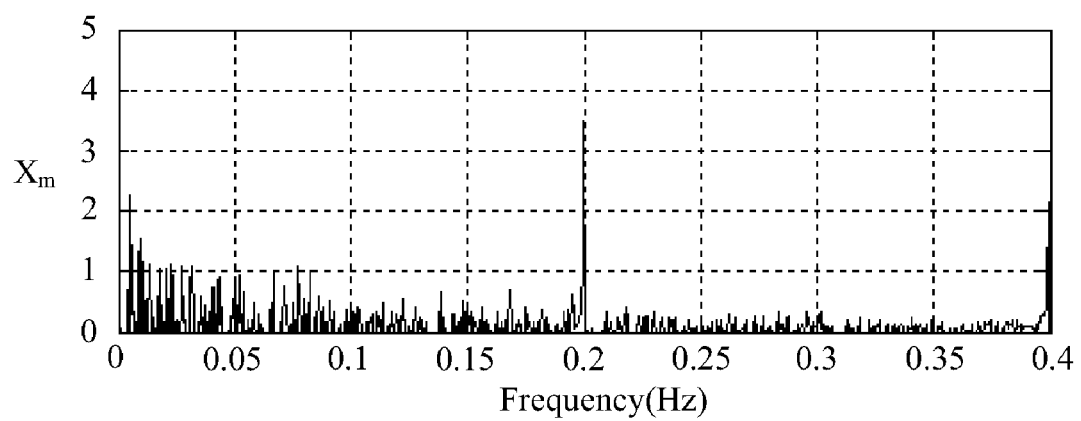

If Y(i)>slope threshold, Y(i) became the region for comparison. Position of each peak can be selected within Y(i), where the distance between adjacent peaks was R-R intervals. FIG. 1-3 shows R-R intervals within one half hour, where X axis represents the number of heart beats, and Y axis represents R-R intervals (ms).

The second method was based on that proposed by Fraden and Nueman [20], in which both an amplitude threshold and a first derivative were used to detect R-R intervals (abbreviated as AF2). The method comprised as follow:

$$\text{Amplitude threshold}=0.4\max[X(n)] \quad 0<n<1000$$

The original data were transformed into Y0(n):

$$Y0(n)=X(n) \text{ if } X(n)\geqq 0 \quad 0<n<1000$$

$$Y0(n)=-X(n) \text{ if } X(n)<0 \quad 0<n<1000 \quad (3)$$

Based on amplitude threshold, Y1(n) could be obtained $$Y1(n)=Y0(n) \text{ if } Y0(n)\geqq \text{Amplitude threshold}$$

$$Y1(n)=\text{Amplitude threshold if } Y0(n)<\text{Amplitude threshold} \quad (4)$$

Next, a first derivative was taken to obtain Y2(n):

$$Y2(n)=Y1(n+1)-Y1(n-1) \quad 1<n<2 \quad (5)$$

Then, for detecting the position of R wave in Y2(n) a slope threshold was defined to be 0.7; and as FD1, define Y(i)>0.7, a comparison can be performed and peak values can be determined.

Each 30-minute ECG data is analyzed by FD1 and AF2, respectively. Those data with 100% detection success is subject to analyze further.

2. Frequency Domain Analysis for Heart Rate Variation-Power Spectral

R-R intervals detected as above were subjected to Power Spectral analysis. The Power Spectral analytical method was carried out as follow:

(1) Re-sampling of RR Interval

Since R-R interval had not a constant frequency, R-R intervals detected above must be re-sampled and transformed into constant frequency. The re-sampling method was as follows: R-R interval without a constant frequency originally was transformed into new sequence $X_k$ (as shown in FIG. 2-1) by means of difference technique. The constant frequency transformed in this study was 2 Hz.

(2) Fast Fourier Transform

By means of equation (6), the number sampled was N (N is an even number), and $X_m$ was the result from Fourier transformation of $X_k$. Based on $X_m$ and frequency, a frequency domain plot of this R-R interval could be depicted (as shown in FIG. 2-2).

$$X_m = \sum_{k=0}^{N-1} x_k e^{-j(2\pi k m/N)} \quad (6)$$

wherein m=0, 1, . . . , N−1.

The sum of area under frequency is the energy density $P_m$, the energy density $P_m$ of N values could be calculated as formula (7). Frequency distribution and energy amount could be obtained through this transformation way.

$$P_m \equiv \frac{1}{N}|X_m|^2 \qquad (7)$$

Finally, a ratio of high frequency power to total power (HFP/TP) was used as the quantitative marker for parasympathetic nerve activity; while low frequency power to high frequency power (LFP/HFP) was used as the marker for the activity equilibrium between sympathetic nerve and parasympathetic nerves [21].

3. Time Domain Analysis of Heart Beat Variation—statistical Method

Time domain analytical method can be classified into a statistical method and a geometrical method. The statistical method consists of performing statistical operation on R-R intervals detected above. Markers commonly used for heart beat variability includes as follow:

(1) The Mean R-R Interval (mean)
(2) Standard Deviation (SD)
(3) Coefficient of Variance (CV)
(4) The root mean square successive difference in R-R intervals (RMSSD)
(5) Standard Deviation of Differences between Adjacent RR Intervals (SDSD)

4. Time Domain Analysis of Heart Beat Variation—geometrical Method—Poincaré Plot Geometrical method consists of drawing sequence of R-R intervals into geometrical pattern, such as, for example, Lorenz Plot and Poincaré plot, and an evaluation can be performed by virtue of geometrical features, such as area, shape, density and the like. In this example, Poincaré plot was used to analyze heart beat variability.

Figures 1, 3:
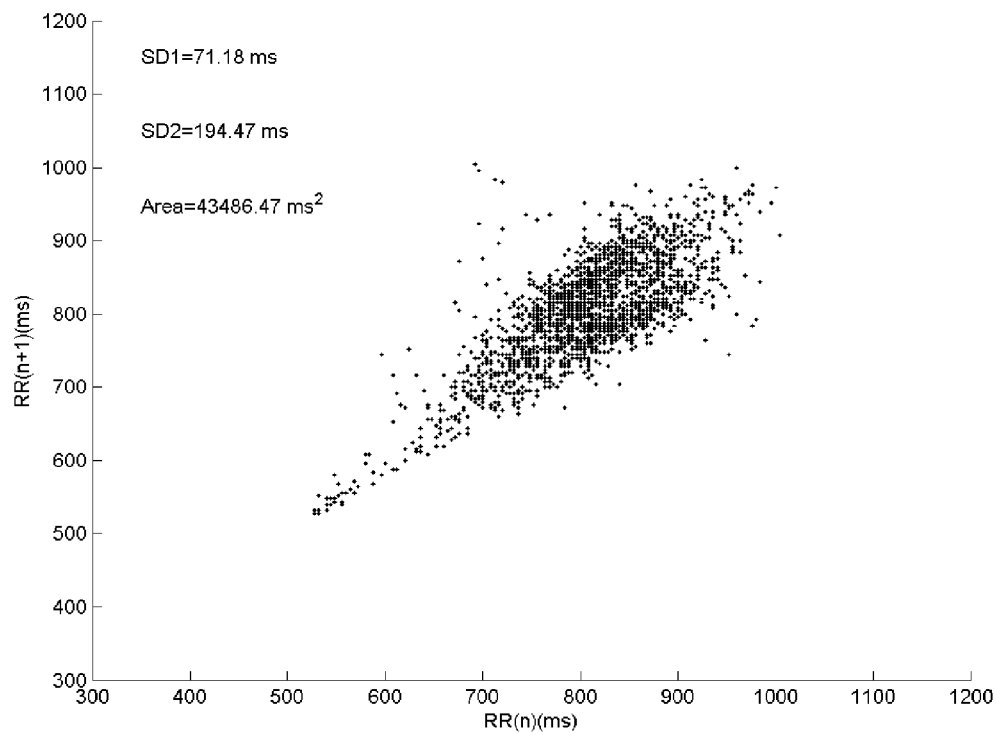
Figures 2, 3:
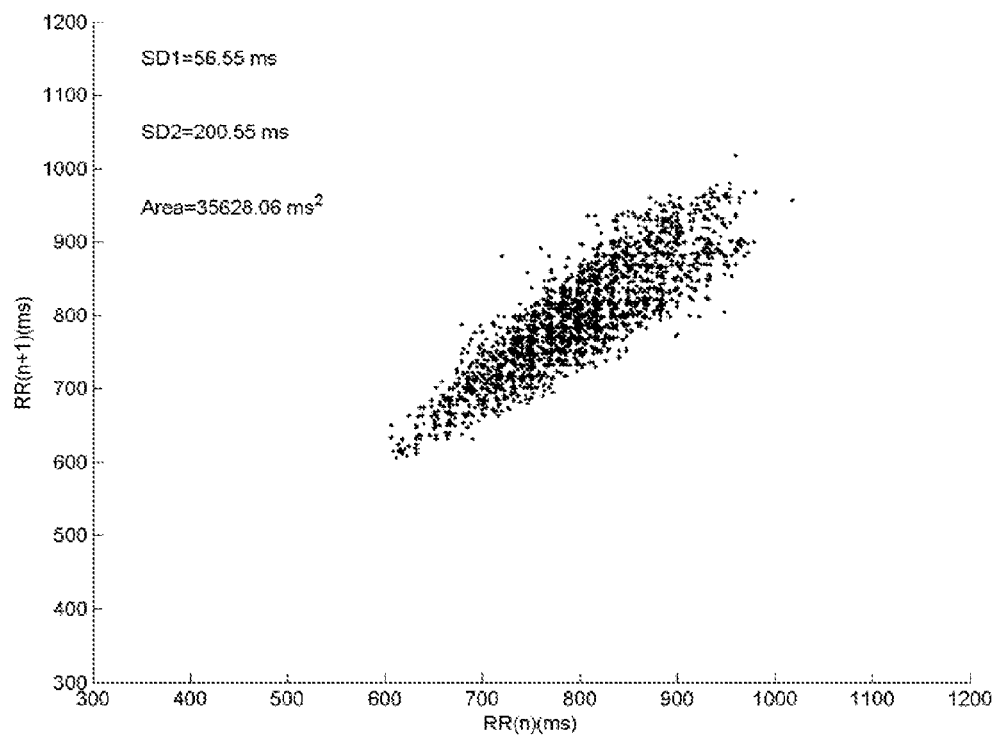
Figure 3:
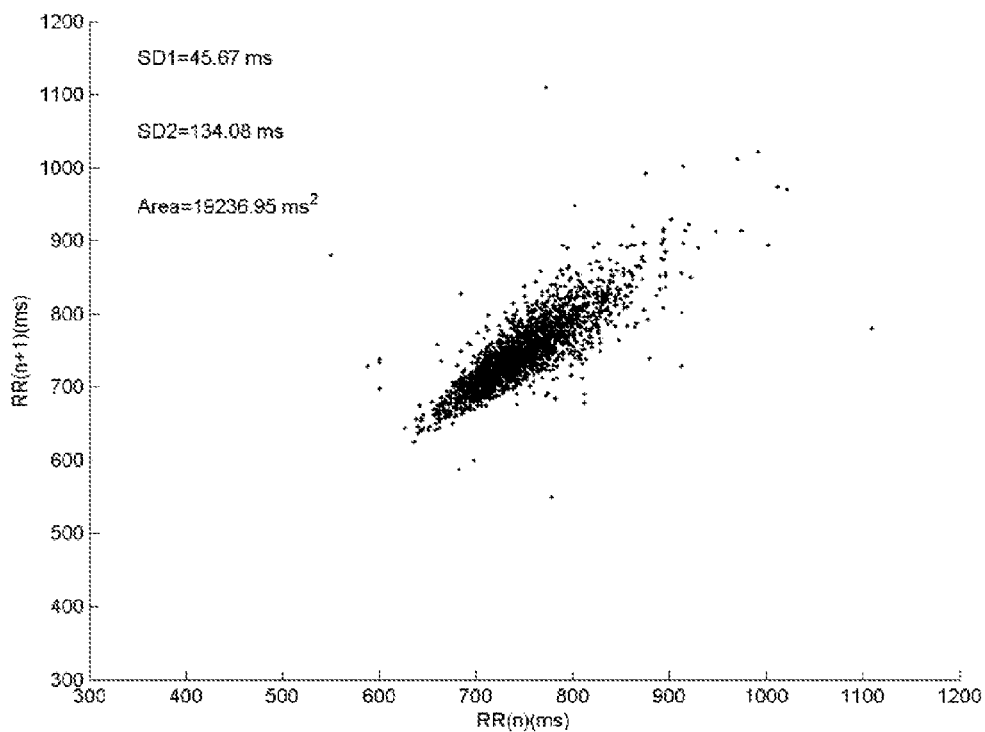
Figures 3, 4:
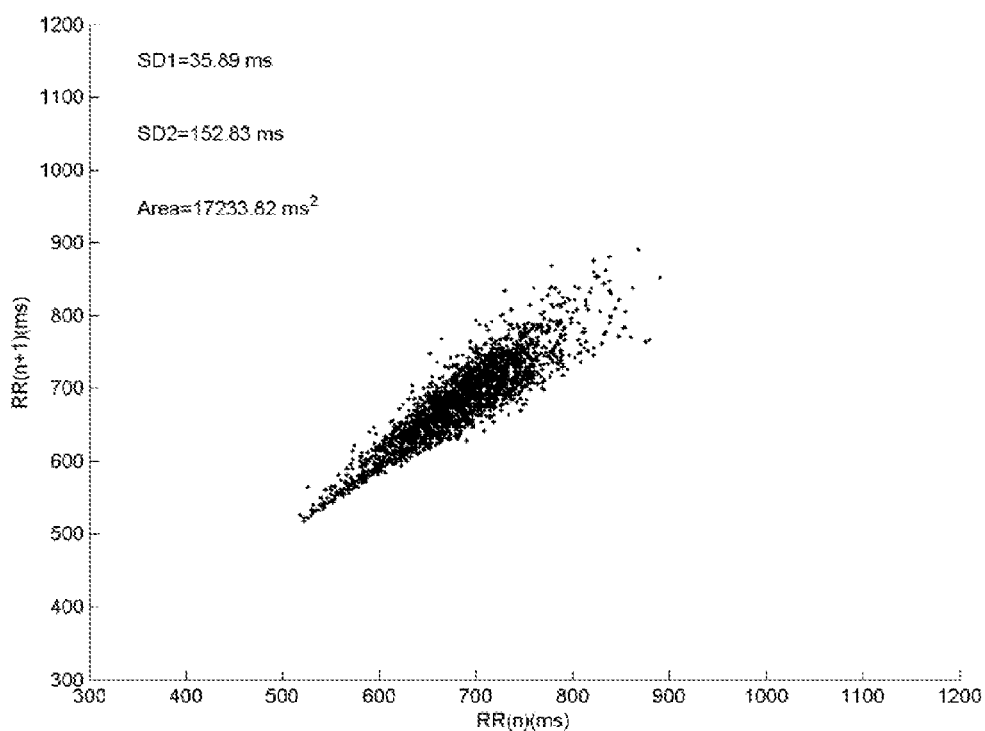

Poincaré plot is an application of the chaos theory. A number of studies utilize this method to analyze the relationship of heart beat variability [15-20]. By using geometrical way under time domain, original R-R intervals were disarranged and plotted them on the same 2D plot. On that 2D plot, X coordinate represented R-R interval(n), where n was 1~data number, and abbreviated as RR(n) hereinafter; Y coordinate represented RR(n+1). The meaning of X and Y coordinates of each point stood for the interrelationship between R-R interval each time and R-R interval next time, as shown in FIG. 3-1 to FIG. 3-58.

In a standard care practice in an intensive care unit, a patient would be subject to care activities such as turning the body over, pulling out phlegm or patting back every two hours. In order to obviate interference from artificial factors, the Poincaré plot sampling time was one hour in this example, and divided into one unit per one half hour to be analyzed. Then, the quantification of Poincaré plot was carried out. This example employed measurements of geometrical profile (e.g. radius, length, width and the like). Referring to FIG. 4, and by way of FIG. 3-2, in this example, new axes as X1 and X2 were defined based on the method proposed by Tulppo [16]:

$$\begin{bmatrix} x1 \\ x2 \end{bmatrix} = \begin{bmatrix} \cos\theta & -\sin\theta \\ \sin\theta & \cos\theta \end{bmatrix} \begin{bmatrix} RR_n \\ RR_{n+1} \end{bmatrix} \qquad (8)$$

where SD1 and SD2 represented semi-major axis and semi-minor axis of the ellipse with their definitions as follow:

$$SD1^2 = \mathrm{Var}(x_1) = \mathrm{Var}\left(\frac{1}{\sqrt{2}}RR_n - \frac{1}{\sqrt{2}}RR_{n+1}\right) \qquad (9)$$
$$= \frac{1}{2}\mathrm{Var}(RR_n - RR_{n+1}) = \frac{1}{2}SDSD^2$$

$$SD2^2 = 2SDRR^2 - \frac{1}{2}SDSD^2 \qquad (10)$$

Wherein SDRR was the standard deviation of R-R interval, SDSD was the standard deviation of $\Delta RR_n$. Based the above-described method, the area of the ellipse in FIG. 4 could be obtained as $\Pi \times SD1 \times SD2$.

In addition, based on the distribution of every point in Poincaré plot:

(1) Points closer to the left lower corner represent higher heart beat rate of the subject; on the other hand, points closer the right upper corner represent lower heart beat rate of the subject.
(2) Points closer to the diagonal represent more normal heart beat of the subject since its adjacent numbers of heart beat time are closer each other.
(3) When approach as an ellipse, the major axis SD2 represents the distance between the slowest and the rapidest heart beat rate within the standard deviation, whereby a long-term change can be observed.
(4) When approach as an ellipse, the minor axis SD1 reveals the difference between the number of adjacent heart beat times.
(5) SD1/SD2 represents a marker for equilibrium of heart beat regulation.
(6) Area of the ellipse (i.e., Poincaré Area) represents the condition of entire heart rate distribution.

Example 3

Results

1. Analysis of Poincaré Plots

Every subject of each group was analyzed individually for R-R interval, and separately drew Poincaré plot for each subject (as shown in FIG. 3-1 to FIG. 3-58). In addition, the R-R interval of each subject was analyzed by Power Spectral, statistical method, and Poincaré plot. Results were shown in Table 2-1 to Table 2-5.

Due to the great variability of R-R intervals among healthy subjects (normal) in the first group, Poincaré plots of all 16 healthy subjects were of comet type distribution (as shown in FIG. 3-1 to FIG. 3-16). Their Poincaré plots exhibited features as: (1) bigger area; (2) longer SD2; (3) SD1/SD2 of about ⅓. Because Poincaré plots displayed a distribution on the diagonal, it is suggested that subjects demonstrated a close adjacent heart beats. Further, since points on Poincaré plots spread within effective range in a comet shape, it is suggested that under long-term monitoring, subjects exhibit great heart rate variability.

Based on the GCS index of subjects, subjects in the second group were classified into two sub-groups of slight coma patients (9-15) and deep coma patients (4-8). Poincaré plots of slight coma patients gave no specific feature, and displayed all of the possible shape (i.e., torpedo, comet, and fan types), as shown in FIG. 3-17 to FIG. 3-35. Likewise, R-R intervals and Poincaré plots of deep coma patients demonstrated no specific shape (as shown in FIG. 3-36 to FIG. 3-42). Moreover, Poincaré plots of the same subject at different time points might present entirely different conditions. Their exhibited Poincaré Areas between brain death and a normal, but might have a comet type a as normal had. Consequently, it could be suggested that the coma degree possessed no absolutely positive relationship with heart rate variation, the heart of a coma subject could have a normal operation. Nevertheless, a patient with deepest coma (GCS scale=3) might have his brain stem central nerve become necrosis due to apnea coma, where function of heart rate variation might be affected.

Among subjects in the third group, IAC patients with brain death determination (sub-group 3a), their R-R intervals presented often a status of no variability (as shown in FIG. 3-43 to FIG. 3-47), and their Poincaré plots assumed mostly a distribution of fan type. Further, their Poincaré plots exhibited the following features: (1) extremely small Poincaré Area; (2) longer SD2, but its SD1/SD2 ratio is near 1:1; (3) extremely small variability under long-term monitoring (each point restricted within a narrow range, presented as "centered on one point"). Since heart rate variation was governed by automatic nerve, it was postulated that in case of extremely small variability under long-term monitoring, sympathetic and parasympathetic nerves could no longer regulate heart rate variation, but remained only sinoatrial cell keeping on a constant discharging frequency.

Likewise, IAC patients without brain death determination (sub-group 3b) often had their R-R intervals presented with a status of no variability (as shown in FIG. 3-48 to FIG. 3-58); their Poincaré plots also assumed mostly a distribution of fan type and their Poincaré Areas were small (about 300-1500 $ms^2$). Whether IAC patients with or without brain death determination, both of them exhibited extremely small Poincaré Areas and this situation was lasted for a very long time period. Therefore, it could be suggested that, although there may be times IAC patients do not reach the condition of brain death (such as, complete absence of brain stem reflexes and lose of spontaneous breathing ability), relative portions governed by their brain stems and hearts have already failed.

TABLE 2-1

Data of heart rate variability of Group 1 (Normal Testers)

| Case no. | Group | GCS | Sex | Age | HFP/TP | LFP/HFP | HR (beat/min) | Mean (ms) | SD (ms) | CV (%) |
|---|---|---|---|---|---|---|---|---|---|---|
| 1 | normal | 15 | male | 22 | 0.1812 | 1.4476 | 74.31 | 807.43 | 73.22 | 9.07 |
| 2 | normal | 15 | male | 22 | 0.1144 | 1.69 | 75.1 | 798.97 | 73.67 | 9.22 |
| 3 | normal | 15 | male | 22 | 0.0867 | 3.7284 | 80.22 | 747.93 | 50.08 | 6.7 |
| 4 | normal | 15 | male | 22 | 0.0769 | 2.997 | 87.72 | 683.98 | 55.5 | 8.11 |
| 5 | normal | 15 | male | 22 | 0.1389 | 2.0034 | 71.89 | 834.59 | 72.1 | 8.64 |
| 6 | normal | 15 | male | 22 | 0.1366 | 1.9564 | 71.7 | 836.81 | 102.08 | 12.2 |
| 7 | normal | 15 | male | 22 | 0.0667 | 4.9785 | 72.15 | 831.66 | 79.03 | 9.5 |
| 8 | normal | 15 | male | 22 | 0.353 | 0.7578 | 62.44 | 960.95 | 73.42 | 7.64 |
| 9 | normal | 15 | male | 22 | 0.1545 | 1.408 | 77.62 | 773.02 | 68.03 | 8.8 |
| 10 | normal | 15 | male | 22 | 0.1124 | 3.0343 | 86.12 | 696.72 | 47.45 | 6.81 |
| 11 | normal | 15 | male | 25 | 0.1329 | 1.7859 | 58.52 | 1025.27 | 63.26 | 6.17 |
| 12 | normal | 15 | male | 24 | 0.1574 | 2.7335 | 64.55 | 929.56 | 58.47 | 6.29 |
| 13 | normal | 15 | male | 25 | 0.1709 | 1.2023 | 51.91 | 1155.76 | 65.26 | 5.65 |
| 14 | normal | 15 | male | 23 | 0.1317 | 1.9985 | 59.62 | 1006.31 | 98.34 | 9.77 |
| 15 | normal | 15 | male | 23 | 0.1201 | 3.0265 | 83.35 | 719.90 | 63.46 | 8.82 |
| 16 | normal | 15 | male | 23 | 0.0708 | 5.7943 | 85.98 | 697.83 | 35.53 | 5.09 |

| Case no. | SDSD (ms) | RMSSD (ms) | SD1 (ms) | SD2 (ms) | SD1/SD2 | Poincaré Area(ms2) |
|---|---|---|---|---|---|---|
| 1 | 50.33 | 2254.26 | 71.18 | 194.47 | 0.366 | 43486.47 |
| 2 | 39.99 | 1874.68 | 56.55 | 200.55 | 0.282 | 35628.06 |
| 3 | 32.29 | 1549.36 | 45.67 | 134.08 | 0.3406 | 19236.95 |
| 4 | 25.38 | 1282.96 | 35.89 | 152.83 | 0.2349 | 17233.82 |
| 5 | 46.37 | 2131.68 | 65.58 | 193.09 | 0.3397 | 39781.91 |
| 6 | 59.3 | 2726.36 | 83.86 | 276.28 | 0.3035 | 72785.03 |
| 7 | 37.38 | 1717.65 | 52.87 | 217.19 | 0.2434 | 36074.41 |
| 8 | 47.86 | 2049.08 | 67.68 | 196.33 | 0.3447 | 41747.79 |
| 9 | 44.87 | 2128.83 | 63.46 | 181.66 | 0.3493 | 36214.1 |
| 10 | 23.3 | 1164.93 | 32.95 | 130.11 | 0.2533 | 13467.64 |
| 11 | 49.42 | 1865.6 | 69.89 | 164.71 | 0.4243 | 36165.21 |
| 12 | 44.95 | 1785.22 | 63.58 | 152.67 | 0.4164 | 30491.67 |
| 13 | 56.75 | 2004.18 | 80.26 | 166.21 | 0.4829 | 41911.17 |
| 14 | 75.95 | 2911.05 | 107.41 | 256.56 | 0.4187 | 86574.46 |
| 15 | 39.14 | 1792.62 | 55.35 | 170.76 | 0.3241 | 29691.19 |
| 16 | 15.69 | 699.29 | 22.19 | 98.01 | 0.2264 | 6830.97 |

TABLE 2-2

Data of heart rate variability of Group 2a (GCS: 9~15)

| Case no. | Group | GCS | Sex | Age | HFP/TP | LFP/HFP | HR (beat/min) | Mean (ms) | SD (ms) | CV (%) | SDSD (ms) | RMSSD (ms) | SD1 (ms) | SD2 (ms) | SD1/SD2 | Poincaré Area(ms2) |
|---|---|---|---|---|---|---|---|---|---|---|---|---|---|---|---|---|
| 17 | clear | 15 | male | 44 | 0.0853 | 3.0756 | 59.21 | 1013.28 | 58.61 | 5.78 | 16.63 | 588.09 | 23.52 | 164.1 | 0.1433 | 12127.37 |
| 18 | clear | 15 | male | 51 | 0.0137 | 6.0505 | 92.34 | 649.78 | 20.27 | 3.12 | 4.5 | 210.24 | 6.37 | 56.99 | 0.1118 | 1140.58 |
| 19 | clear | 15 | male | 69 | 0.0875 | 0.975 | 63.24 | 948.83 | 19.5 | 2.06 | 19.72 | 609.17 | 27.89 | 47.58 | 0.5862 | 4169.44 |
| 20 | clear | 15 | female | 63 | 0.1647 | 1.6204 | 95.9 | 625.66 | 17.33 | 2.77 | 18.59 | 959.15 | 26.29 | 41.39 | 0.6351 | 3417.52 |
| 21 | clear | 15 | male | 63 | 0.1764 | 1.178 | 92.95 | 645.51 | 20.45 | 3.17 | 11.71 | 548.12 | 16.56 | 55.42 | 0.2989 | 2883.93 |
| 22 | clear | 15 | female | 63 | 0.08 | 1.7755 | 99.04 | 605.82 | 32.37 | 5.34 | 17.1 | 754.08 | 24.18 | 88.29 | 0.2739 | 6707.21 |
| 23 | clear | 15 | female | 99 | 0.3712 | 0.8960 | 88.05 | 681.46 | 40.18 | 5.90 | 30.91 | 1339.06 | 43.71 | 104.92 | 0.4166 | 14407.13 |
| 24 | clear | 15 | male | 53 | 0.0250 | 0.7598 | 87.39 | 686.58 | 48.24 | 7.03 | 8.52 | 358.06 | 12.05 | 135.91 | 0.0887 | 5145.03 |
| 25 | coma | 14 | female | 23 | 0.0202 | 12.2050 | 95.62 | 627.45 | 33.99 | 5.42 | 9.65 | 442.32 | 13.64 | 95.17 | 0.1434 | 4079.44 |
| 26 | coma | 13 | male | 44 | 0.0392 | 3.832 | 97.83 | 613.31 | 14.82 | 2.42 | 6.18 | 194.77 | 8.74 | 41.01 | 0.2132 | 1126.14 |
| 27 | coma | 13 | female | 51 | 0.076 | 3.4058 | 76.65 | 782.79 | 32.84 | 4.2 | 17.9 | 820.46 | 25.32 | 89.38 | 0.2833 | 7109.39 |
| 28 | coma | 13 | female | 56 | 0.0744 | 2.8215 | 55.78 | 1075.65 | 67.26 | 6.25 | 40.35 | 1309.38 | 57.06 | 181.49 | 0.3144 | 32536.48 |
| 29 | coma | 10 | male | 63 | 0.0177 | 1.7595 | 74.16 | 809.07 | 31.68 | 3.92 | 9.16 | 377.76 | 12.96 | 88.67 | 0.1462 | 3610.45 |
| 30 | coma | 10 | female | 76 | 0.0794 | 1.8306 | 79.88 | 751.1 | 22.24 | 2.96 | 8.19 | 368.38 | 11.59 | 61.82 | 0.1875 | 2250.51 |
| 31 | coma | 10 | female | 29 | 0.035 | 4.1108 | 105.85 | 566.85 | 55.28 | 9.75 | 19.09 | 825.02 | 27 | 154 | 0.1753 | 13060.76 |
| 32 | coma | 9 | male | 33 | 0.7624 | 0.1077 | 79.27 | 756.94 | 28.89 | 3.82 | 43.1 | 2055.21 | 60.95 | 54.43 | 1.1199 | 10421.52 |
| 33 | coma | 9 | female | 53 | 0.1101 | 1.7247 | 95.12 | 630.8 | 83.18 | 13.19 | 21.66 | 981.85 | 30.64 | 233.27 | 0.1313 | 22452.79 |
| 34 | coma | 9 | male | 80 | 0.0683 | 1.7249 | 114.62 | 523.46 | 18.39 | 3.51 | 7.35 | 315.07 | 10.4 | 50.96 | 0.204 | 1664.38 |
| 35 | coma | 9 | male | 65 | 0.0444 | 3.9518 | 95.27 | 629.79 | 21.63 | 3.43 | 8.22 | 332.34 | 11.62 | 60.07 | 0.1934 | 2192.83 |

TABLE 2-3

Data of heart rate variability of Group 2b (GCS: 5~9)

| Case no. | Group | GCS | Sex | Age | HFP/TP | LFP/HFP | HR (beat/min) | Mean (ms) | SD (ms) | CV (%) | SDSD (ms) | RMSSD (ms) | SD1 (ms) | SD2 (ms) | SD1/SD2 | Poincaré Area(ms2) |
|---|---|---|---|---|---|---|---|---|---|---|---|---|---|---|---|---|
| 36 | coma | 8 | female | 73 | 0.0652 | 2.867 | 99.43 | 603.43 | 22.98 | 3.81 | 7.05 | 362.47 | 9.97 | 64.23 | 0.1552 | 2011.74 |
| 37 | coma | 8 | male | 17 | 0.0129 | 4.4863 | 94.62 | 634.14 | 85.38 | 13.46 | 12.68 | 629.53 | 17.93 | 240.83 | 0.0745 | 13566.54 |
| 38 | coma | 7 | male | 80 | 0.0805 | 0.8651 | 72.65 | 825.89 | 68.18 | 8.25 | 36.19 | 1537.65 | 51.18 | 185.92 | 0.2753 | 29894.95 |
| 39 | coma | 7 | male | 60 | 0.227 | 1.6228 | 64.54 | 929.72 | 81.48 | 8.76 | 57.79 | 2326.04 | 81.73 | 215.48 | 0.3793 | 55326.13 |
| 40 | coma | 6 | male | 44 | 0.1024 | 2.9825 | 87.43 | 686.26 | 29.59 | 4.31 | 18.31 | 860.25 | 25.9 | 79.58 | 0.3254 | 6473.98 |
| 41 | coma | 6 | female | 29 | 0.4369 | 0.6893 | 81.86 | 732.97 | 37.69 | 5.14 | 25 | 1178.35 | 35.36 | 100.56 | 0.3516 | 11171.07 |
| 42 | coma | 5 | female | 64 | 0.2727 | 0.5932 | 69.43 | 864.16 | 18.04 | 2.09 | 21.96 | 752.38 | 31.05 | 40.5 | 0.7667 | 3951.58 |

TABLE 2-4

Data of heart rate variability of Group 3a

| Case no. | Group | GCS | Sex | Age | HFP/TP | LFP/HFP | HR (beat/min) | Mean (ms) | SD (ms) | CV (%) | SDSD (ms) | RMSSD (ms) | SD1 (ms) | SD2 (ms) | SD1/SD2 | Poincaré Area(ms2) |
|---|---|---|---|---|---|---|---|---|---|---|---|---|---|---|---|---|
| 43 | OD | 3 | male | 47 | 0.1621 | 0.3179 | 84.8 | 707.55 | 12.11 | 1.71 | 9.88 | 437.72 | 13.98 | 31.28 | 0.4469 | 1373.57 |
| 44 | OD | 3 | male | 45 | 0.4781 | 0.3405 | 98.53 | 608.94 | 10.04 | 1.65 | 8.1 | 295.65 | 11.46 | 25.99 | 0.441 | 935.75 |
| 45 | OD | 3 | female | 18 | 0.3515 | 0.1777 | 79.63 | 753.47 | 12.33 | 1.64 | 6.45 | 282.4 | 9.12 | 33.66 | 0.2709 | 963.94 |
| 46 | OD | 3 | male | 54 | 0.1079 | 0.9806 | 71.89 | 834.63 | 14.15 | 1.69 | 8.32 | 281.91 | 11.77 | 38.24 | 0.3078 | 1414.29 |
| 47 | OD | 3 | male | 45 | 0.2068 | 0.2291 | 129.44 | 463.52 | 4.76 | 1.03 | 7.17 | 384.1 | 10.14 | 8.84 | 1.1462 | 281.59 |

TABLE 2-5

Data of heart rate variability of Group 3b

| Case no. | Group | GCS | Sex | Age | HFP/TP | LFP/HFP | HR (beat/min) | Mean (ms) | SD (ms) | CV (%) | SDSD (ms) | RMSSD (ms) | SD1 (ms) | SD2 (ms) | SD1/SD2 | Poincaré Area(ms2) |
|---|---|---|---|---|---|---|---|---|---|---|---|---|---|---|---|---|
| 48 | IAC | 3 | male | 55 | 0.2106 | 0.3976 | 116.59 | 514.61 | 6.43 | 1.25 | 2.13 | 89.47 | 3.01 | 17.94 | 0.1678 | 169.69 |
| 49 | IAC | 3 | male | 39 | 0.3112 | 0.3928 | 111.03 | 540.4 | 5.77 | 1.07 | 4.63 | 216.71 | 6.54 | 14.96 | 0.4373 | 307.48 |
| 50 | IAC | 3 | male | 73 | 0.0583 | 0.4731 | 65.77 | 912.28 | 5.62 | 0.62 | 3.2 | 116.21 | 4.52 | 15.23 | 0.2967 | 216.3 |
| 51 | IAC | 3 | female | 45 | 0.2285 | 1.087 | 113.93 | 526.63 | 3.99 | 0.76 | 3.28 | 162.76 | 4.64 | 10.29 | 0.4506 | 149.98 |
| 52 | IAC | 3 | male | 29 | 0.475 | 0.673 | 120.71 | 497.04 | 3.66 | 0.74 | 5.93 | 256.72 | 8.38 | 6.05 | 1.3845 | 159.43 |
| 53 | IAC | 3 | female | 52 | 0.4835 | 0.7268 | 94.76 | 633.16 | 7.26 | 1.15 | 9.03 | 343.01 | 12.77 | 16.08 | 0.7937 | 645.01 |
| 54 | IAC | 5 | male | 21 | 0.1193 | 3.7818 | 96.49 | 621.8 | 18.82 | 3.03 | 7.87 | 384.39 | 11.12 | 52.04 | 0.2137 | 1818.74 |
| 55 | IAC | 3 | female | 38 | 0.241 | 0.2214 | 103.37 | 580.44 | 6.17 | 1.06 | 5.41 | 233.96 | 7.65 | 15.69 | 0.4874 | 376.95 |

TABLE 2-5-continued

Data of heart rate variability of Group 3b

| Case no. | Group | GCS | Sex | Age | HFP/TP | LFP/HFP | HR (beat/min) | Mean (ms) | SD (ms) | CV (%) | SDSD (ms) | RMSSD (ms) | SD1 (ms) | SD2 (ms) | SD1/SD2 | Poincaré Area(ms2) |
|---|---|---|---|---|---|---|---|---|---|---|---|---|---|---|---|---|
| 56 | IAC | 3 | male | 68 | 0.8447 | 0.1396 | 155.71 | 385.32 | 8.72 | 2.26 | 16.75 | 930.97 | 23.68 | 6.89 | 3.437 | 512.75 |
| 57 | IAC | 3 | male | 18 | 0.0604 | 3.9545 | 100.52 | 596.91 | 5.65 | 0.95 | 5.17 | 227.4 | 7.32 | 14.22 | 0.5147 | 326.94 |
| 58 | IAC | 3 | female | 77 | 0.8715 | 0.0785 | 70.76 | 848.00 | 8.11 | 0.96 | 12.50 | 488.29 | 17.67 | 14.62 | 1.2086 | 811.77 |

2. Statistical Analysis

At first, data that could not be used such as, those generated due to interference from nursing activities, QRS detection error and the like, were excluded from all data of patients measured. Results thus obtained were shown in Table 2-1 to Table 2-5. Then, an analysis was performed by using a non-parametric statistical method. At first, a statistics was made by means of Kruskal-Wallis (K-W test) [22], and its result was shown in Table 3. K-W test is the extension of Wilcoxon rating and test, and can apply to a problem of more than three independent random samples. K-W test proceeds similar to F test in terms of analyzing variables, except that no assumption of data as normal population is needed, rather than assuming random samples are independent with one another and come from a same population.

TABLE 3

Heart rate variability of subjects in each group obtained by Kruskal-Wallis and Dunn's test statistics.

| | Group 1 (n = 16) (GCS: 15) | Group 2 (n = 26) (GCS: 4~15) | Group 3 (n = 16) (GCS = 3) | P-value |
|---|---|---|---|---|
| Basic Index | | | | |
| GCS | $15^{ab}$ | $10^{ac}$ | $3^{bc}$ | <0.0001 |
| | (15~15) | (5~15) | (3~3) | |
| Age (yr) | $22^{ab}$ | $58^{a}$ | $45^{b}$ | <0.0001 |
| | (22~25) | (17~99) | (18~77) | |
| HR (beat/min) | $73.23^{ab}$ | $87.74^{a}$ | $99.53^{b}$ | <0.0001 |
| | (51.91~87.72) | (55.78~114.62) | (65.77~155.71) | |
| R-R interval Index | | | | |
| R-R mean (ms) | $819.54^{b}$ | 683.86 | $602.92^{b}$ | 0.0003 |
| | (683.98~1155.76) | (523.46~1075.65) | (385.3~912.28) | |
| SD (ms) | $66.65^{ab}$ | $32.02^{ac}$ | $6.84^{bc}$ | <0.0001 |
| | (35.53~102.08) | (14.82~85.38) | (3.66~18.82) | |
| CV | $8.38^{ab}$ | $4.25^{ac}$ | $1.11^{bc}$ | <0.0001 |
| | (5.09~12.2) | (2.06~13.46) | (0.62~3.03) | |
| SDSD (ms) | $44.91^{ab}$ | $17.5^{ac}$ | $6.81^{bc}$ | <0.0001 |
| | (15.69~75.95) | (4.5~57.79) | (2.13~16.75) | |
| RMSSD (ms) | $1870.14^{ab}$ | $690.95^{ac}$ | $282.15^{bc}$ | <0.0001 |
| | (699.29~2911.05) | (194.77~2326.04) | (89.47~930.97) | |
| Frequency domain Index | | | | |
| HF/TP | 0.13 | $0.08^{c}$ | $0.23^{c}$ | 0.0020 |
| | (0.07~0.35) | (0.01~0.76) | (0.06~0.87) | |
| LFP/HFP | $2^{b}$ | $1.77^{c}$ | $0.4^{bc}$ | <0.0001 |
| | (0.76~5.79) | (0.11~12.21) | (0.08~3.95) | |
| Poincaré Index | | | | |
| SD1 (ms) | $63.52^{ab}$ | $24.75^{ac}$ | $9.63^{bc}$ | <0.0001 |
| | (22.19~107.41) | (6.37~81.73) | (3.01~23.68) | |
| SD2 (ms) | $176.21^{ab}$ | $88.48^{ac}$ | $15.46^{bc}$ | <0.0001 |
| | (98.01~276.28) | (40.5~240.83) | (6.05~52.04) | |
| SD1/SD2 | 0.34 | $0.24^{c}$ | $0.45^{c}$ | 0.0020 |
| | (0.23~0.48) | (0.07~1.12) | (0.17~3.44) | |
| Area (ms$^2$) | $36119.81^{ab}$ | $5809.5^{ac}$ | $444.85^{bc}$ | <0.0001 |
| | (6831~86574.5) | (1126.1~55326.1) | (150~1818.7) | |

$^{a}$P < 0.05 Normal vs Patient using Dunn's test
$^{b}$P < 0.05 Normal vs IAC using Dunn's test
$^{c}$P < 0.05 Patient vs IAC using Dunn's test As shown in Table 3, after gathering statistics by K-W test, P-values of all parameters in three groups were less than 0.05. This indicated that all parameters in three groups had significant variation. Hence, variability between every two groups was then analyzed by Dunn's test [22] based on nonparametric statistics. The statistical result of Dunn's test could be described as follow:

(1) Frequency domain index (HF/TP and LFP/HFP) was incapable to distinguish variations between normal and ordinary patients.
(2) R-R interval Index (R-R mean, SD, CV, SDSD, and RMSSD) and Poincaré Index gave P-value<0.05 under analysis of Dunn's test. Obviously, these two methods could distinguish variability between every two groups. However, Poincaré Index could provide pattern-wise information for distinguishing, which facilitated the differentiation among different groups simpler and clearer than that provided by R-R interval Index.

Figures 3, 4, 5:
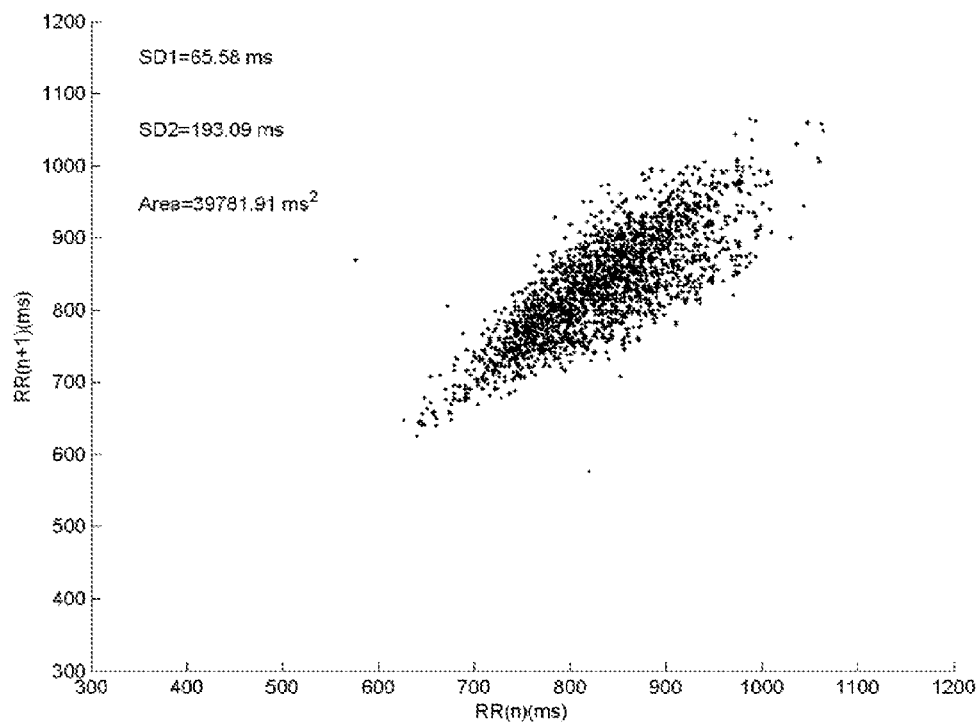
Figures 3, 4, 5, 6:
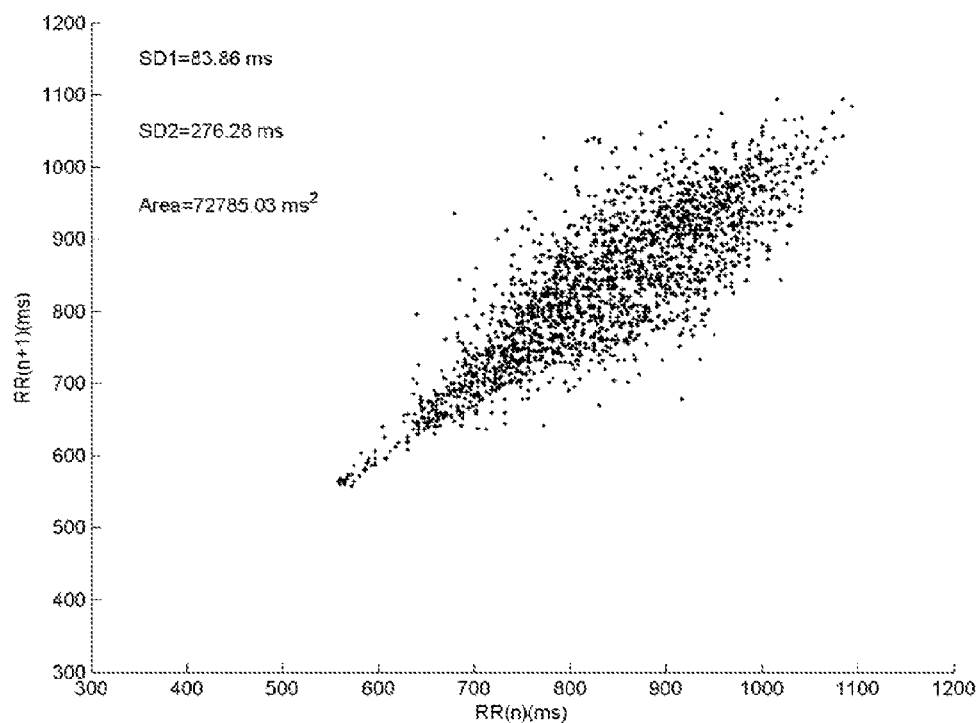
Figures 3, 4, 5, 6, 7:
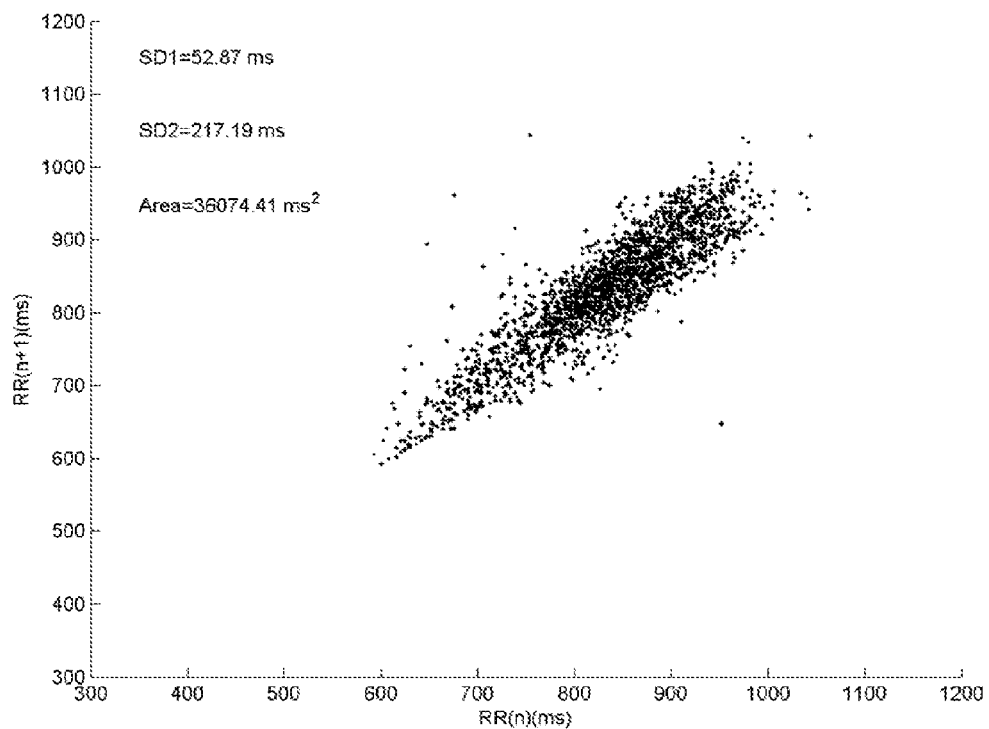
Figures 3, 4, 5, 6, 7, 8:
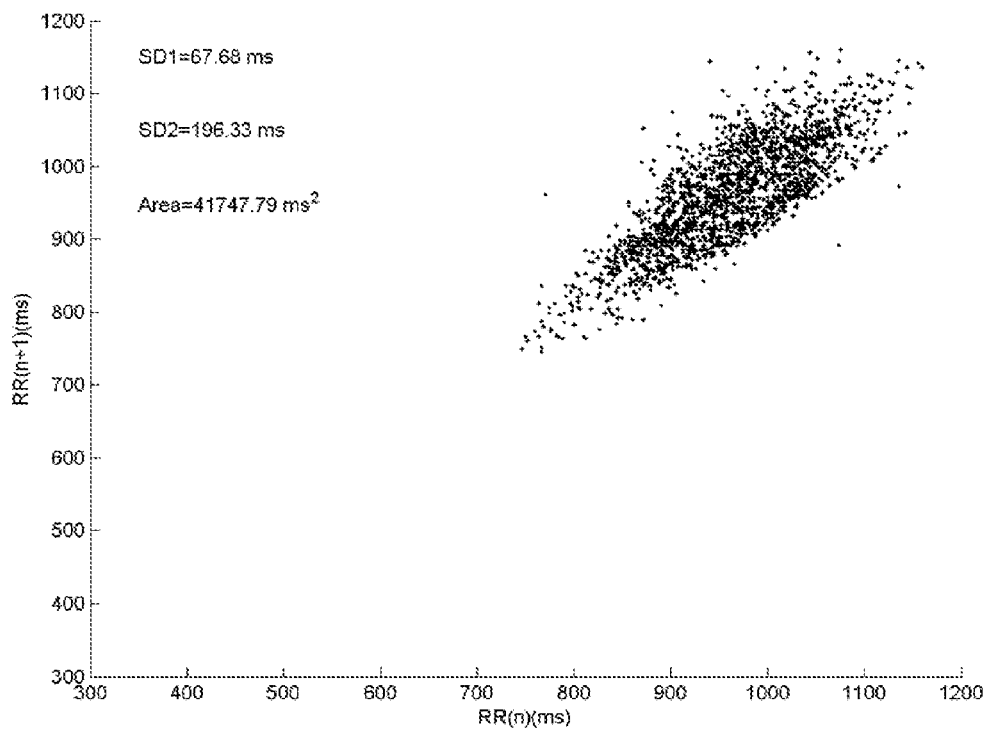
Figures 3, 4, 5, 6, 7, 8, 9:
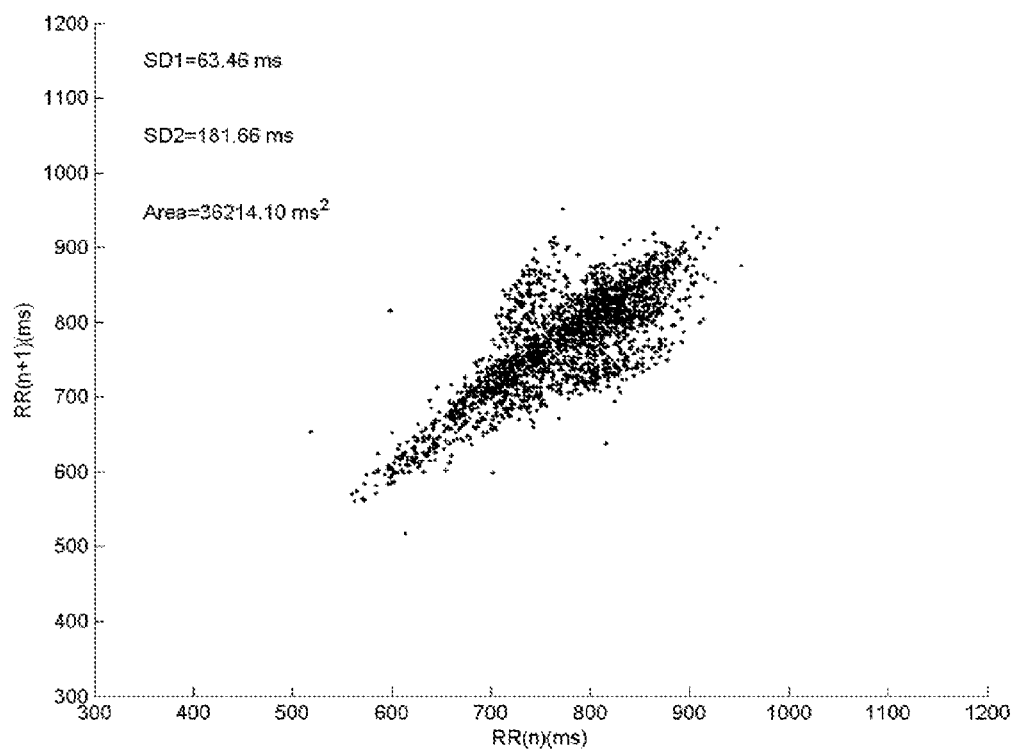
Figures 3, 4, 5, 6, 7, 8, 9, 10:
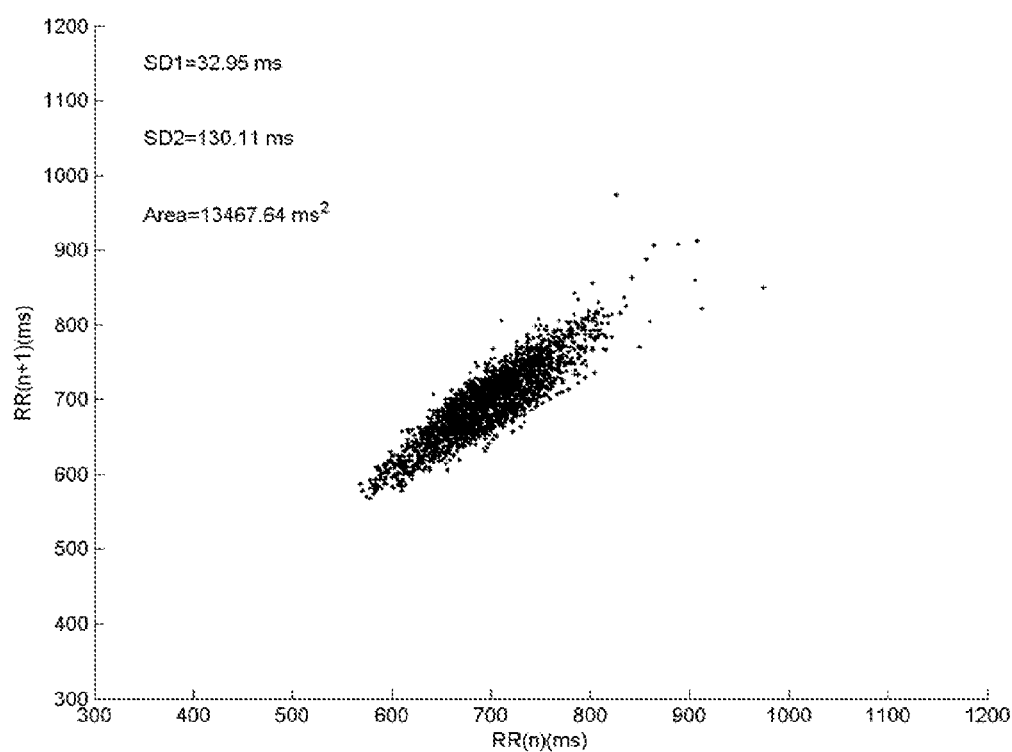
Figures 3, 4, 5, 6, 7, 8, 9, 10, 11:
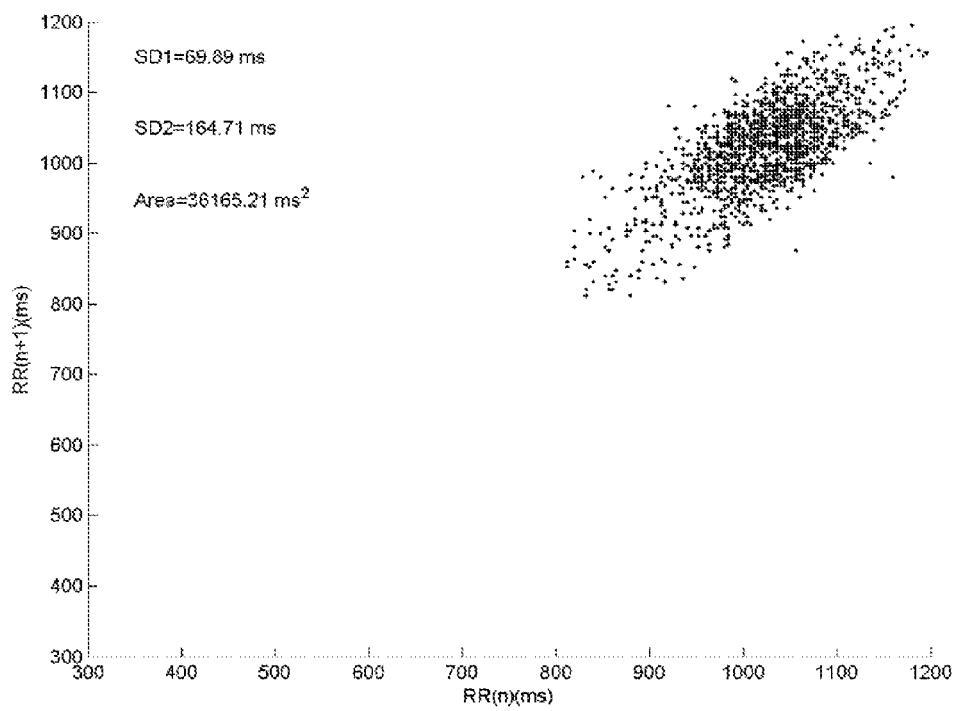
Figures 3, 4, 5, 6, 7, 8, 9, 10, 11, 12:
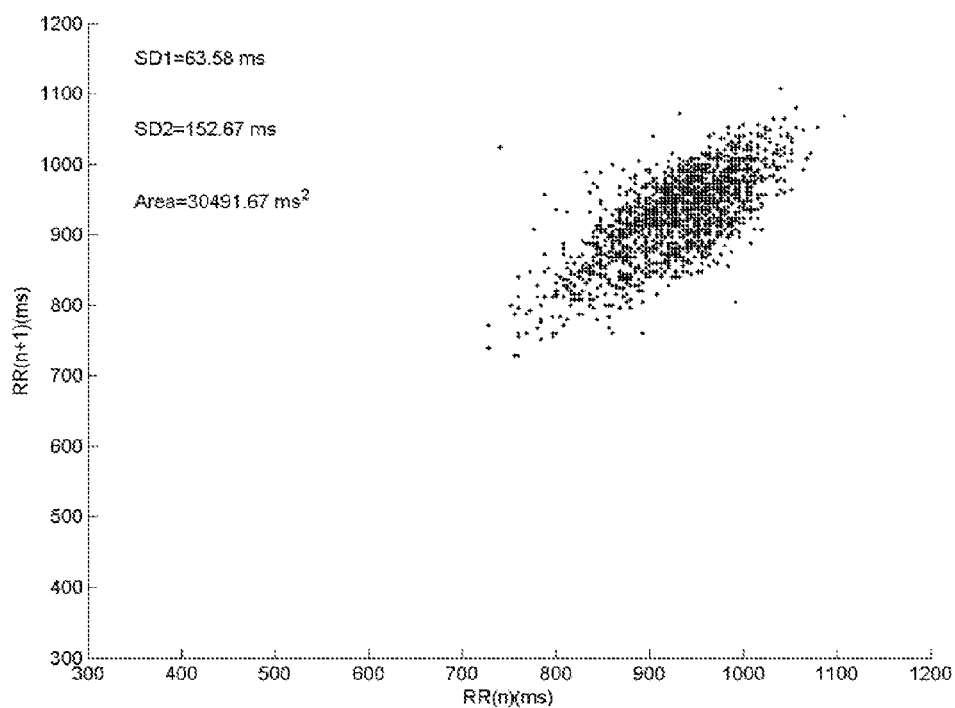
Figures 3, 4, 5, 6, 7, 8, 9, 10, 11, 12, 13:
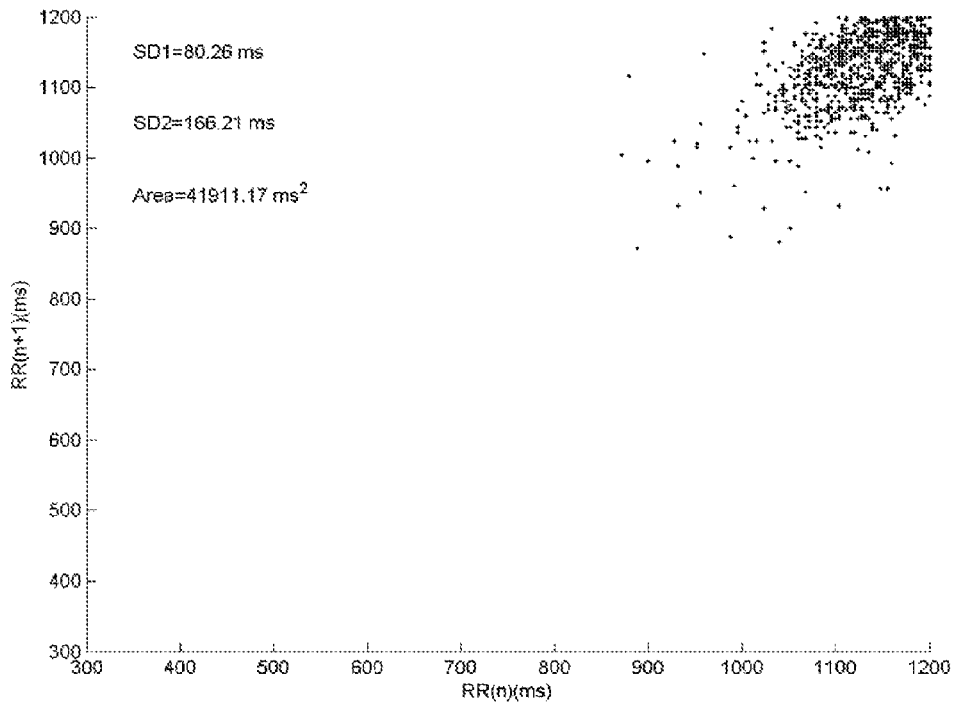
Figures 3, 4, 5, 6, 7, 8, 9, 10, 11, 12, 13, 14:
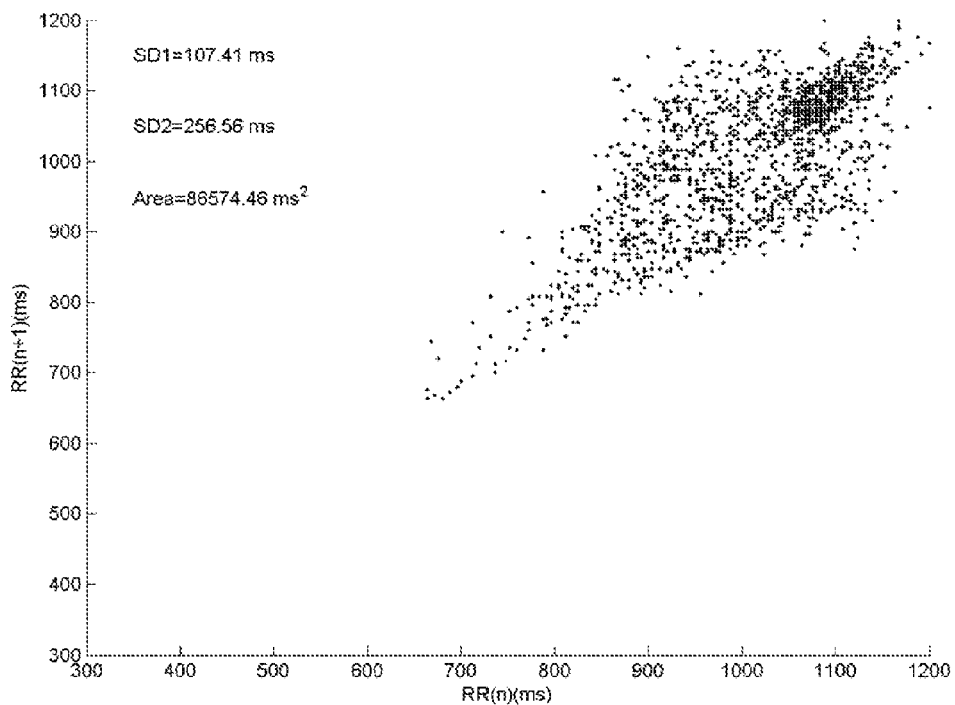
Figures 3, 4, 5, 6, 7, 8, 9, 10, 11, 12, 13, 14, 15:
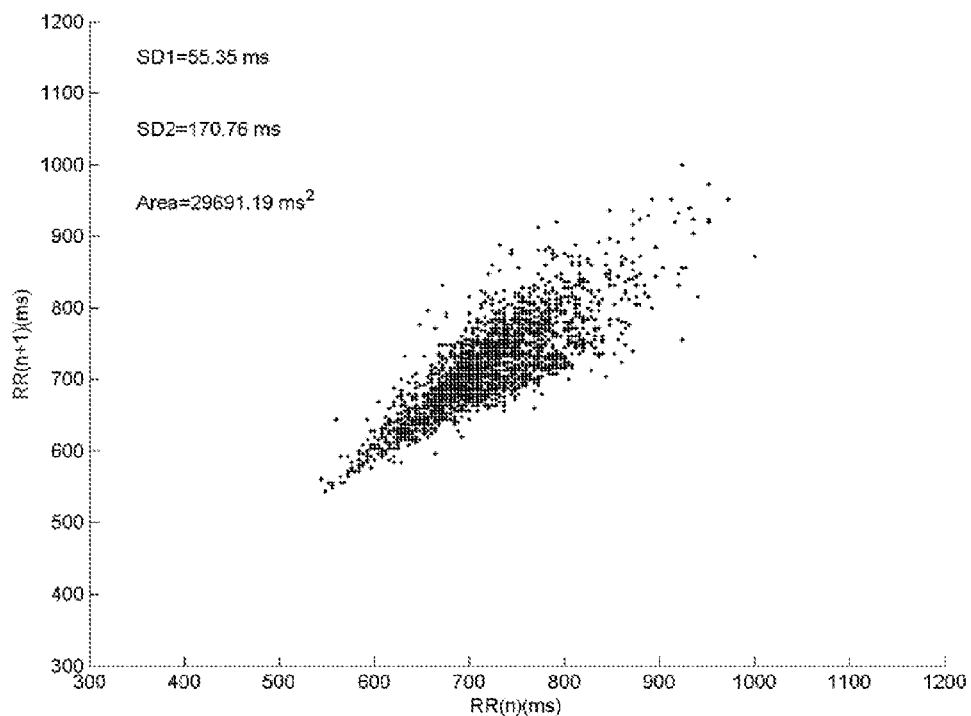
Figures 3, 4, 5, 6, 7, 8, 9, 10, 11, 12, 13, 14, 15, 16:
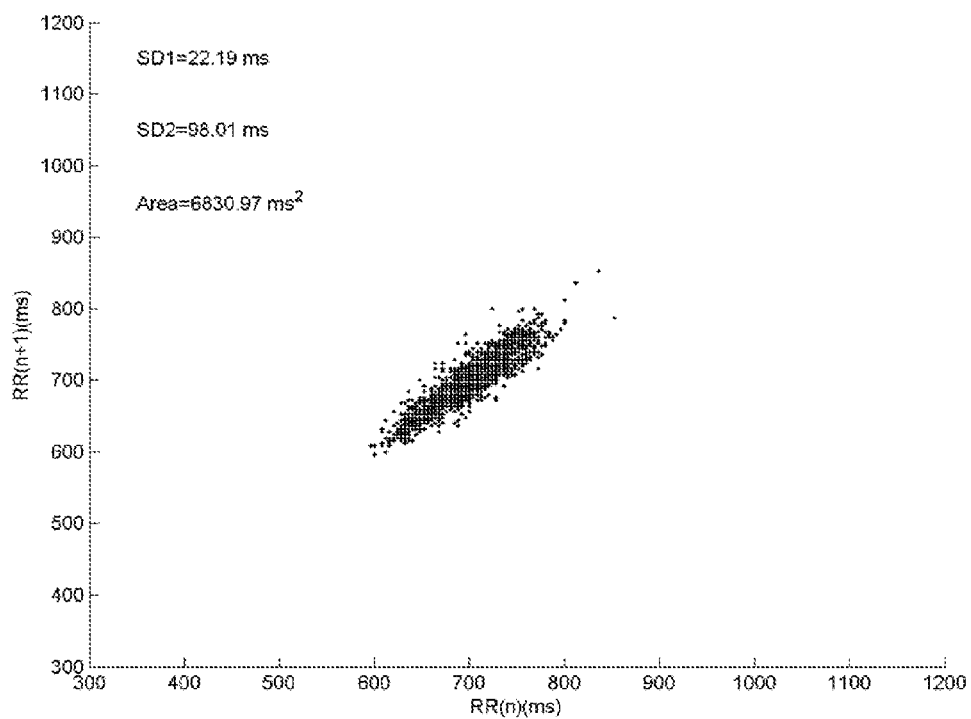
Figures 3, 4, 5, 6, 7, 8, 9, 10, 11, 12, 13, 14, 15, 16, 17:
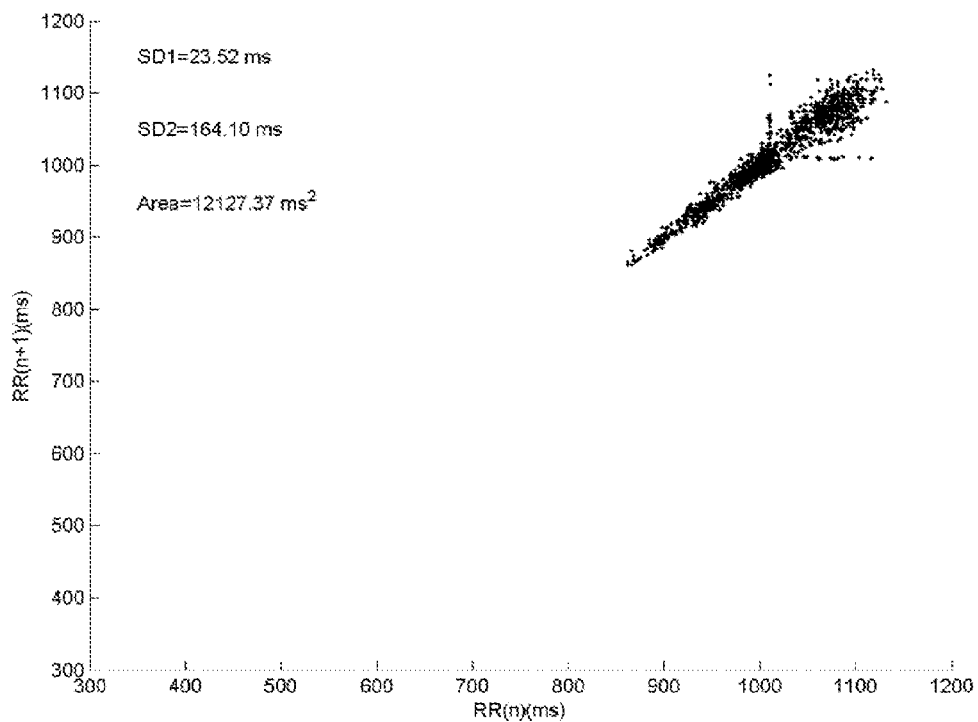
Figures 3, 4, 5, 6, 7, 8, 9, 10, 11, 12, 13, 14, 15, 16, 17, 18:
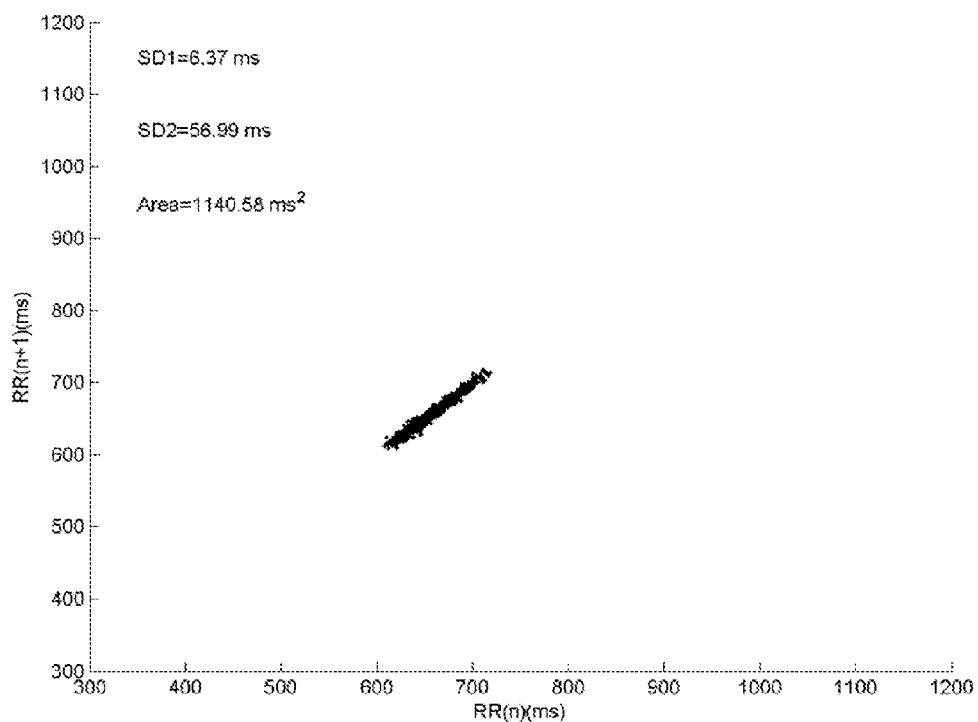
Figures 3, 4, 5, 6, 7, 8, 9, 10, 11, 12, 13, 14, 15, 16, 17, 18, 19:
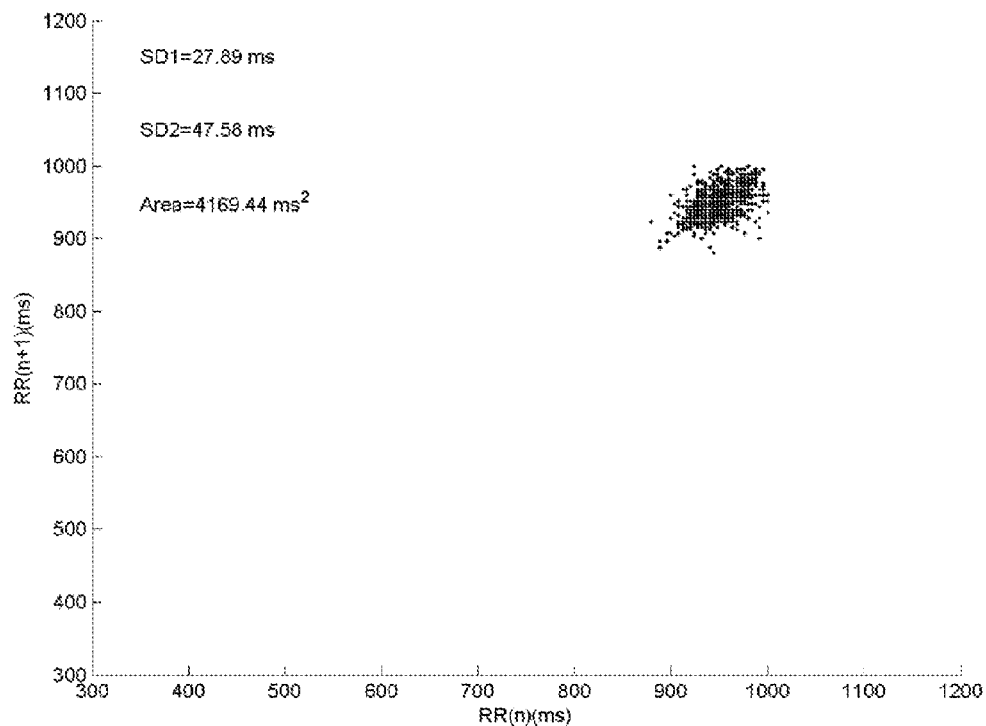
Figures 3, 4, 5, 6, 7, 8, 9, 10, 11, 12, 13, 14, 15, 16, 17, 18, 19, 20:
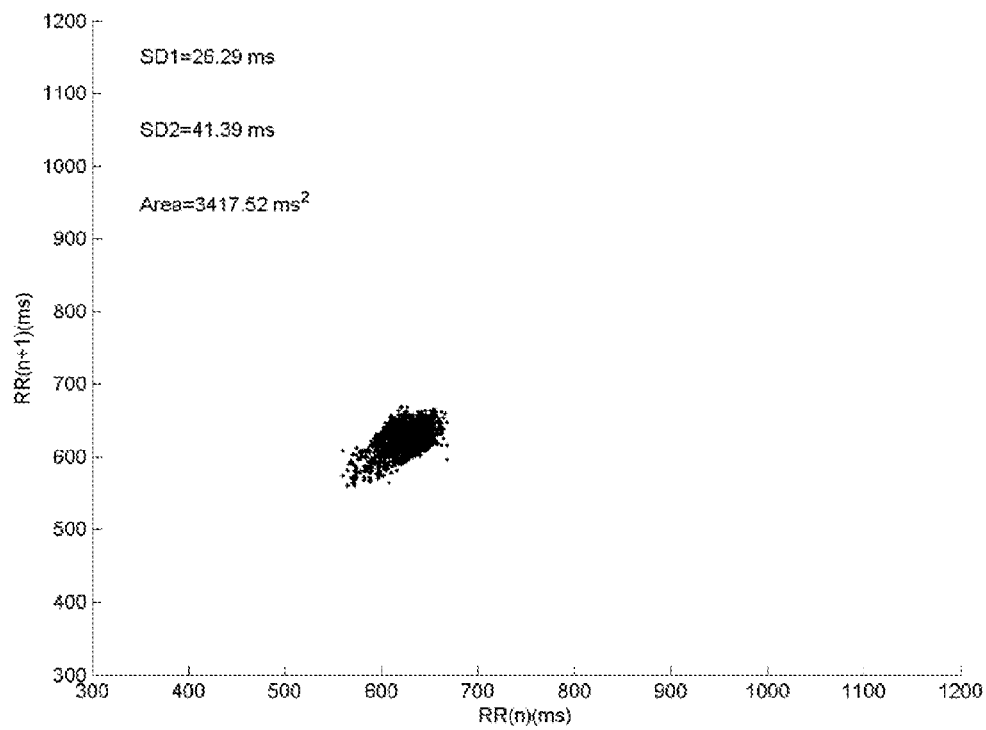
Figures 3, 4, 5, 6, 7, 8, 9, 10, 11, 12, 13, 14, 15, 16, 17, 18, 19, 20, 21:
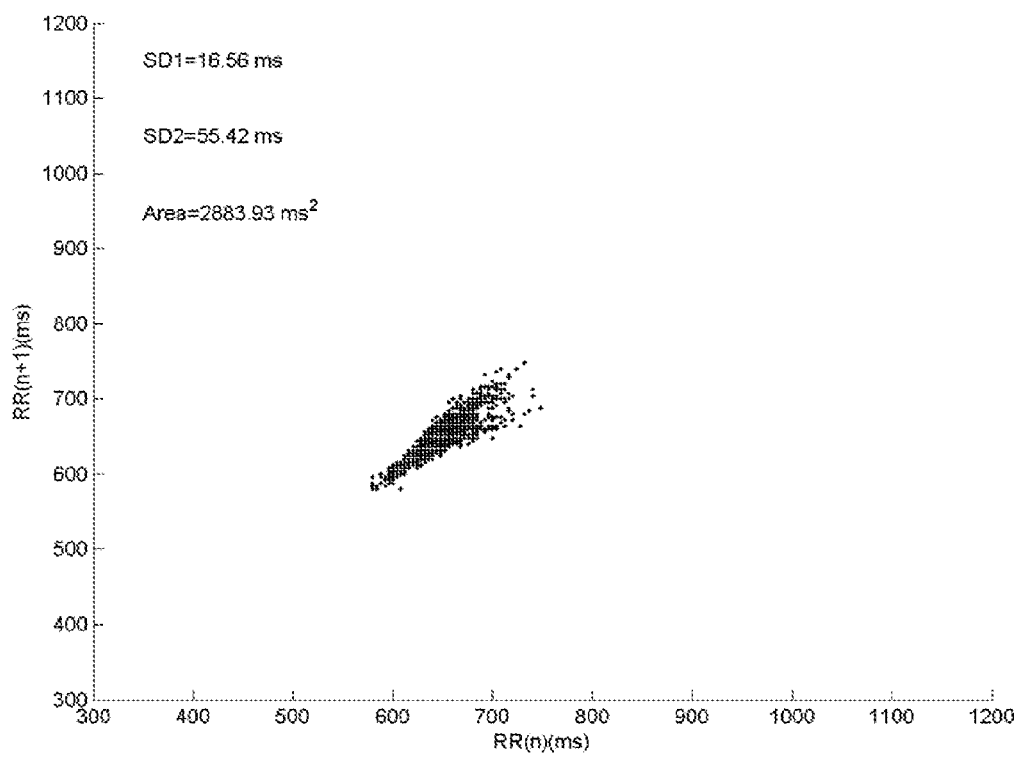
Figures 3, 4, 5, 6, 7, 8, 9, 10, 11, 12, 13, 14, 15, 16, 17, 18, 19, 20, 21, 22:
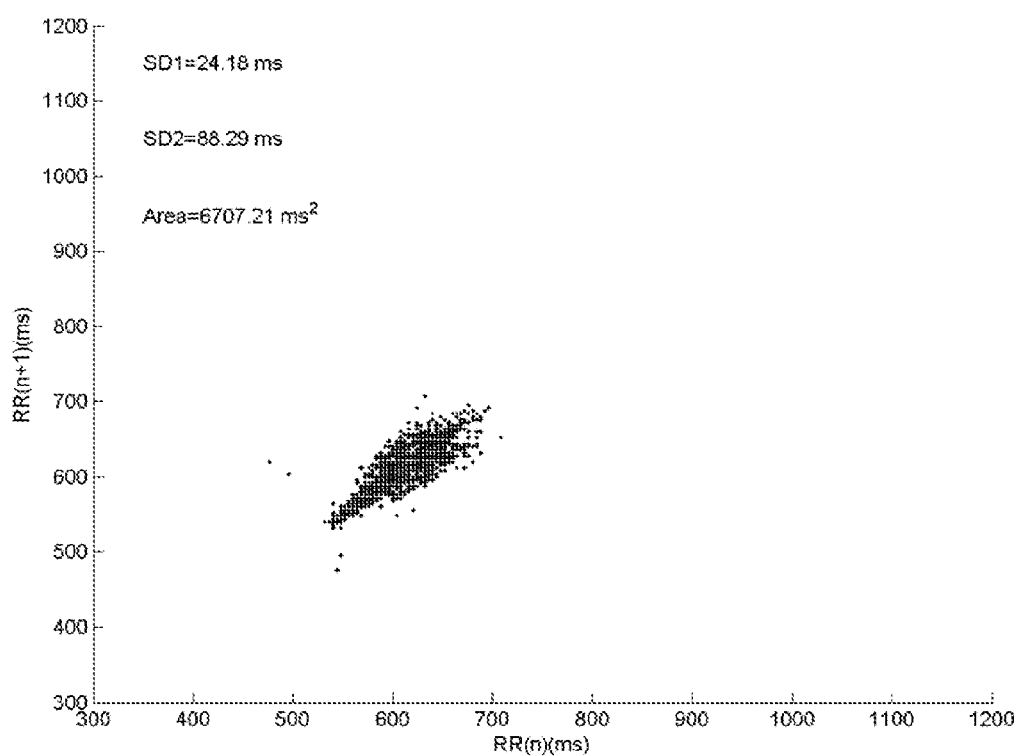
Figures 3, 4, 5, 6, 7, 8, 9, 10, 11, 12, 13, 14, 15, 16, 17, 18, 19, 20, 21, 22, 23:
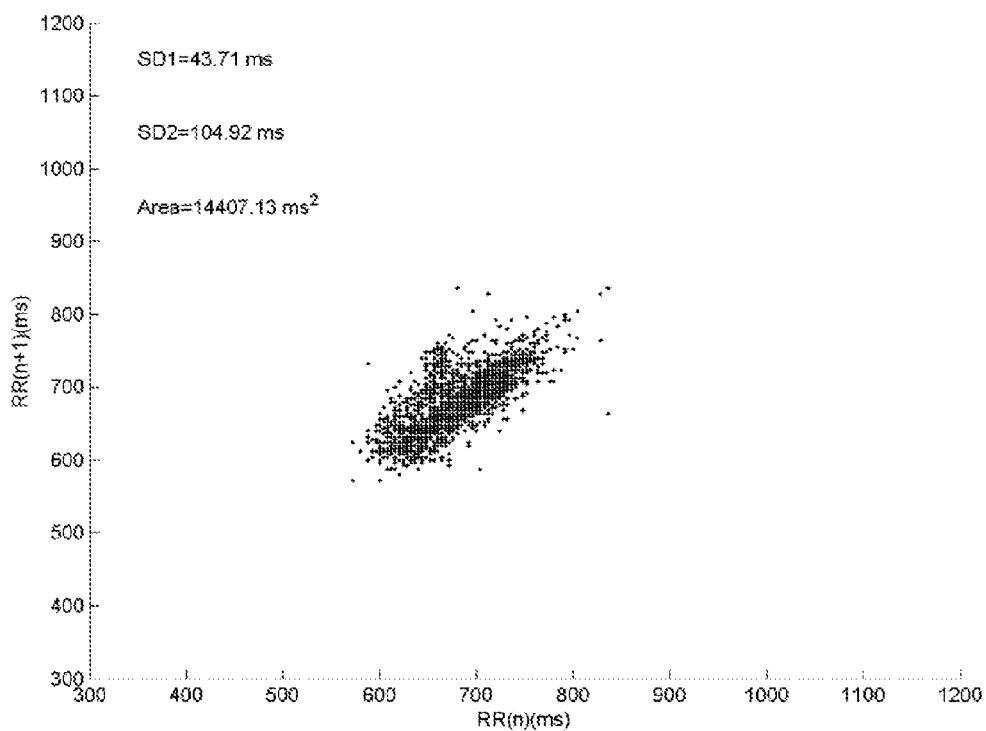
Figures 3, 4, 5, 6, 7, 8, 9, 10, 11, 12, 13, 14, 15, 16, 17, 18, 19, 20, 21, 22, 23, 24:
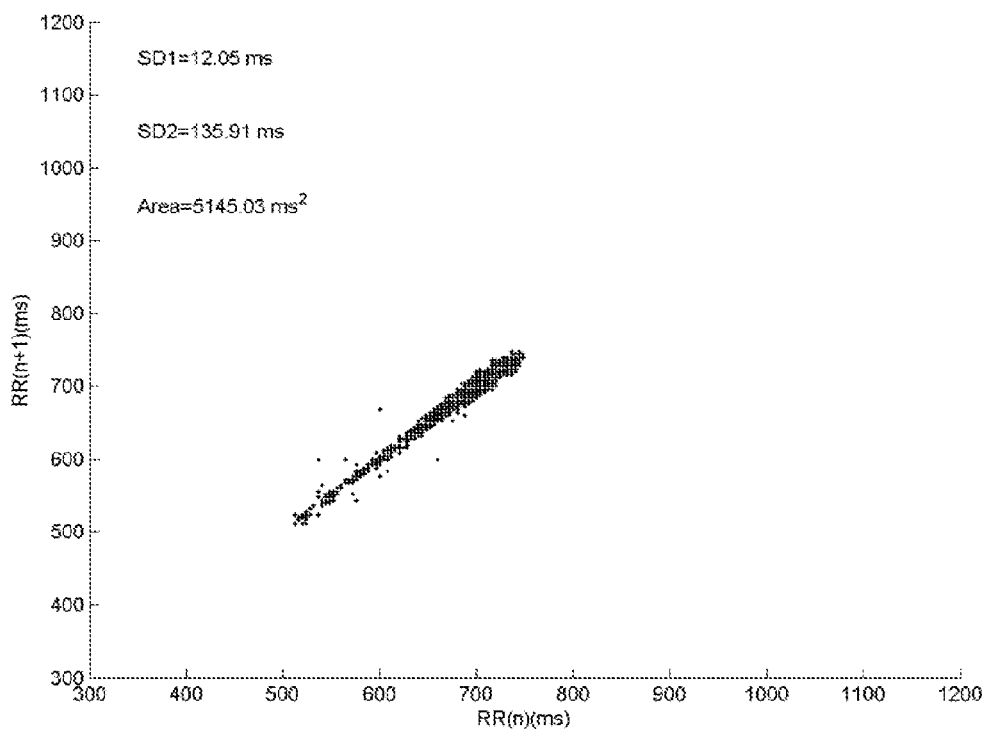
Figures 3, 4, 5, 6, 7, 8, 9, 10, 11, 12, 13, 14, 15, 16, 17, 18, 19, 20, 21, 22, 23, 24, 25:
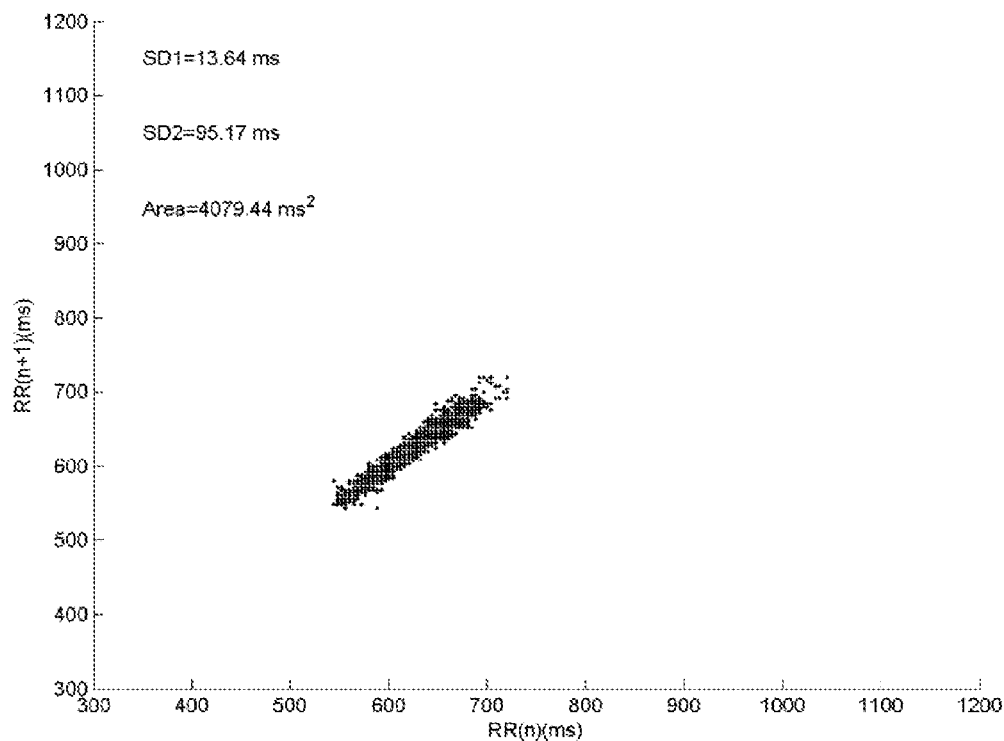
Figures 3, 4, 5, 6, 7, 8, 9, 10, 11, 12, 13, 14, 15, 16, 17, 18, 19, 20, 21, 22, 23, 24, 25, 26:
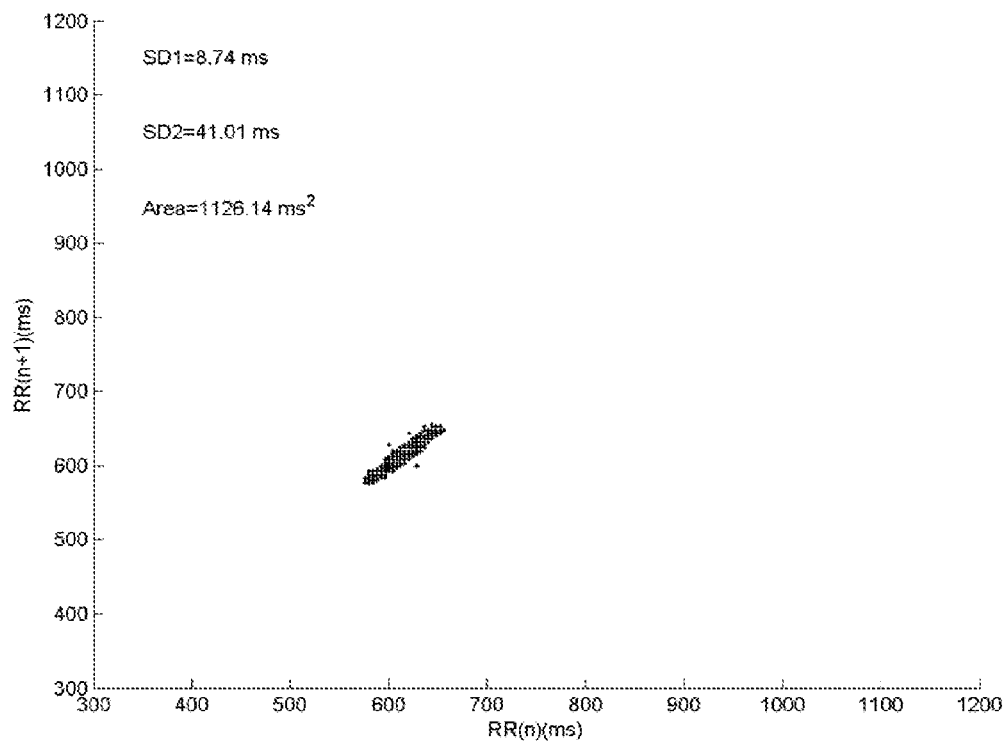
Figures 3, 4, 5, 6, 7, 8, 9, 10, 11, 12, 13, 14, 15, 16, 17, 18, 19, 20, 21, 22, 23, 24, 25, 26, 27:
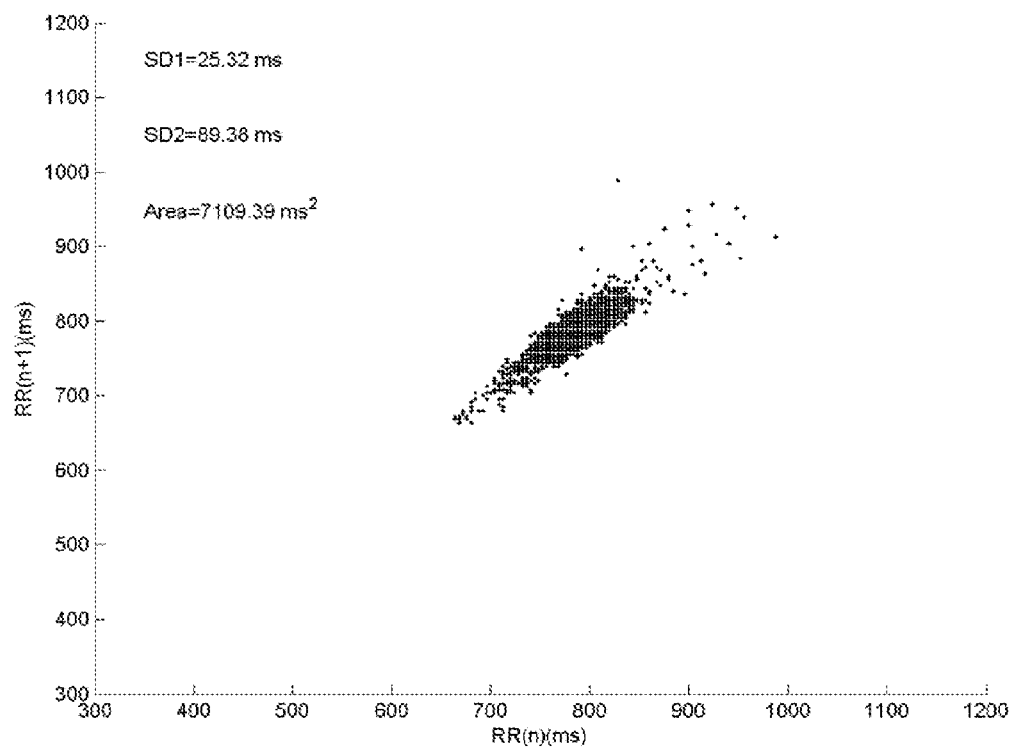
Figures 3, 4, 5, 6, 7, 8, 9, 10, 11, 12, 13, 14, 15, 16, 17, 18, 19, 20, 21, 22, 23, 24, 25, 26, 27, 28:
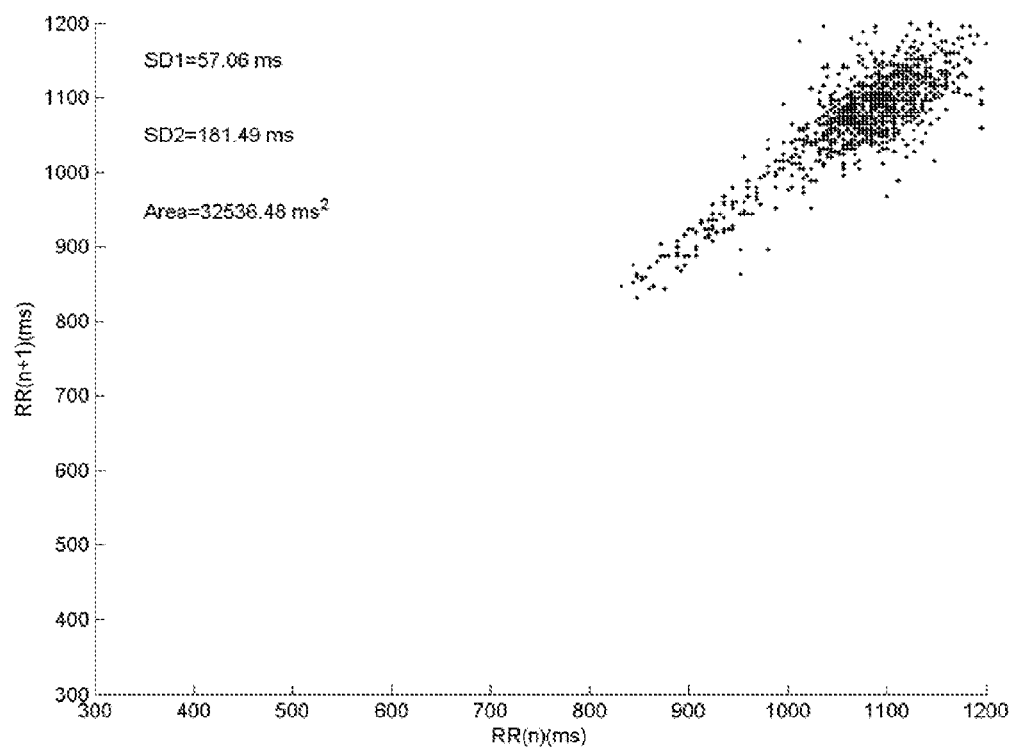
Figures 3, 4, 5, 6, 7, 8, 9, 10, 11, 12, 13, 14, 15, 16, 17, 18, 19, 20, 21, 22, 23, 24, 25, 26, 27, 28, 29:
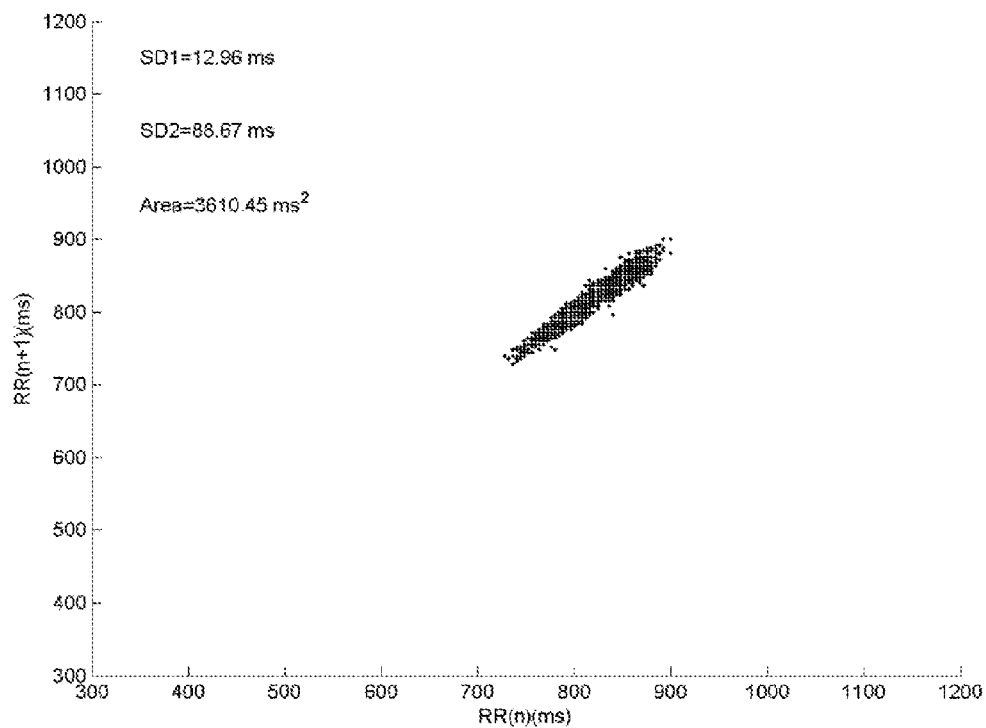
Figures 3, 4, 5, 6, 7, 8, 9, 10, 11, 12, 13, 14, 15, 16, 17, 18, 19, 20, 21, 22, 23, 24, 25, 26, 27, 28, 29, 30:
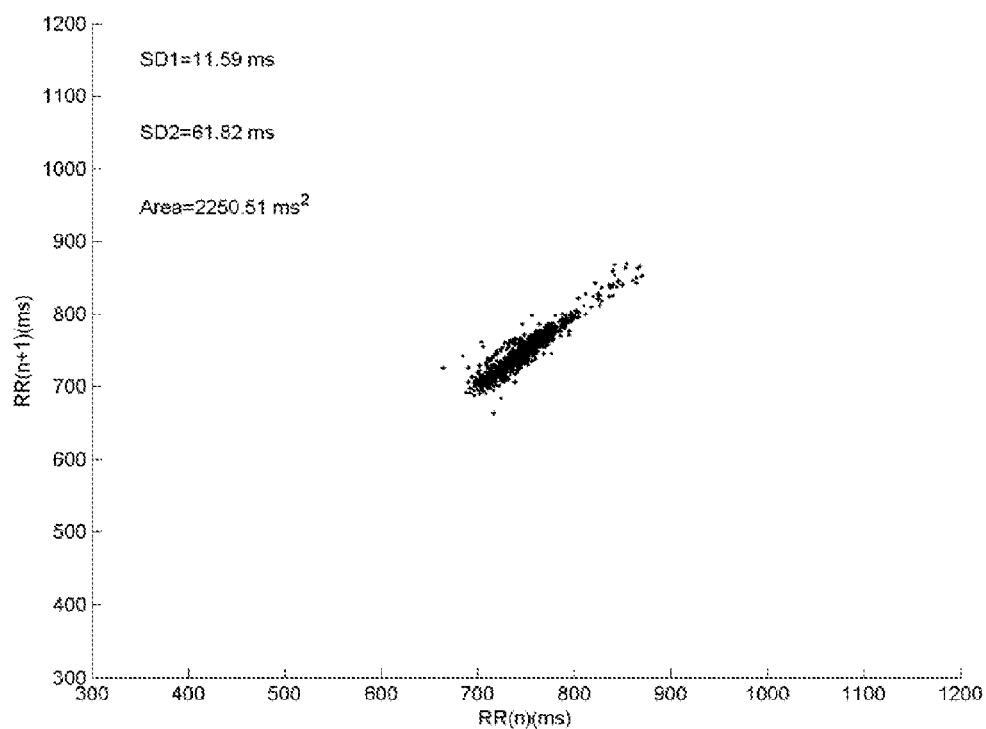
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31:
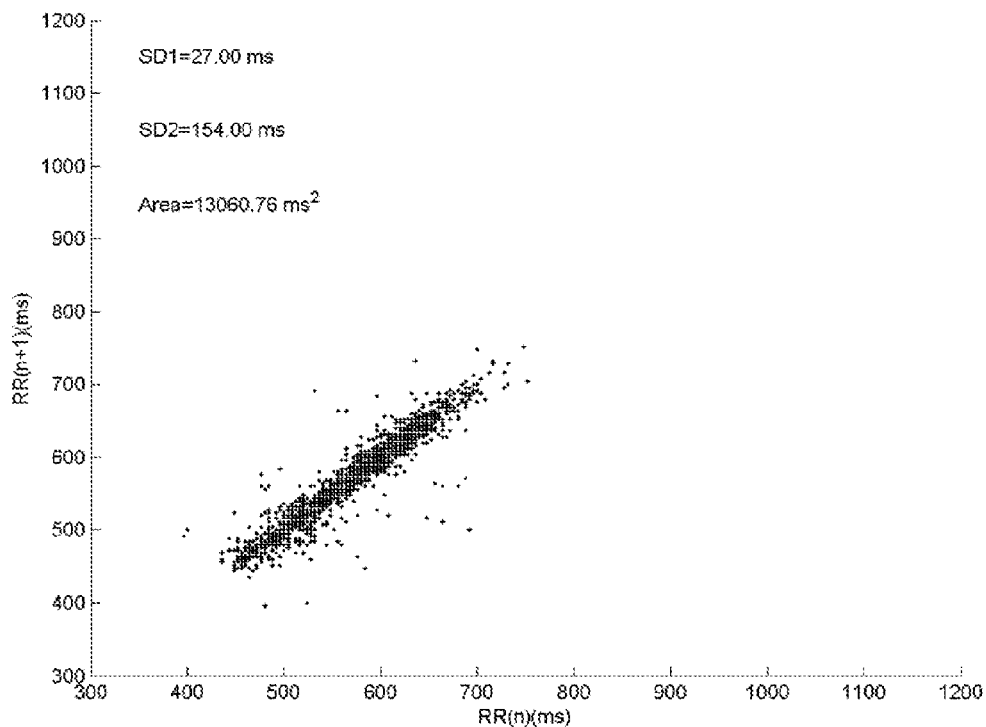
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
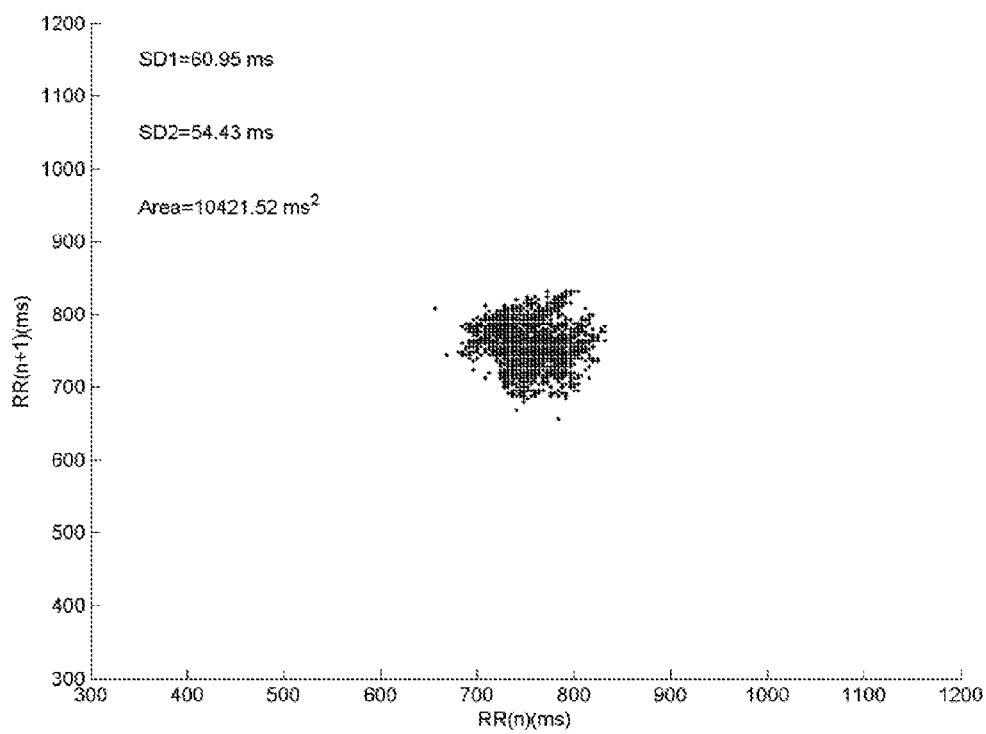
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
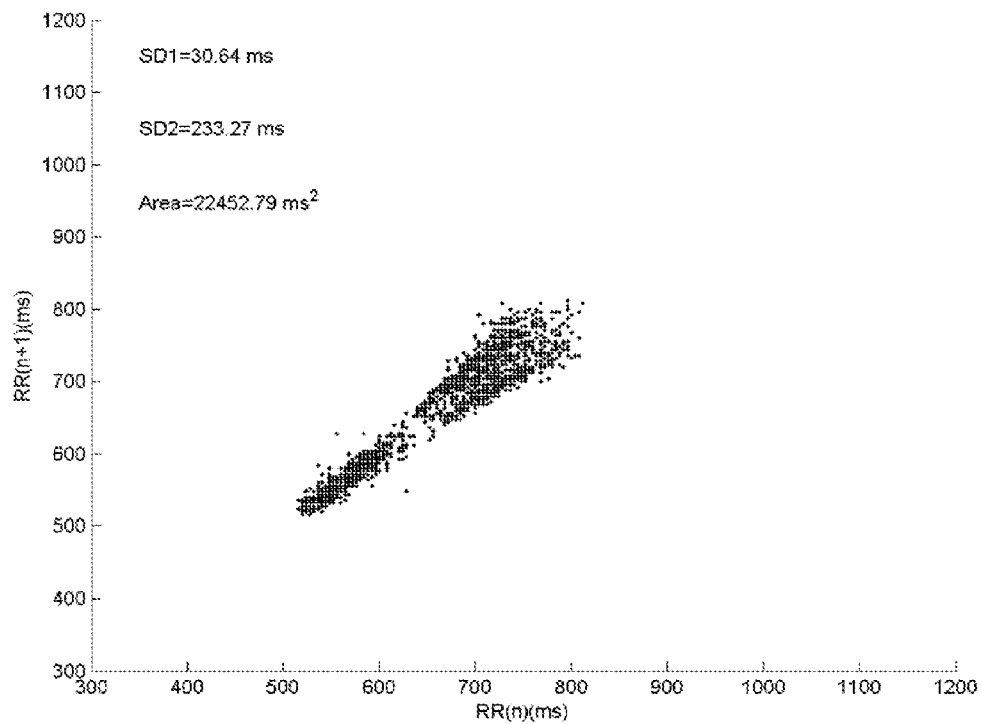
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
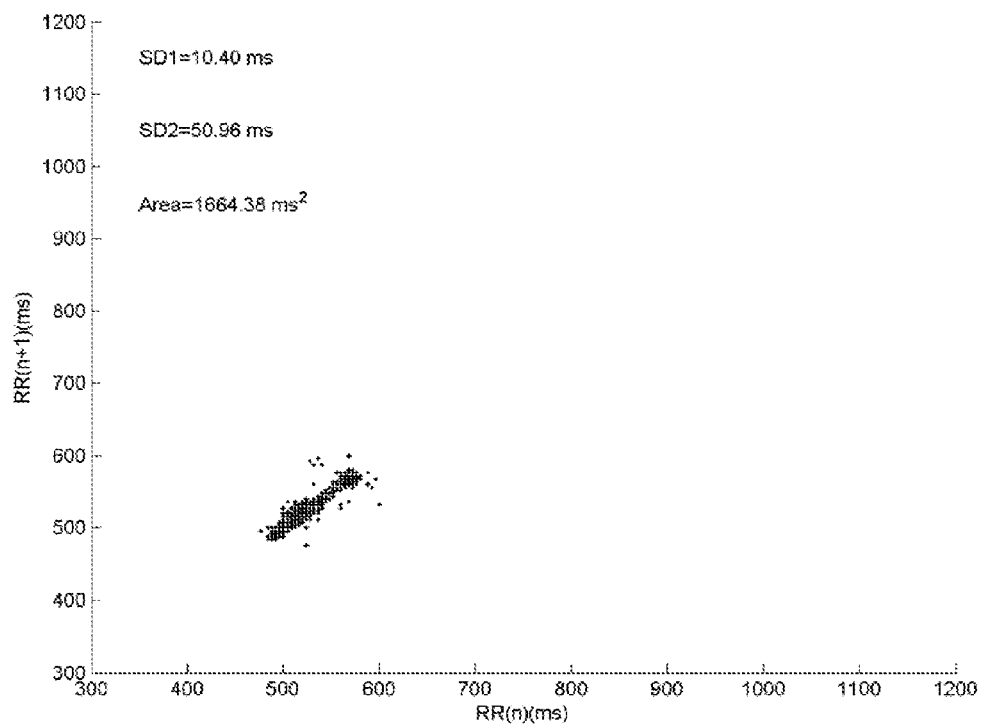
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
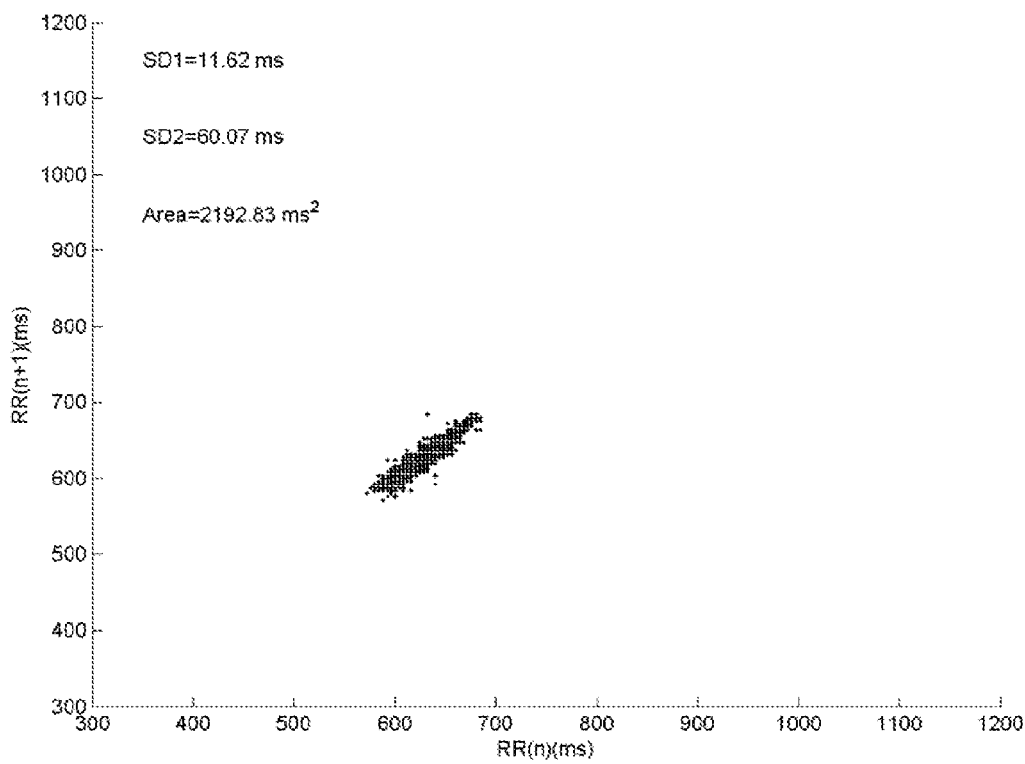
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
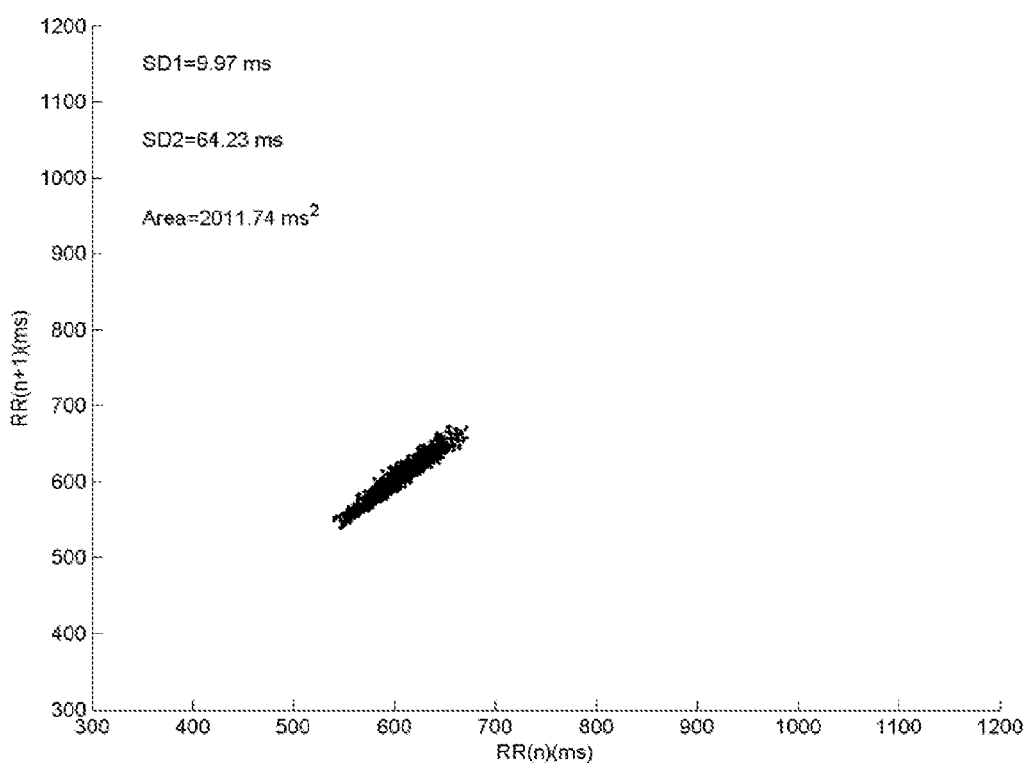
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
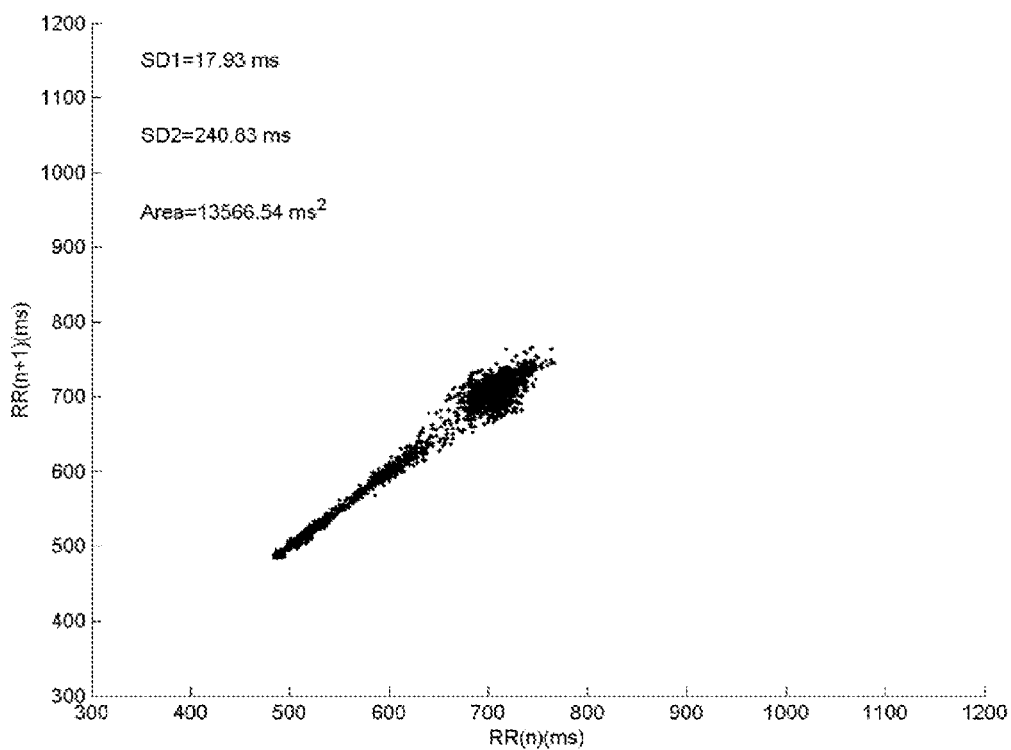
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
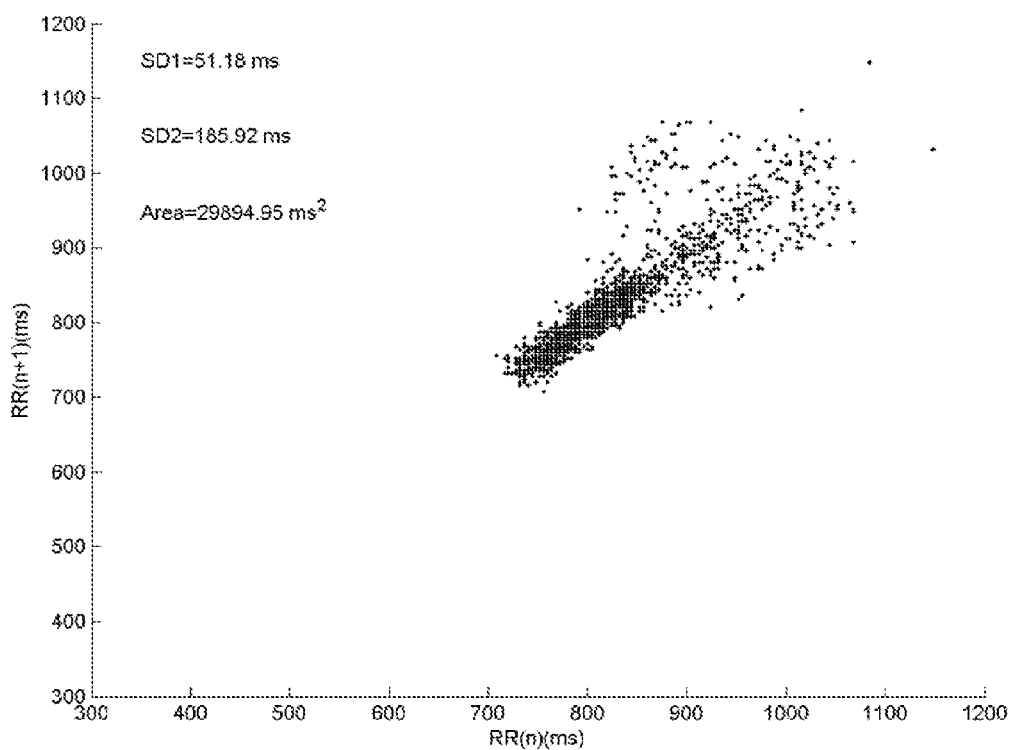
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
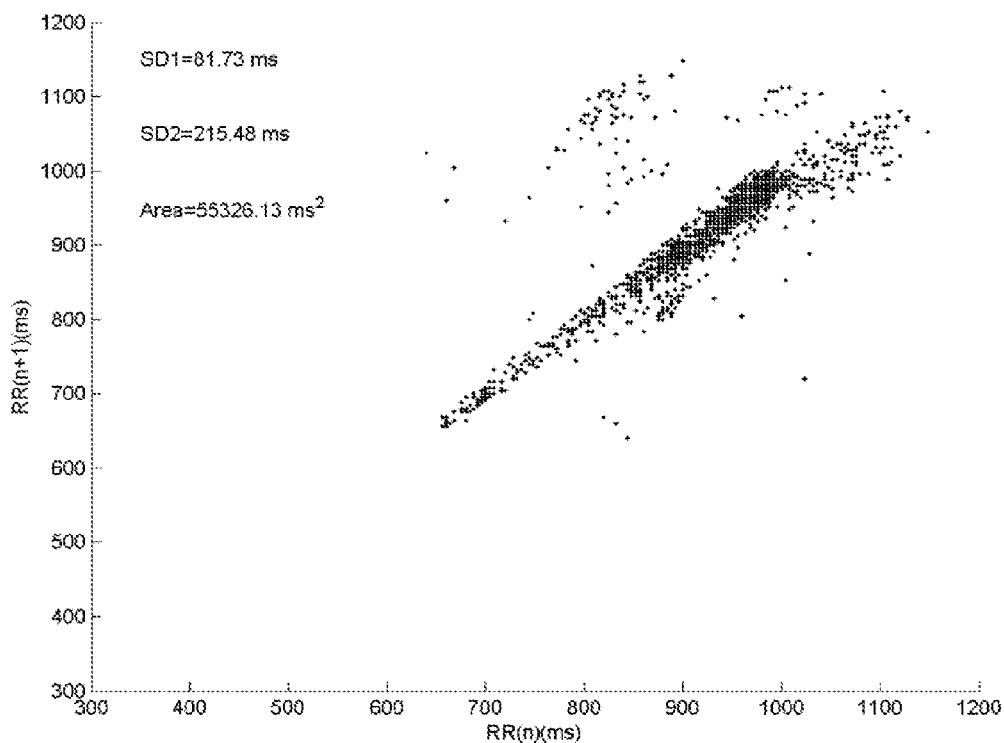
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
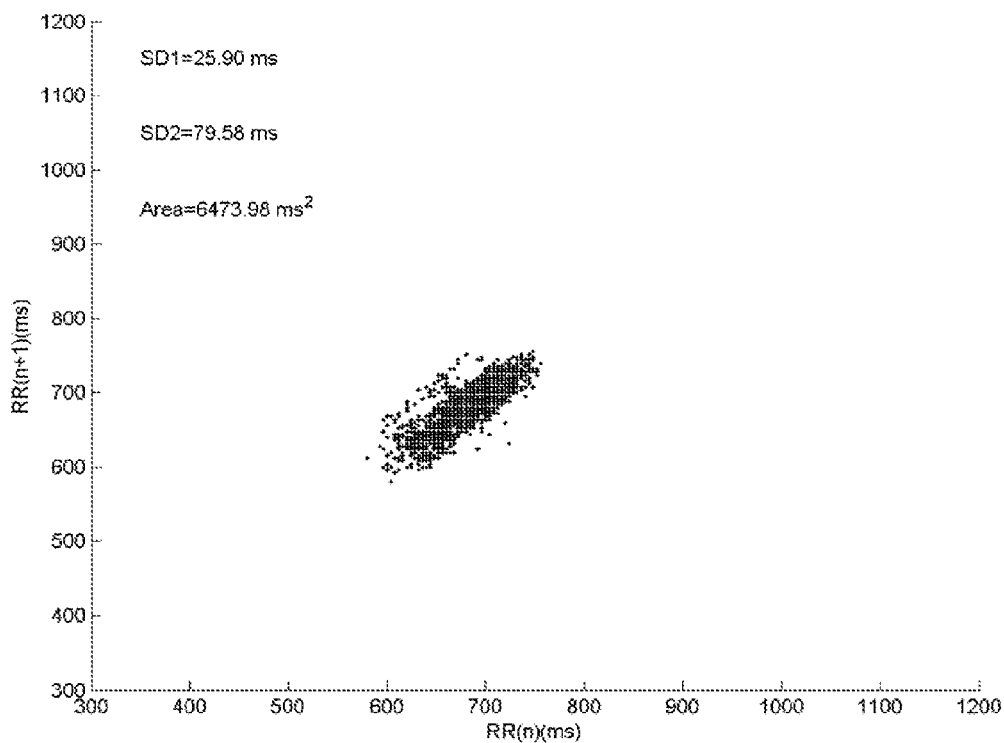
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
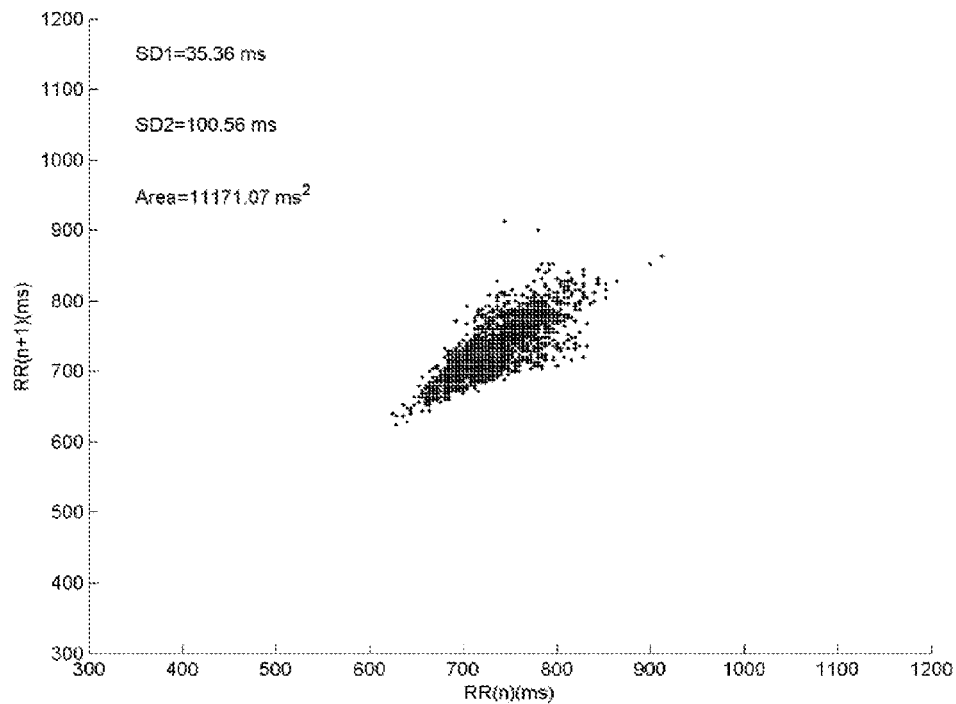
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
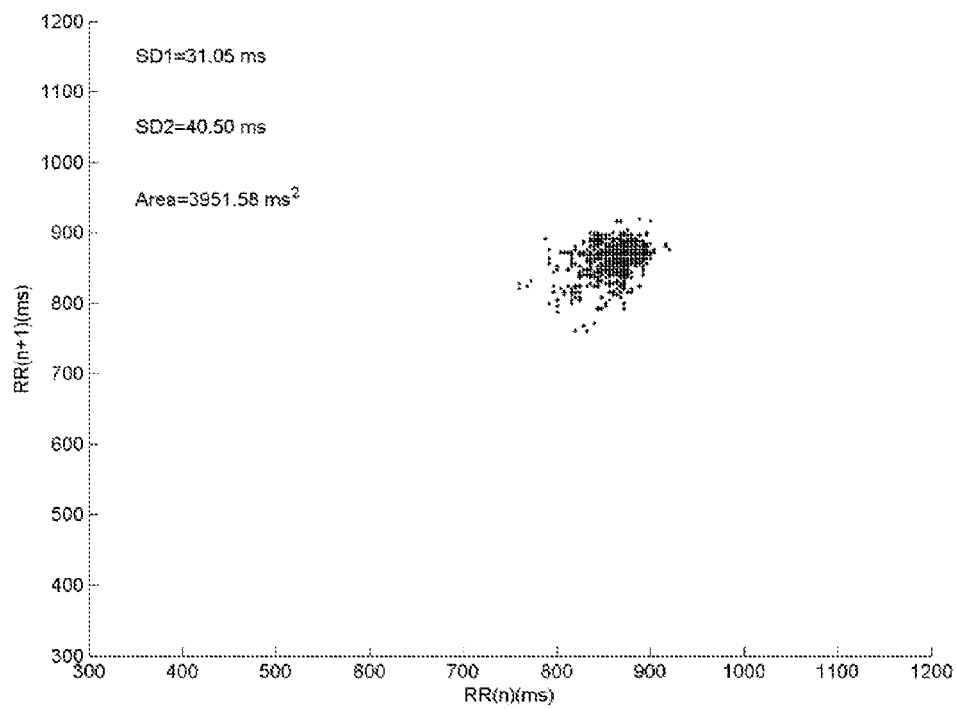
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
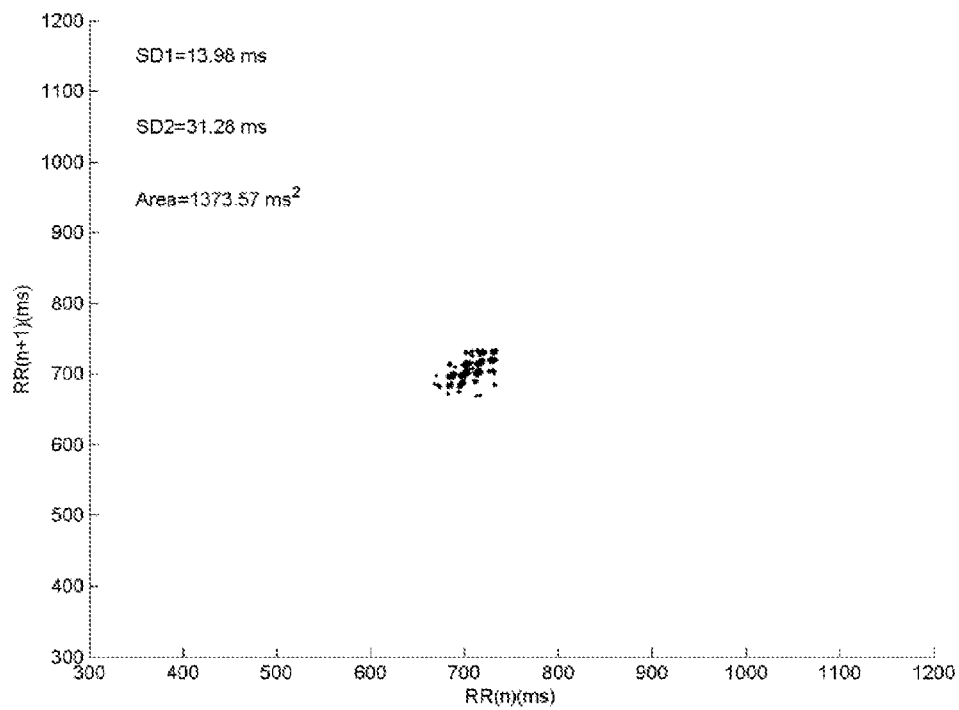
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
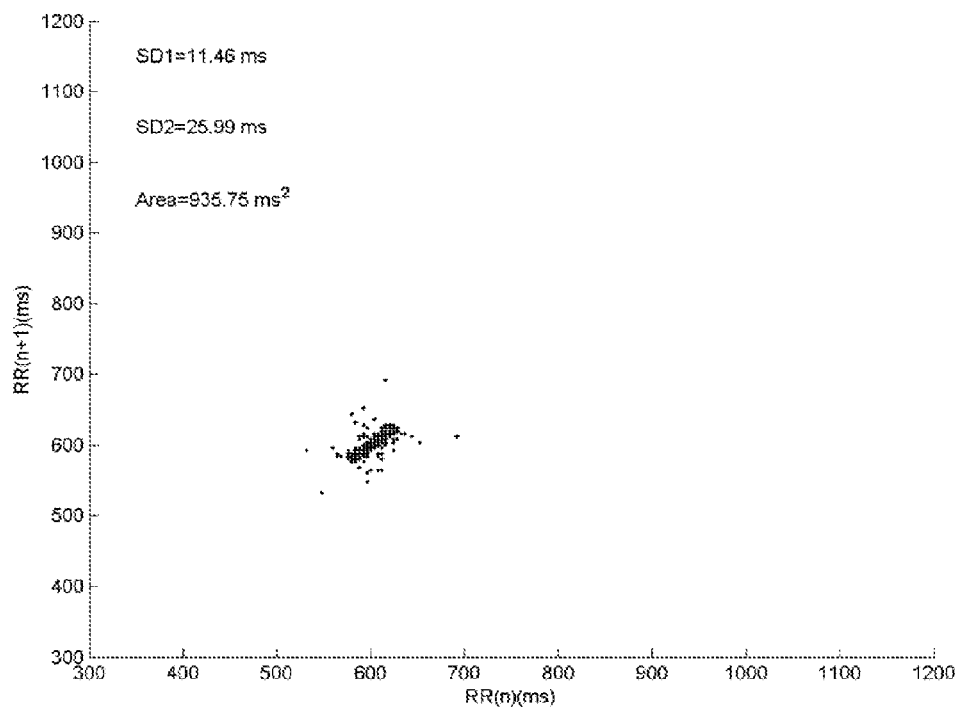
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
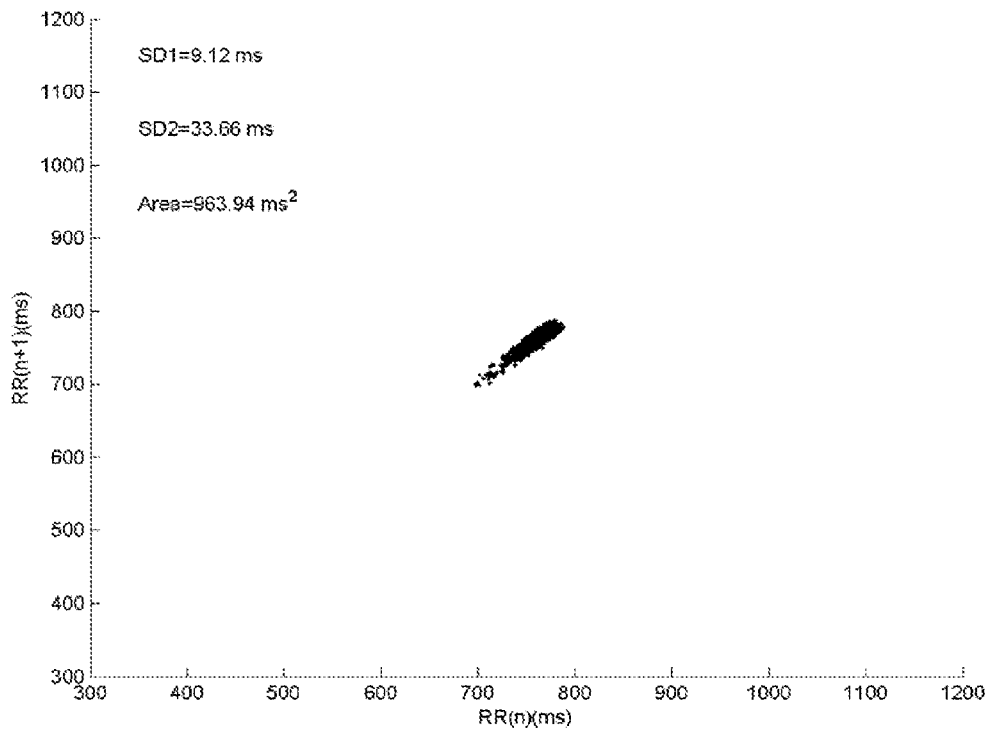
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
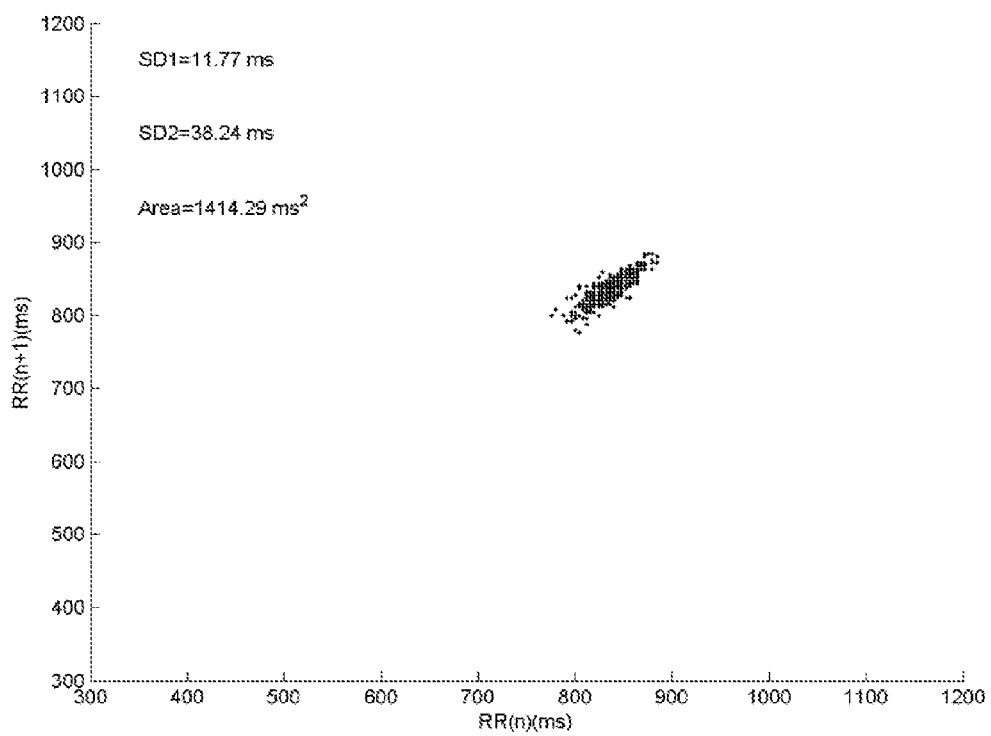
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
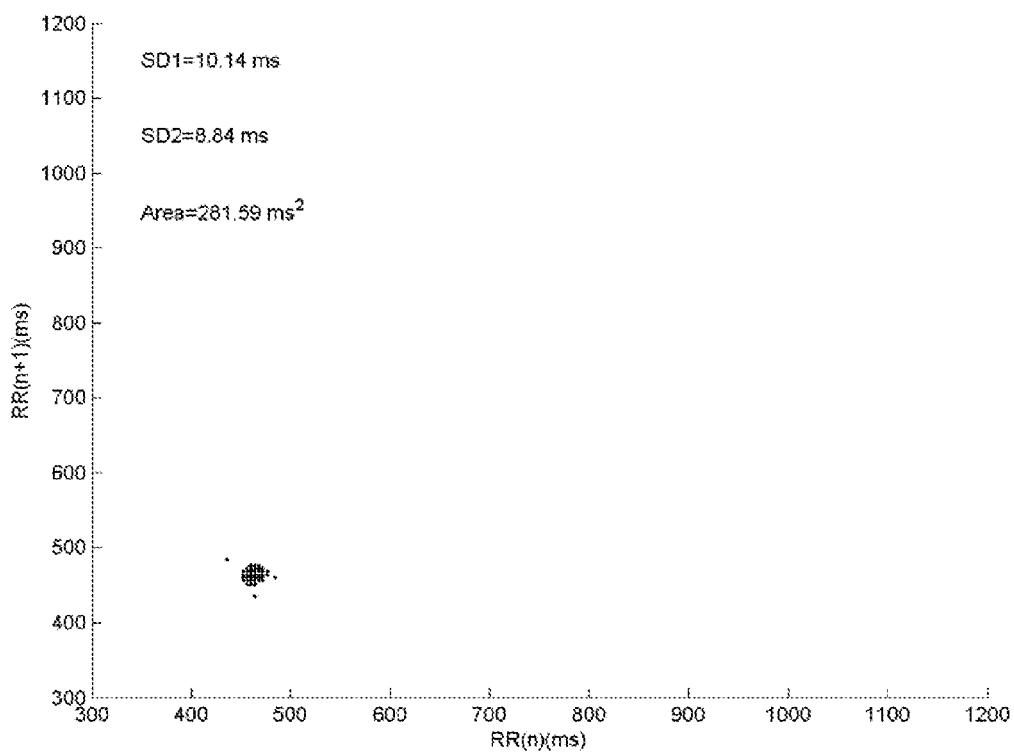
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
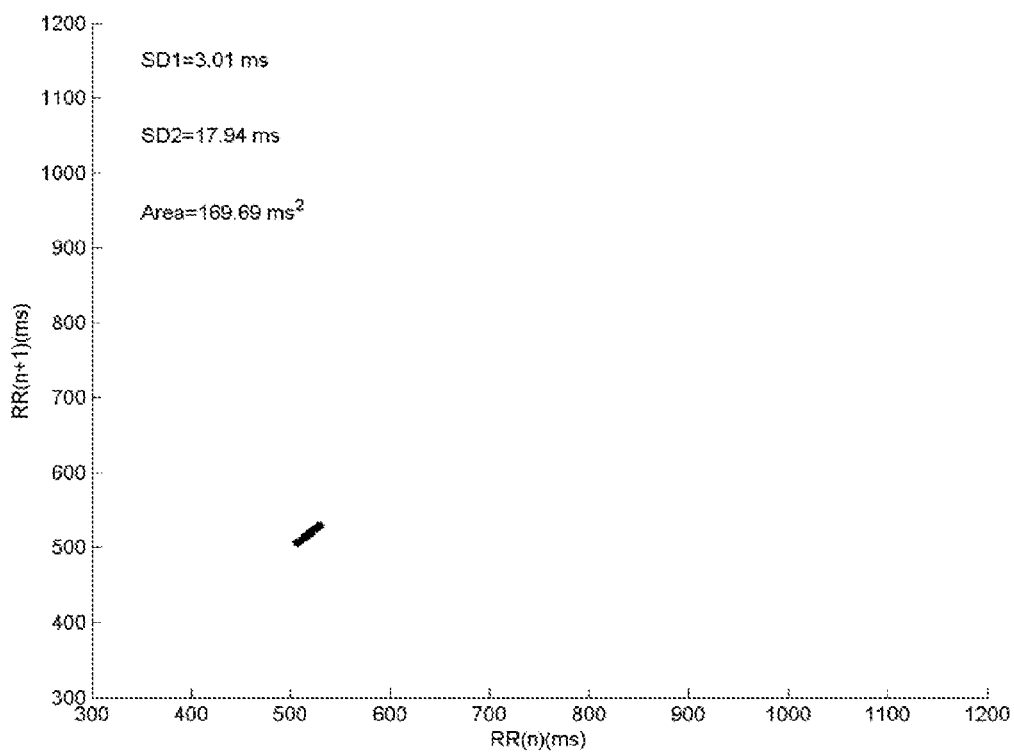
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
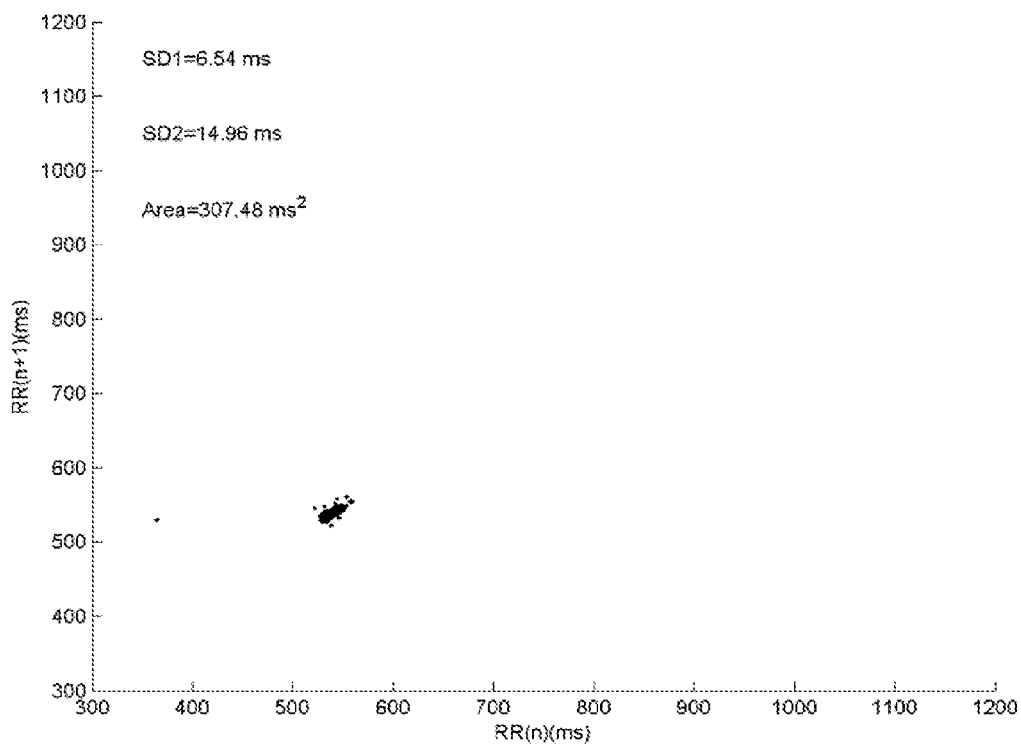
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
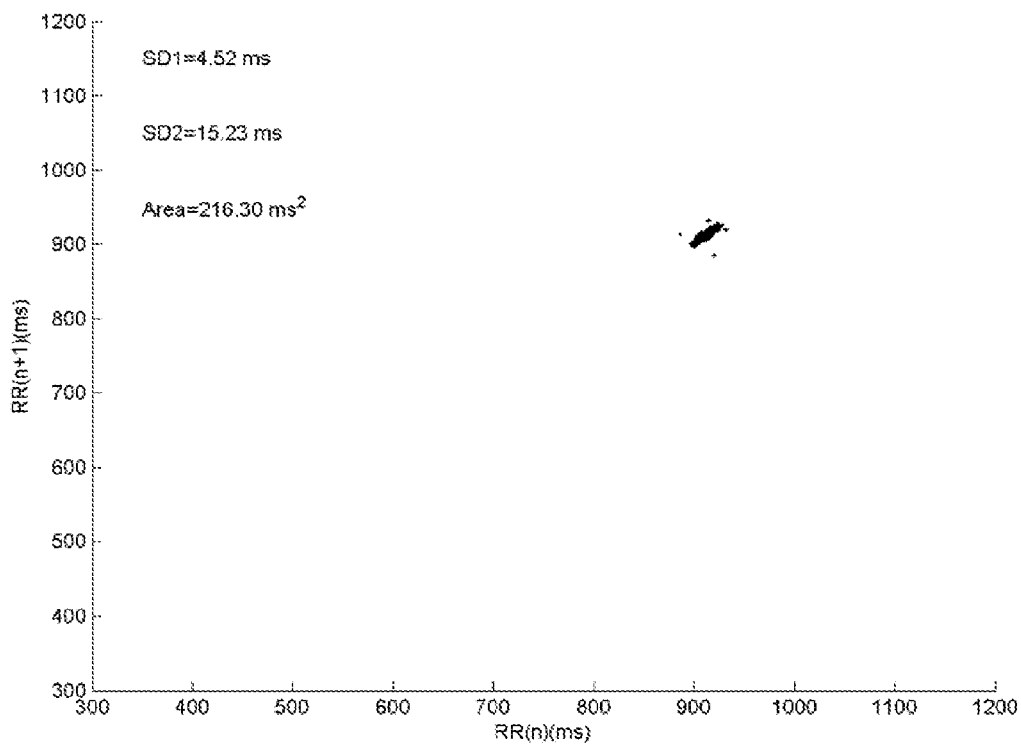
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
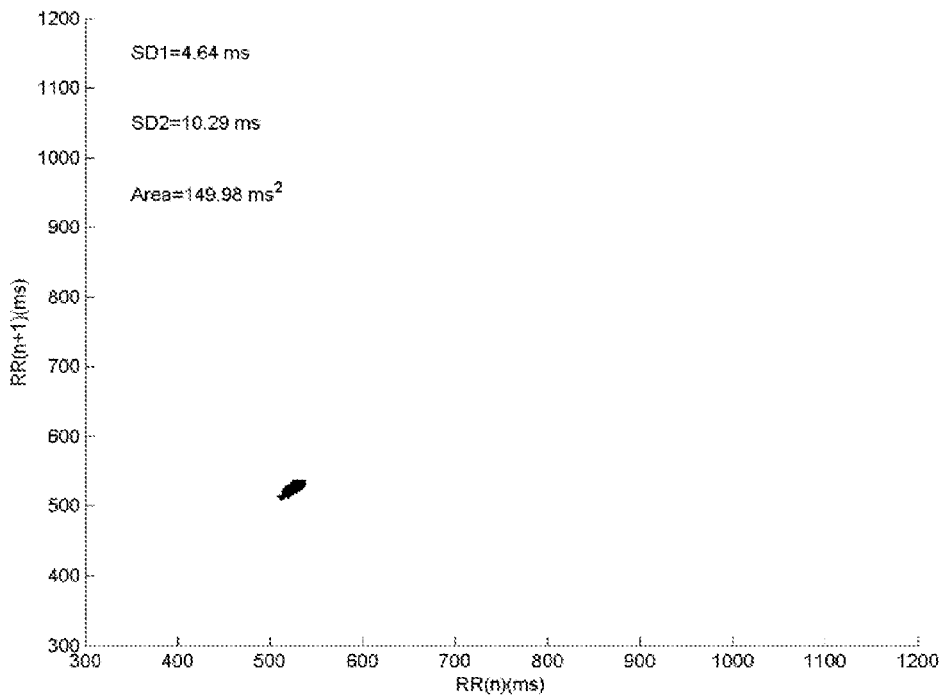
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
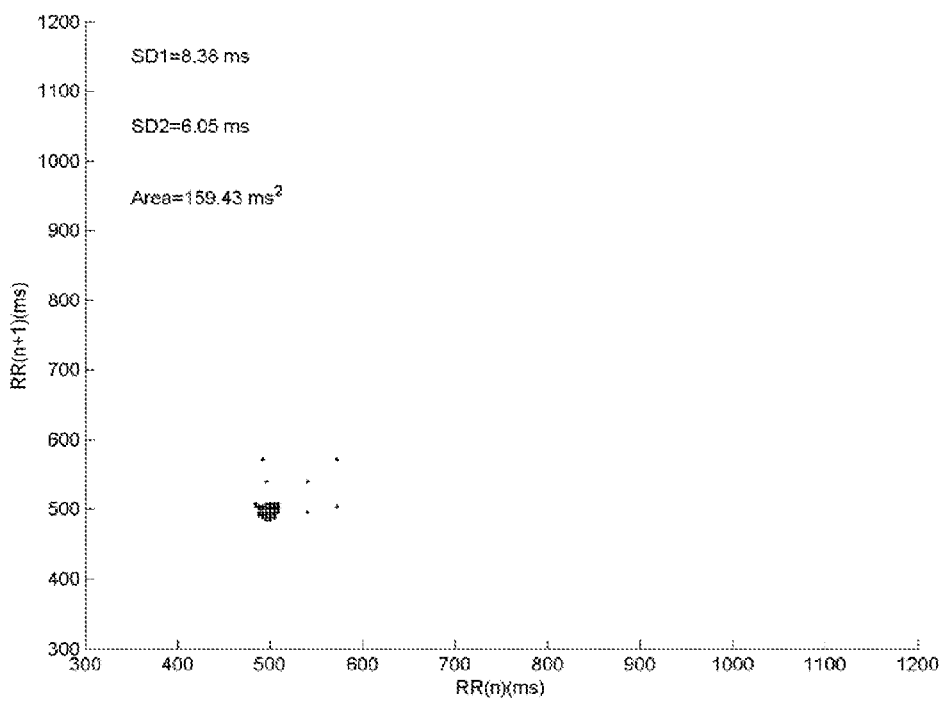
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
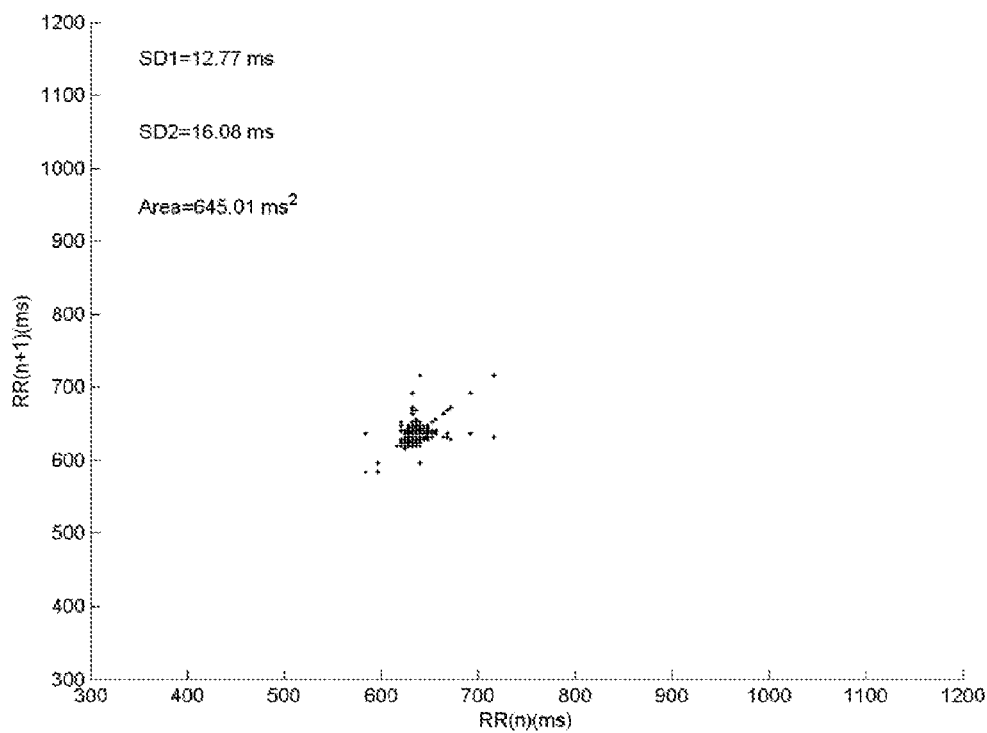
Figures 3, 54:
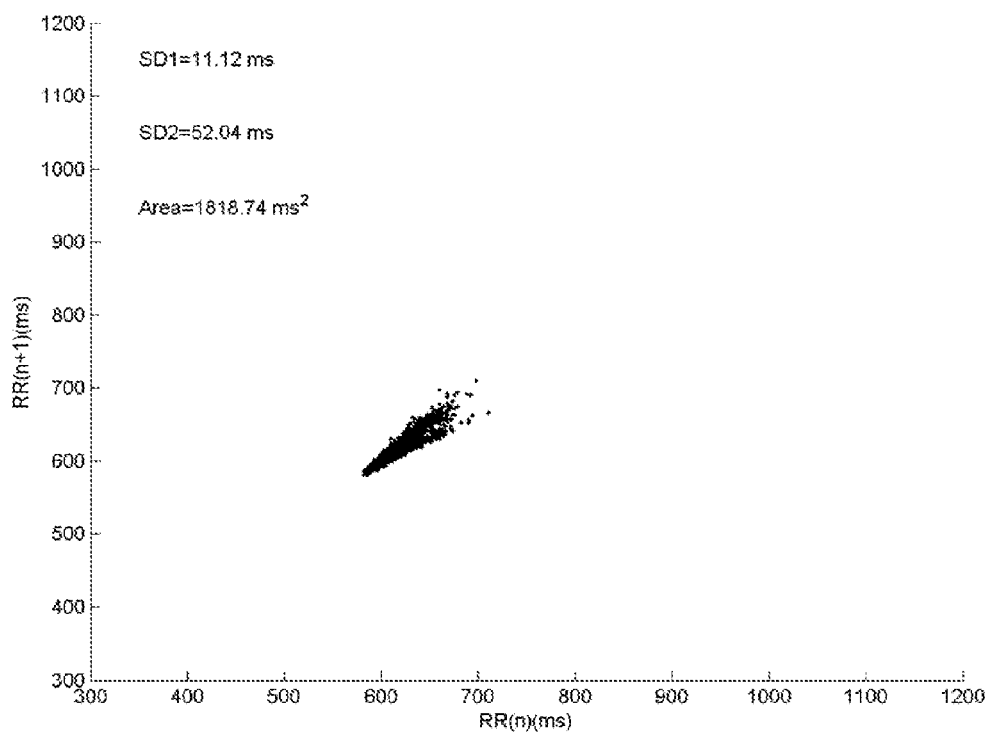
Figures 3, 55:
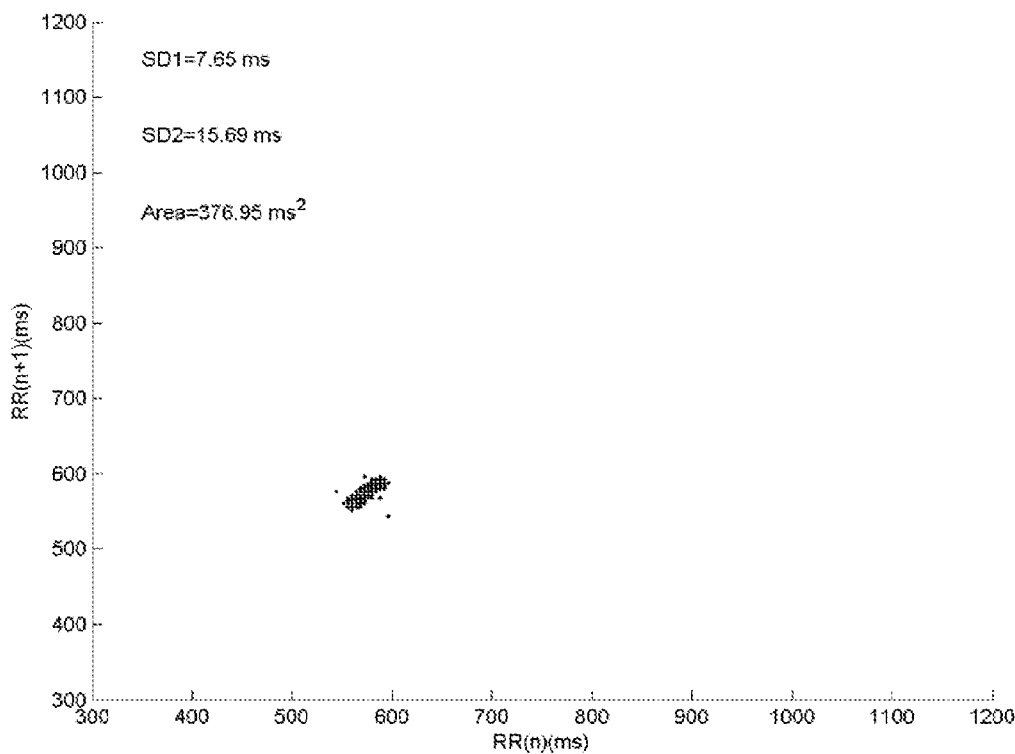
Figures 3, 56:
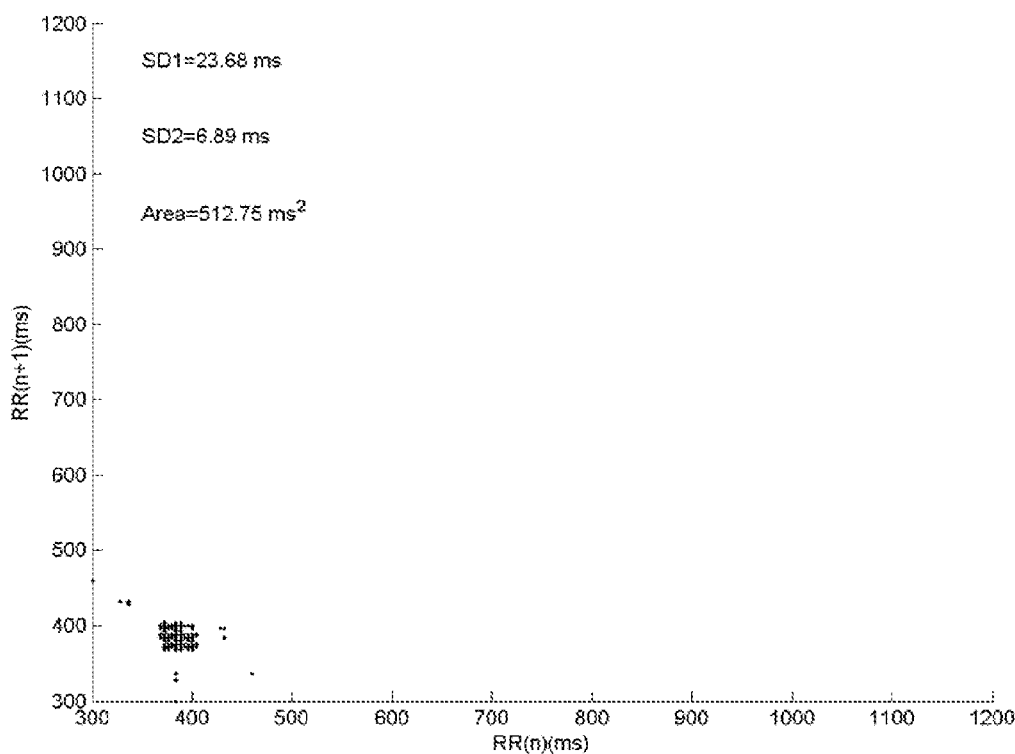
Figures 3, 57:
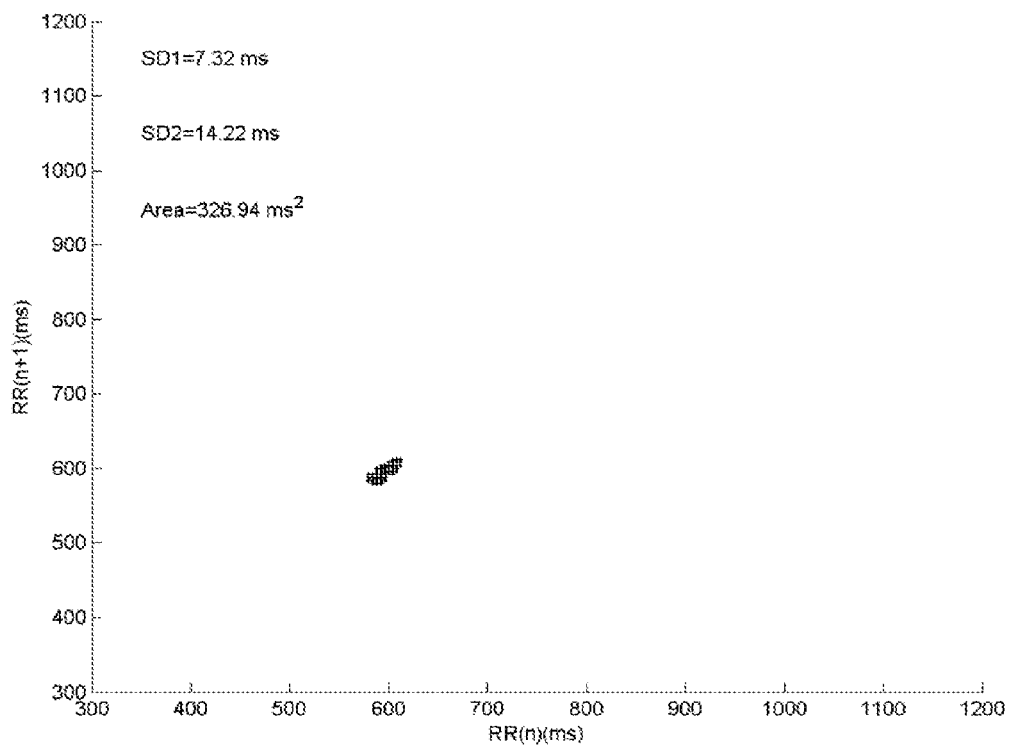
Figures 3, 58:
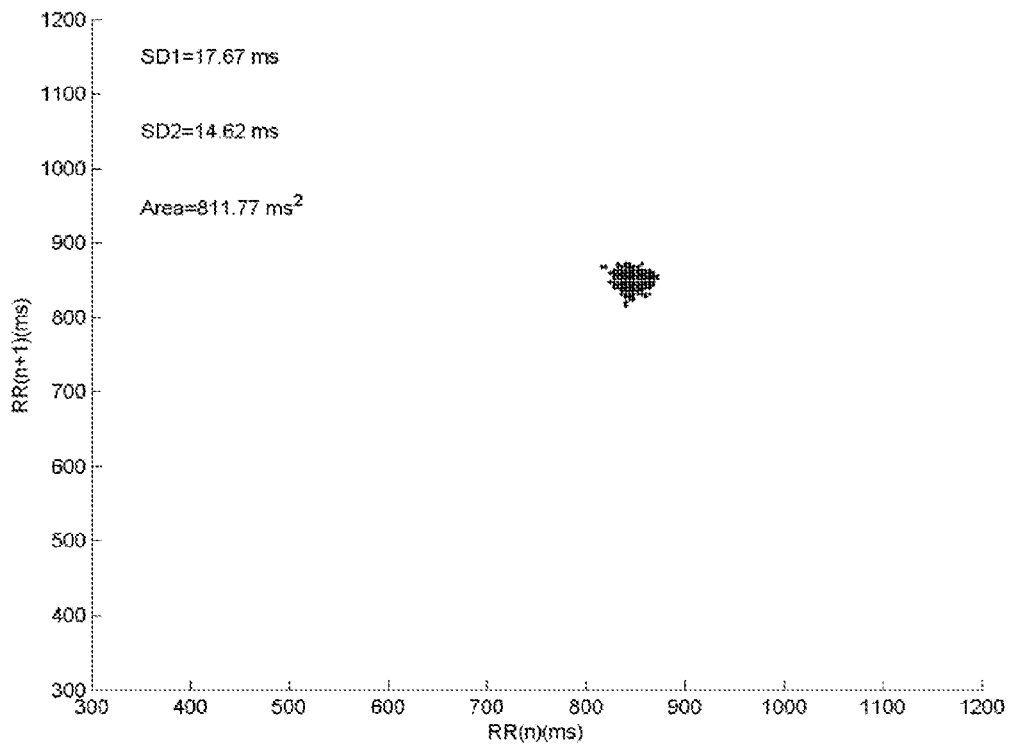
Figure 4:
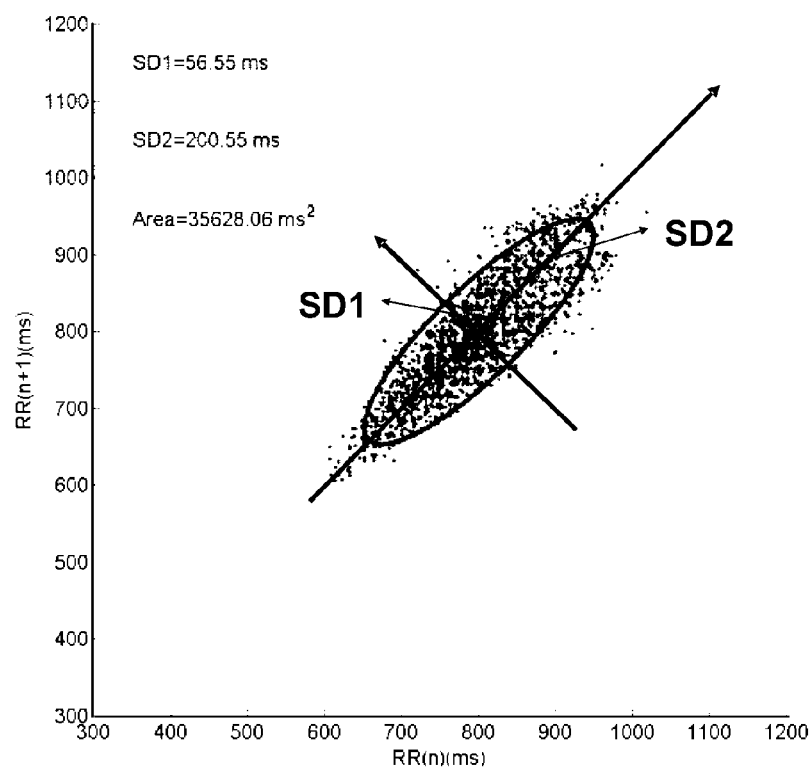
FIG. 4 shows an ellipse fitting of a Poincaré plot.
Figure 5:
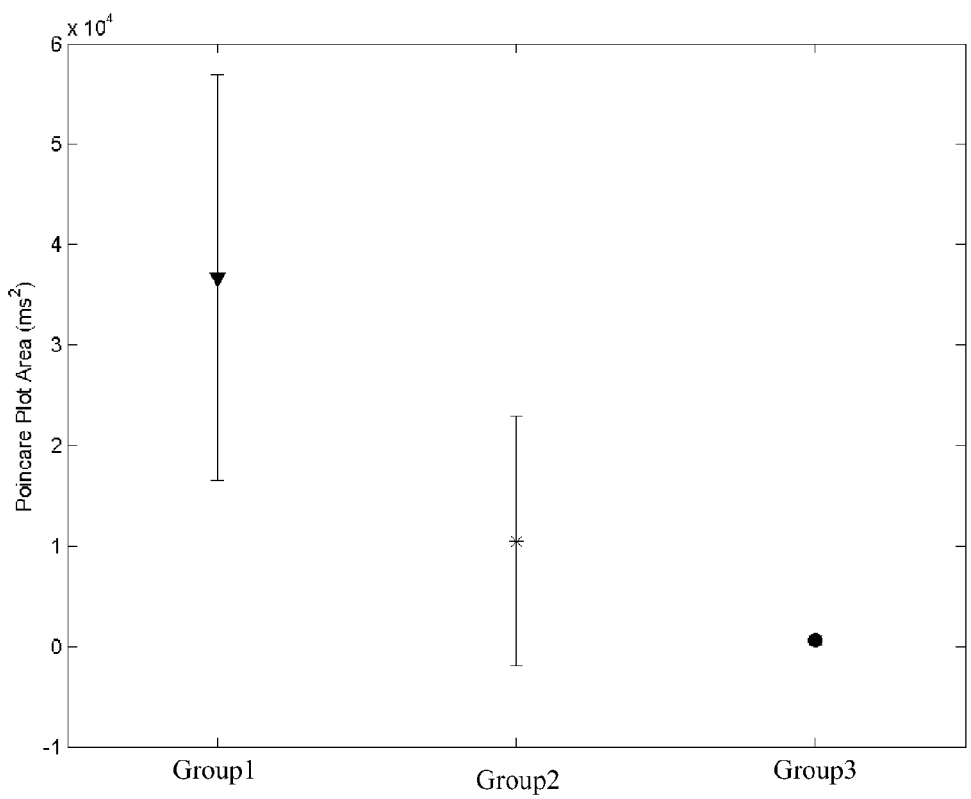
FIG. 5 shows the difference among Poincaré plot area of each group.

FIG. 5 plots Poincaré Area means and standard deviation of each group. It can be found from FIG. 5 and statistical results that there are significant differences in Poincaré plot areas among "IAC", "ordinary patient" and "normal".

Then, in trying to understand if heart rate variation index is related with coma degree, in other words, to see if heart rate variation index can be used to discriminate slight coma patients (group 2a) from deep coma patients (group 2b), Mann-Whitney test (M-W test) [22] using nonparametric statistical analysis was employed to analyze the difference between these two groups. M-W test was similar to t-test except that it does not need to assume a normal population distribution. Table 4 summarized the result obtained by employing M-W test on ordinary patients (Group 2) (slight coma patients vs. deep coma patients).

TABLE 4

Results of M-W test on ordinary patients (Group2) (slight coma patients vs. deep coma patients)

|  | Group 2a Slight coma (n = 19) | Group 2b Deep coma (n = 7) | P-value |
|---|---|---|---|
| Basic Index | | | |
| GCS | 13 (9~5) | 7 (5~8) | <0.0001 |
| Age (yr) | 56 (23~99) | 60 (17~80) | 0.862 |
| HR (beat/min) | 92.34 (55.78~114.62) | 81.86 (64.54~99.43) | 0.418 |
| R-R interval Index | | | |
| R-R mean (ms) | 649.78 (523.46~1075.65) | 732.97 (603.43~929.72) | 0.418 |
| SD (ms) | 31.68 (14.82~83.18) | 37.69 (18.04~85.38) | 0.248 |
| CV | 3.92 (2.06~13.19) | 5.14 (2.09~13.46) | 0.326 |
| SDSD (ms) | 16.63 (4.5~43.1) | 21.96 (7.05~57.79) | 0.165 |
| RMSSD (ms) | 588.09 (194.77~2055.21) | 860.25 (362.47~2326.04) | 0.119 |
| Frequency domain Index | | | |
| HF/TP | 0.08 (0.01~0.76) | 0.1 (0.01~0.44) | 0.298 |
| LFP/HFP | 1.78 (0.11~12.21) | 1.62 (0.59~4.49) | 0.386 |

TABLE 4-continued

Results of M-W test on ordinary patients (Group2) (slight coma patients vs. deep coma patients)

|  | Group 2a Slight coma (n = 19) | Group 2b Deep coma (n = 7) | P-value |
|---|---|---|---|
| Poincaré Index | | | |
| SD1 (ms) | 23.52 (6.37~60.95) | 31.05 (9.97~81.73) | 0.165 |
| SD2 (ms) | 88.29 (41.01~233.27) | 100.56 (40.5~240.83) | 0.272 |
| SD1/SD2 | 0.2 (0.09~1.12) | 0.33 (0.07~0.77) | 0.418 |
| Area (ms$^2$) | 4169.44 (1126.1~32536.5) | 11171.07 (2011.74~55326.1) | 0.203 |

From Table 4, it is understood that, upon analysis by using M-W test, P-values of all HRV parameter in slight coma patient (group 2a) and deep coma patients (group 2b) were >0.05. Accordingly, heart rate variation index could not discriminate the variability between said two sub-group, slight coma patient (group 2a) and deep coma patients (group 2b). Further, Poincaré plots of slight coma patient (group 2a) and deep coma patients (group 2b) displayed no specific shape, and area distribution. Therefore, Poincaré plot could not be used to discriminate these two sub-groups. From a medical point of view, various coma degrees could affect the performance of central nerve, but the difference of heart functions between said two sub-groups was not great. Accordingly, no absolute relationship existed between heart rate variation index and coma degree.

Next, in order to understand whether a same heart rate variation index is present between IAC patients with brain death determination (group 3a) and IAC patients that had no chance to determine brain death (group 3b), M-W test [22] was used to analyze the difference between these two groups. Table 5 lists results obtained by using M-W test on IAC patients (group 3) (IAC patients with brain death determination vs. IAC patients without brain death determination).

TABLE 5

M-W test on IAC patients (group 3) (IAC patients with brain death determination vs. IAC patients without brain death determination)

|  | Group 3a organ donation (n = 5) | Group 3b Normal IAC (n = 11) | P-value |
|---|---|---|---|
| Basic Index | | | |
| GCS | 3 (3~3) | 3 (3~3) | 0.953 |
| Age (yr) | 45 (18~54) | 45 (18~77) | 0.777 |
| HR (beat/min) | 84.8 (71.89~129.44) | 103.37 (65.77~155.71) | 0.428 |
| R-R interval Index | | | |
| R-R mean (ms) | 707.55 (463.52~834.63) | 580.44 (385.32~912.28) | 0.428 |
| SD (ms) | 12.11 (4.76~14.15) | 6.17 (3.66~18.8) | 0.113 |
| CV | 1.65 (1.03~1.71) | 1.06 (0.62~3.03) | 0.141 |
| SDSD (ms) | 8.1 (6.45~9.88) | 5.41 (2.13~16.75) | 0.213 |
| RMSSD (ms) | 295.65 (281.91~437.72) | 233.96 (89.47~930.97) | 0.257 |

TABLE 5-continued

M-W test on IAC patients (group 3) (IAC patients with brain death determination vs. IAC patients without brain death determination)

|  | Group 3a organ donation (n = 5) | Group 3b Normal IAC (n = 11) | P-value |
|---|---|---|---|
| Frequency domain Index | | | |
| HF/TP | 0.21 (0.11~0.48) | 0.24 (0.06~0.87) | 0.650 |
| LFP/HFP | 0.32 (0.18~0.98) | 0.47 (0.08~3.95) | 0.365 |
| Poincaré Index | | | |
| SD1 (ms) | 11.46 (9.12~13.98) | 7.65 (3.01~23.68) | 0.213 |
| SD2 (ms) | 31.28 (8.84~38.24) | 14.96 (6.05~52.04) | 0.113 |
| SD1/SD2 | 0.44 (0.27~1.15) | 0.49 (0.17~3.44) | 0.497 |
| Area ($ms^2$) | 963.94 (281.59~1414.29) | 326.94 (149.98~1818.74) | 0.070 |

From Table 5, it was known that, after statistical analysis by M-W test, P-values of all HRV parameters in IAC patients with brain death determination (group 3a) and IAC patients without chance to determine brain death (group 3b) are >0.05. This result indicated that no difference existed between these two sub-groups. Moreover, Poincaré plots of these two sub-groups had same characteristic pattern. Consequently, these two sub-groups had an identical feature, and hence IAC patients with brain death determination (group 3a) and IAC patients without chance to determine brain death (group 3b) could be considered as a same group. It is known from this example that, for many IAC patients without brain death determination, the tendency of developing into brain death can be found out also via HRV index.

In an intensive care unit, deep coma patients with GCS scale of 3 tend to develop readily into IAC patients through sympathetic storm, and further into brain death. In this example, after analyzing differences in heart rate variability among normal, ordinary patients, and IAC patients, and then performing statistical evaluation, differences of heart rate variability among these three groups can be revealed and conclusions can be obtained as follow:

1. The characteristic pattern of Poincaré plot from an IAC patient is fan type, while the characteristic pattern of Poincaré plot from a normal is comet type.
2. By means of K-W test and Dunn's test, it can be demonstrated that time domain index and Poincaré plot index can discriminate the difference among "normal," "ordinary patient," and "IAC patient".
3. By means of Mann-Whitney test, it can be shown that, HRV index can not discriminate the difference between two sub-groups of a slight coma patient (group 2a) and a deep coma patient (group 2b).
4. By means of Mann-Whitney test, it can be demonstrated that sub-group of IAC patients with brain death determination (group 3a) and sub-group of IAC patients without chance to determine brain death (group 3b) belong to a same group.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

REFERENCES

[1]. Zamperetti N. Bellomo R. Defanti C A, et al., "Irreversible apnoeic coma 35 years later Towards a more rigorous definition of brain death?", Intensive Care Med. Vol 30, No 9, pp: 1715-1722, 2004.
[2]. Wijdicks E F, "Brain death worldwide: accepted fact but no global consensus in diagnostic criteria.", Neurology, 58, PP:20-25, 2002.
[3]. Wijdicks E F, "The diagnosis of brain death.", N Engl J Med. Vol 344, No 16, pp:1215-1221, 2001.
[4]. Shivalkar B. Van Loon J. Wieland W. "Variable effects of explosive or gradual increase of intracranial pressure on myocardial structure and function.", Circulation, Vol 87, pp:230-239, 1993.
[5]. Powner D J, Hendricj A, Nyhuis A, et al., "Changes in serum catecholamine levels in patients who are brain dead.", J Heart Lung Transplant, Vol 11, pp:1046-1053, 1992.
[6]. Smith M., "Physiologic changes during brain stem death—Lessons for management of the organ donor.", J Heart Lung Transplant, Vol 23, pp:217-222, 2004.
[7]. Rappenne T. Moreau D, Lenfant F. et al., "Could heart rate variability analysis become an early predictor of imminent brain death? A pilot study.", Anesth Analg, Vol 91, pp:329-336, 2000.
[8]. Sait M L, Wood A W and Sadafi H A, "A study of heart rate and heart rate variability in human subjects expose to occupational levels of 50 Hz circular polarised magnetic fields.", Medical Engineering & Physics, Vol 21, pp:361-369, 1999.
[9]. Akselrod S. Gordon D, Ubel F A, Shannon D C, Berger A C and Cohen R J., "Power spectral analysis of heart rate fluctuation: a quantitative probe of beat-to-beat cardiovascular control.", Science, Vol 213, No 10, pp:220-222, 1981.
[10]. Pomeranz B. Macaulay R J, Caudill M A, Kutz I, Adam D, Gordon D, Kilborn K M, Barger A C, Shannon D C, Cohen R J, et al, "Assessment of autonomic function in humans by heart rate spectral analysis.", Am J Physiol, Vol 248, pp:151-153, 1985.
[11]. Saul J P, Arai Y. Berger R D, Lilly L S, Colucci W S, and Cohen R J, "Assessment of autonomic regulation in chronic congestive heart failure by heart rate spectral analysis.", Am J Cardiol, Vol 61, pp: 1292-1299, 1988.
[12]. Sands K E F, Appel M L, Lilly L S, Schoen F J, Mudge G H and Cohen R J, "Power spectrum analysis of heart rate variability in human cardiac transplant recipients.", Circulation, Vol 79, pp:76-82, 1989.
[13]. Bianchi A M, Mainardi L, Petrucci E, Signorini M G, Mainardi M and Cerutti S., "Time-variant power spectrum analysis for the detection of transient episodes in HRV signal.", IEEE Trans. Biomedical Engineering, Vol 40, No 2, pp:136-144, 1993.
[14]. Franco S, *Design with operational amplifiers and analog integrated circuits*, McGraw-Hill book company, 1988.
[15]. D'Addio G. Pinna G D, Maestri R, "Correlation between Power-law Behavior and Poincaré plot s of Heart Rate.", IEEE Computer in Cardiology, Vol 26, pp:611-614, 1996.
[16]. Woo M A, Stevenson W G, Moser D K, Trelease R B, Harper Rh4, "Patterns of beat to beat hearth rate variability in advanced heart failure.", Am Heart J, Vol 123, pp:704-710, 1992.

[17]. D'Addio, Pinna, La Rovere, Maestri, Furgi and Rengo, "Prognostic value of Poincaré plot indexes in chronic heart failure patients", Computers in Cardiology, Vol 28, pp:57-60, 2001.

[18]. Tulppo M, Makikallio T H, Takala T. E. S, "Quantitative beat-to-beat analysis of heart rate dynamics during exercise.", American Journal of Physiology.", Vol 40, pp:244-252, 1996.

[19]. Menrad A, et al., "Dual microprocessor system for cardiovascular data acquisition, processing and recording.", in Proc. 1981 IEEE Inr.Con5 Industrial Elect. Contr. Instrument., pp: 64-69, 1981.

[20]. Fraden, J., and Neuman, M R, "QRS wave detection", Med. & Biol. Eng. &. Comput., Vol 18, pp: 125-132, 1980.

[21]. Malik M, "heart rate variability: Standards of Measurement, Physiological Interpretation, and Clinical Use.", Circulation, Vol 93, No. 5, pp: 1043-1065, 1996.

[22]. Stanton A. Glantz, *Primer of Biostatistics*, six edition, McGraw-Hill, North America, 2006.

What is claimed is:

1. A method of analyzing heart rate variability for the presence of irreversible apneic coma (IAC), comprising following steps:

step 1 recording electrocardiogram (ECG) from a subject using a patient monitor;

step 2 analyzing R-R interval in said electrocardiogram (ECG);

step 3 plotting said R-R interval into Poincaré plot, wherein the X coordinate of said Poincaré plot represents R-R interval(n), n is a 1~data number; and Y coordinate of said Poincaré plot represents RR(n+1); and step 4 quantifying said Poincaré plot, and obtaining semi-major axis (SD1), semi-minor axis (SD2), SD1/SD2 of said Poincaré plot, as well as Poincaré plot area;

wherein the semi-major axis (SD1) and semi-minor axis (SD2) of said Poincaré plot are calculated as following:

defining a new axis as X1 and X2;

$$\begin{bmatrix} x1 \\ x2 \end{bmatrix} = \begin{bmatrix} \cos\theta & -\sin\theta \\ \sin\theta & \cos\theta \end{bmatrix} \begin{bmatrix} RR_n \\ RR_{n+1} \end{bmatrix}$$

defining SD1 and SD2 as:

$$SD1^2 = \mathrm{Var}(x_1) = \mathrm{Var}\left(\frac{1}{\sqrt{2}} RR_n - \frac{1}{\sqrt{2}} RR_{n+1}\right)$$
$$= \frac{1}{2}\mathrm{Var}(RR_n - RR_{n+1}) = \frac{1}{2}SDSD^2$$

-continued $$SD2^2 = 2SDRR^2 - \frac{1}{2}SDSD^2$$

wherein SDRR is the standard deviation of R-R interval and SDSD is the standard deviation of $\Delta RR_n$;

wherein said Poincaré plot area is $\Pi \times SD1 \times SD2$;

wherein said R-R intervals is detected through one of method A and method B;

wherein method A is First Derivative (FD1) method, and said FD1 method comprising:

X(n): ECG raw data;

$Y(n)=-2X(n-2)-X(n-1)+X(n+1)+2X(n+2), 2<n<1000$;

wherein, for detecting the position of R wave in Y(n), a slope threshold value is defined as:

Slope threshold=$0.7\max[Y(n)], 2<n<1000$ whereby if Y(i)>slope threshold, Y(i) becomes a region for comparison, and positions of each peaks is selected from Y(i), and wherein the distance between adjacent peaks is the R-R intervals;

wherein method B is an amplitude threshold plus a First Derivative method (AF2 method), said AF2 method comprising:

amplitude threshold=$0.4\max[X(n)], 0<n<1000$ transforming original data into Y0(n):

$Y0(n)=X(n)$ if $X(n)\geq 0, 0<n<1000$ $Y0(n)=-X(n)$ if $X(n)<0, 0<n<1000$ and based on said amplitude threshold, obtaining Y1(n)

$Y1(n)=Y0(n)$ if $Y0(n)\geq$ Amplitude threshold $Y1(n)=$Amplitude threshold if $Y0(n)<$Amplitude threshold Then, by conducting First Derivative, obtaining Y2(n):

$Y2(n)=Y1(n+1)-Y1(n-1), 1<n<2$ wherein, in order to detect the position of R wave in Y2(n), a slope threshold value is defined as:

Slope threshold=$0.7\max[Y(n)], 2<n<1000$ whereby if Y(i)>slope threshold, Y(i) becomes the region for comparison, and positions of each peaks is selected from Y(i), and wherein the distance between adjacent peaks is the R-R intervals;

step 5 determining a reference index from said quantification of said Poincaré plot and providing said reference index to a physician for determining whether brain death has occurred;

wherein steps 2-5 are done using a computing device.

* * * * *